United States Patent
Boutillette et al.

(10) Patent No.: US 10,064,696 B2
(45) Date of Patent: Sep. 4, 2018

(54) DEVICES AND METHODS FOR DELIVERING AN ENDOCARDIAL DEVICE

(71) Applicant: Edwards Lifesciences Corporation, Irvine, CA (US)

(72) Inventors: Michael P. Boutillette, San Francisco, CA (US); James R. Kermode, Menlo Park, CA (US); Miles D. Alexander, Menlo Park, CA (US); Alexander Khairkhahan, Palo Alto, CA (US); Serjan D. Nikolic, San Francisco, CA (US)

(*) Notice: Subject to any disclaimer, the term of this patent is extended or adjusted under 35 U.S.C. 154(b) by 71 days.

(21) Appl. No.: 15/133,080

(22) Filed: Apr. 19, 2016

(65) Prior Publication Data

US 2016/0302924 A1 Oct. 20, 2016

Related U.S. Application Data

(60) Continuation-in-part of application No. 13/827,927, filed on Mar. 14, 2013, now Pat. No. 9,332,992, (Continued)

(51) Int. Cl.
*A61B 17/00* (2006.01)
*A61B 90/00* (2016.01)
(Continued)

(52) U.S. Cl.
CPC ........ *A61B 90/39* (2016.02); *A61B 17/12022* (2013.01); *A61B 17/12122* (2013.01);
(Continued)

(58) Field of Classification Search
CPC ........ A61B 17/12022; A61B 17/12122; A61B 17/12172; A61B 2017/12054; A61B 2017/12095; A61F 2/2418
See application file for complete search history.

(56) References Cited

U.S. PATENT DOCUMENTS 3,874,388 A 4/1975 King et al.
4,007,743 A 2/1977 Blake
(Continued)

FOREIGN PATENT DOCUMENTS

EP 1474032 A2 11/2004
EP 2068768 A 6/2009
(Continued)

OTHER PUBLICATIONS

AGA Medical Corporation. www.amplatzer.com/products. "The Muscular VSD Occluder" and "The Septal Occluder" device description. Accessed Apr. 3, 2002.
(Continued)

*Primary Examiner* — Tammie K Heller

(57) ABSTRACT

Systems for partitioning a ventricle of a heart include a partitioning device or implant, and an applicator for inserting, repositioning and/or removing the partitioning device. The implant may support the ventricle wall and may reduce the volume of the ventricle. The delivery system for delivering and deploying a partitioning device into a ventricle may include a catheter having a distal coupling element for coupling to a partitioning device in a collapsed configuration; the catheter may also have an expansion member for applying force to the partitioning device to fully expand it into a deployed configuration and to secure or seal it against the ventricle wall.

21 Claims, 52 Drawing Sheets

Related U.S. Application Data which is a continuation-in-part of application No. 12/893,832, filed on Sep. 29, 2010, now Pat. No. 9,078,660, which is a continuation-in-part of application No. 11/860,438, filed on Sep. 24, 2007, now Pat. No. 7,897,086, which is a continuation-in-part of application No. 10/913,608, filed on Aug. 5, 2004, now abandoned, said application No. 12/893,832 is a continuation-in-part of application No. 12/509,289, filed on Jul. 24, 2009, now Pat. No. 8,398,537, which is a continuation of application No. 11/151,164, filed on Jun. 10, 2005, now Pat. No. 7,582,051, said application No. 12/893,832 is a continuation-in-part of application No. 13/828,184, filed on Mar. 14, 2013, now Pat. No. 9,332,993, which is a continuation-in-part of application No. 12/893,832, filed on Sep. 29, 2010, now Pat. No. 9,078,660, which is a continuation-in-part of application No. 11/860,438, filed on Sep. 24, 2007, now Pat. No. 7,897,086, which is a continuation-in-part of application No. 10/913,608, filed on Aug. 5, 2004, now abandoned, said application No. 12/893,832 is a continuation-in-part of application No. 12/509,289, filed on Jul. 24, 2009, now Pat. No. 8,398,537, which is a continuation of application No. 11/151,164, filed on Jun. 10, 2005, now Pat. No. 7,582,051, said application No. 12/893,832 is a continuation-in-part of application No. 14/731,161, filed on Jun. 4, 2015, now abandoned, which is a division of application No. 12/893,832, filed on Sep. 29, 2010, now Pat. No. 9,078,660, which is a continuation-in-part of application No. 11/860,438, filed on Sep. 24, 2007, now Pat. No. 7,897,086, which is a continuation-in-part of application No. 10/913,608, filed on Aug. 5, 2004, now abandoned, said application No. 12/893,832 is a continuation-in-part of application No. 12/509,289, filed on Jul. 24, 2009, now Pat. No. 8,398,537, which is a continuation of application No. 11/151,164, filed on Jun. 10, 2005, now Pat. No. 7,582,051.

(60) Provisional application No. 61/246,920, filed on Sep. 29, 2009.

(51) Int. Cl.
| | |
|---|---|
| *A61M 25/09* | (2006.01) |
| *A61B 17/12* | (2006.01) |
| *B29C 70/74* | (2006.01) |
| *B29C 43/18* | (2006.01) |
| *B29L 31/00* | (2006.01) |
| *B29C 65/18* | (2006.01) |
| *B29C 65/00* | (2006.01) |

(52) U.S. Cl.
CPC ....... *A61B 17/12172* (2013.01); *A61M 25/09* (2013.01); *B29C 70/74* (2013.01); *A61B 2017/00243* (2013.01); *A61B 2017/00526* (2013.01); *A61B 2017/00867* (2013.01); *A61B 2017/12054* (2013.01); *A61B 2017/12095* (2013.01); *A61B 2090/3966* (2016.02); *B29C 43/18* (2013.01); *B29C 65/18* (2013.01); *B29C 66/1122* (2013.01); *B29C 66/532* (2013.01); *B29C 66/53261* (2013.01); *B29C 66/545* (2013.01); *B29C 66/636* (2013.01); *B29C 66/71* (2013.01); *B29C 66/712* (2013.01); *B29C 66/727* (2013.01); *B29C 66/729* (2013.01); *B29C 66/81429* (2013.01); *B29C 66/81431* (2013.01); *B29C 66/8322* (2013.01); *B29L 2031/753* (2013.01)

(56) References Cited

U.S. PATENT DOCUMENTS

| | | |
|---|---|---|
| 4,425,908 A | 1/1984 | Simon |
| 4,453,545 A | 6/1984 | Inoue |
| 4,536,893 A | 8/1985 | Parravicini |
| 4,588,404 A | 5/1986 | Lapeyre |
| 4,619,246 A | 10/1986 | Molgaard-Nielsen et al. |
| 4,685,446 A | 8/1987 | Choy |
| 4,710,192 A | 12/1987 | Liotta et al. |
| 4,819,751 A | 4/1989 | Shimada et al. |
| 4,832,055 A | 5/1989 | Palestrant |
| 4,917,089 A | 4/1990 | Sideris |
| 4,983,165 A | 1/1991 | Loiterman |
| 5,104,399 A | 4/1992 | Lazarus |
| 5,192,301 A | 3/1993 | Kamiya et al. |
| 5,192,314 A | 3/1993 | Daskalakis |
| 5,258,000 A | 11/1993 | Gianturco |
| 5,375,612 A | 12/1994 | Cottenceau et al. |
| 5,385,156 A | 1/1995 | Oliva |
| 5,389,087 A | 2/1995 | Miraki |
| 5,425,744 A | 6/1995 | Fagan et al. |
| 5,433,727 A | 7/1995 | Sideris |
| 5,451,235 A | 9/1995 | Lock et al. |
| 5,496,277 A | 3/1996 | Termin et al. |
| 5,527,337 A | 6/1996 | Stack et al. |
| 5,527,338 A | 6/1996 | Purdy |
| 5,549,621 A | 8/1996 | Bessler et al. |
| 5,551,435 A | 9/1996 | Sramek |
| 5,578,069 A | 11/1996 | Miner, II |
| 5,634,936 A | 6/1997 | Linden et al. |
| 5,634,942 A | 6/1997 | Chevillon et al. |
| 5,647,870 A | 7/1997 | Kordis et al. |
| 5,702,343 A | 12/1997 | Alferness |
| 5,709,707 A | 1/1998 | Lock et al. |
| 5,758,664 A | 6/1998 | Campbell et al. |
| 5,791,231 A | 8/1998 | Cohn et al. |
| 5,797,849 A | 8/1998 | Vesely et al. |
| 5,797,960 A | 8/1998 | Stevens et al. |
| 5,800,457 A | 9/1998 | Gelbfish |
| 5,800,517 A | 9/1998 | Anderson et al. |
| 5,829,447 A | 11/1998 | Stevens et al. |
| 5,833,682 A | 11/1998 | Amplatz et al. |
| 5,833,698 A | 11/1998 | Hinchliffe et al. |
| 5,836,968 A | 11/1998 | Simon et al. |
| 5,843,170 A | 12/1998 | Ahn |
| 5,860,951 A | 1/1999 | Eggers et al. |
| 5,861,003 A | 1/1999 | Latson et al. |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,910,150 A | 6/1999 | Saadat |
| 5,916,145 A | 6/1999 | Chu et al. |
| 5,924,424 A | 7/1999 | Stevens et al. |
| 5,925,062 A | 7/1999 | Purdy |
| 5,925,076 A | 7/1999 | Inoue |
| 5,928,260 A | 7/1999 | Chin et al. |
| 5,961,440 A | 10/1999 | Schweich, Jr. et al. |
| 5,961,539 A | 10/1999 | Northrup, III et al. |
| 5,984,917 A | 11/1999 | Fleischman et al. |
| 6,024,096 A | 2/2000 | Buckberg |
| 6,024,756 A | 2/2000 | Huebsch et al. |
| 6,036,720 A | 3/2000 | Abrams et al. |
| 6,045,497 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |

(56) References Cited

U.S. PATENT DOCUMENTS

| | | |
|---|---|---|
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,125,852 A | 10/2000 | Stevens et al. |
| 6,132,438 A | 10/2000 | Fleischman et al. |
| 6,142,973 A | 11/2000 | Carleton et al. |
| 6,152,144 A | 11/2000 | Lesh et al. |
| 6,155,968 A | 12/2000 | Wilk |
| 6,156,027 A | 12/2000 | West |
| 6,161,543 A | 12/2000 | Cox et al. |
| 6,193,731 B1 | 2/2001 | Oppelt et al. |
| 6,221,092 B1 | 4/2001 | Koike et al. |
| 6,221,104 B1 | 4/2001 | Buckberg et al. |
| 6,230,714 B1 | 5/2001 | Alferness et al. |
| 6,231,561 B1 | 5/2001 | Frazier et al. |
| 6,258,021 B1 | 7/2001 | Wilk |
| 6,267,772 B1 | 7/2001 | Mulhauser et al. |
| 6,290,674 B1 | 9/2001 | Roue et al. |
| 6,296,656 B1 | 10/2001 | Bolduc et al. |
| 6,312,446 B1 | 11/2001 | Huebsch et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,355,052 B1 | 3/2002 | Neuss et al. |
| 6,360,749 B1 | 3/2002 | Jayaraman |
| 6,364,896 B1 | 4/2002 | Addis |
| 6,387,042 B1 | 5/2002 | Herrero |
| 6,406,420 B1 | 6/2002 | McCarthy et al. |
| 6,419,669 B1 | 7/2002 | Frazier et al. |
| 6,436,088 B2 | 8/2002 | Frazier et al. |
| 6,450,171 B1 | 9/2002 | Buckberg et al. |
| 6,482,146 B1 | 11/2002 | Alferness et al. |
| 6,482,228 B1 | 11/2002 | Norred |
| 6,506,204 B2 | 1/2003 | Mazzocchi |
| 6,508,756 B1 | 1/2003 | Kung et al. |
| 6,511,496 B1 | 1/2003 | Huter et al. |
| 6,537,198 B1 | 3/2003 | Vidlund et al. |
| 6,551,303 B1 | 4/2003 | Van Tassel et al. |
| 6,572,643 B1 | 6/2003 | Gharibadeh |
| 6,586,414 B2 | 7/2003 | Haque et al. |
| 6,592,608 B2 | 7/2003 | Fisher et al. |
| 6,613,013 B2 | 9/2003 | Haarala et al. |
| 6,622,730 B2 | 9/2003 | Ekvall et al. |
| 6,645,199 B1 | 11/2003 | Jenkins et al. |
| 6,652,555 B1 | 11/2003 | Van Tassel et al. |
| 6,681,773 B2 | 1/2004 | Murphy et al. |
| 6,685,627 B2 | 2/2004 | Jayaraman |
| 6,702,763 B2 | 3/2004 | Murphy et al. |
| 6,730,108 B2 | 5/2004 | Van Tassel et al. |
| 6,776,754 B1 | 8/2004 | Wilk |
| 6,852,076 B2 | 2/2005 | Nikolic et al. |
| 6,887,192 B1 | 5/2005 | Whayne et al. |
| 6,951,534 B2 | 10/2005 | Girard et al. |
| 6,959,711 B2 | 11/2005 | Murphy et al. |
| 6,994,093 B2 | 2/2006 | Murphy et al. |
| 7,144,363 B2 | 12/2006 | Pai et al. |
| 7,172,551 B2 | 2/2007 | Leasure |
| 7,175,660 B2 | 2/2007 | Cartledge et al. |
| 7,279,007 B2 | 10/2007 | Nikolic et al. |
| 7,303,526 B2 | 12/2007 | Sharkey et al. |
| 7,320,665 B2 | 1/2008 | Vijay |
| 7,399,271 B2 | 7/2008 | Khairkhahan et al. |
| 7,485,088 B2 | 2/2009 | Murphy et al. |
| 7,513,867 B2 * | 4/2009 | Lichtenstein ...... A61B 17/0057 600/37 |
| 7,530,998 B1 | 5/2009 | Starkey |
| 7,569,062 B1 | 8/2009 | Kuehn et al. |
| 7,582,051 B2 | 9/2009 | Khairkhahan et al. |
| 7,674,222 B2 | 3/2010 | Nikolic et al. |
| 7,758,491 B2 | 7/2010 | Buckner et al. |
| 7,762,943 B2 | 7/2010 | Khairkhahan |
| 7,824,325 B2 | 11/2010 | Dubi |
| 7,862,500 B2 | 1/2011 | Khairkhahan et al. |
| 7,887,477 B2 | 2/2011 | Sharkey et al. |
| 7,897,086 B2 | 3/2011 | Khairkhahan et al. |
| 7,938,767 B2 | 5/2011 | Evans et al. |
| 7,976,455 B2 | 7/2011 | Khairkhahan |
| 7,993,258 B2 | 8/2011 | Feld et al. |
| 8,192,478 B2 | 6/2012 | Khairkhahan et al. |
| 8,246,671 B2 | 8/2012 | Khairkhahan et al. |
| 8,257,428 B2 | 9/2012 | Khairkhahan et al. |
| 8,377,114 B2 | 2/2013 | Khairkhahan et al. |
| 8,382,653 B2 | 2/2013 | Dubi et al. |
| 8,388,672 B2 | 3/2013 | Khairkhahan et al. |
| 8,398,537 B2 | 3/2013 | Khairkhahan et al. |
| 8,500,622 B2 | 8/2013 | Lipperman et al. |
| 8,500,790 B2 | 8/2013 | Khairkhahan |
| 8,500,795 B2 | 8/2013 | Khairkhahan et al. |
| 8,529,430 B2 | 9/2013 | Nikolic et al. |
| 8,657,873 B2 | 2/2014 | Khairkhahan et al. |
| 8,672,827 B2 | 3/2014 | Nikolic et al. |
| 8,790,242 B2 | 7/2014 | Kermode et al. |
| 8,827,892 B2 | 9/2014 | Nikolic et al. |
| 9,017,394 B2 | 4/2015 | Khairkhahan |
| 9,039,597 B2 | 5/2015 | Kermode et al. |
| 9,078,660 B2 | 7/2015 | Boutillette et al. |
| 9,332,992 B2 | 5/2016 | Alexander |
| 9,332,993 B2 | 5/2016 | Kermode et al. |
| 9,364,327 B2 | 6/2016 | Kermode et al. |
| 2001/0014800 A1 | 8/2001 | Frazier et al. |
| 2002/0019580 A1 | 2/2002 | Lau et al. |
| 2002/0026092 A1 | 2/2002 | Buckberg et al. |
| 2002/0028981 A1 | 3/2002 | Lau et al. |
| 2002/0032481 A1 | 3/2002 | Gabbay |
| 2002/0055767 A1 | 5/2002 | Forde et al. |
| 2002/0055775 A1 | 5/2002 | Carpentier et al. |
| 2002/0111647 A1 | 8/2002 | Khairkhahan et al. |
| 2002/0133227 A1 | 9/2002 | Murphy et al. |
| 2002/0161392 A1 | 10/2002 | Dubrul |
| 2002/0161394 A1 | 10/2002 | Macoviak et al. |
| 2002/0169359 A1 | 11/2002 | McCarthy et al. |
| 2002/0169360 A1 | 11/2002 | Taylor et al. |
| 2002/0183604 A1 | 12/2002 | Gowda et al. |
| 2002/0188170 A1 | 12/2002 | Santamore et al. |
| 2003/0045896 A1 | 3/2003 | Murphy et al. |
| 2003/0078671 A1 | 4/2003 | Lesniak et al. |
| 2003/0109770 A1 | 6/2003 | Sharkey et al. |
| 2003/0120337 A1 | 6/2003 | Van Tassel et al. |
| 2003/0135230 A1 | 7/2003 | Massey et al. |
| 2003/0149333 A1 | 8/2003 | Alferness |
| 2003/0149422 A1 | 8/2003 | Muller |
| 2003/0181942 A1 | 9/2003 | Sutton et al. |
| 2003/0220667 A1 | 11/2003 | van der Burg et al. |
| 2004/0002626 A1 | 1/2004 | Feld et al. |
| 2004/0034366 A1 | 2/2004 | van der Burg et al. |
| 2004/0044361 A1 | 3/2004 | Frazier et al. |
| 2004/0054394 A1 | 3/2004 | Lee |
| 2004/0064014 A1 | 4/2004 | Melvin et al. |
| 2004/0122090 A1 | 6/2004 | Lipton |
| 2004/0127935 A1 | 7/2004 | Van Tassel et al. |
| 2004/0133062 A1 | 7/2004 | Pai et al. |
| 2004/0136992 A1 | 7/2004 | Burton et al. |
| 2004/0172042 A1 | 9/2004 | Suon et al. |
| 2004/0186511 A1 | 9/2004 | Stephens et al. |
| 2004/0215230 A1 | 10/2004 | Frazier et al. |
| 2004/0220610 A1 * | 11/2004 | Kreidler ............ A61B 17/0057 606/200 |
| 2004/0243170 A1 | 12/2004 | Suresh et al. |
| 2004/0260331 A1 | 12/2004 | D'Aquanni et al. |
| 2004/0260346 A1 | 12/2004 | Overall et al. |
| 2004/0267086 A1 | 12/2004 | Anstadt et al. |
| 2004/0267378 A1 | 12/2004 | Gazi et al. |
| 2005/0007031 A1 | 1/2005 | Hyder |
| 2005/0015109 A1 | 1/2005 | Lichtenstein |
| 2005/0038470 A1 | 2/2005 | van der Burg et al. |
| 2005/0043708 A1 | 2/2005 | Gleeson et al. |
| 2005/0065548 A1 | 3/2005 | Marino et al. |
| 2005/0085826 A1 | 4/2005 | Nair et al. |
| 2005/0096498 A1 | 5/2005 | Houser et al. |
| 2005/0113811 A1 | 5/2005 | Houser et al. |
| 2005/0113861 A1 | 5/2005 | Corcoran et al. |

(56) References Cited

U.S. PATENT DOCUMENTS

| | | |
|---|---|---|
| 2005/0124849 A1 | 6/2005 | Barbut et al. |
| 2005/0137690 A1 | 6/2005 | Salahieh et al. |
| 2005/0142180 A1 | 6/2005 | Bisgaier et al. |
| 2005/0177180 A1 | 8/2005 | Kaganov et al. |
| 2005/0187620 A1 | 8/2005 | Pai et al. |
| 2005/0216052 A1 | 9/2005 | Mazzocchi et al. |
| 2005/0228434 A1 | 10/2005 | Amplatz et al. |
| 2005/0277981 A1 | 12/2005 | Maahs et al. |
| 2005/0277983 A1 | 12/2005 | Saadat et al. |
| 2005/0283218 A1 | 12/2005 | Williams |
| 2006/0019888 A1 | 1/2006 | Zhou |
| 2006/0025800 A1 | 2/2006 | Suresh |
| 2006/0030881 A1 | 2/2006 | Sharkey et al. |
| 2006/0063970 A1 | 3/2006 | Raman et al. |
| 2006/0069430 A9 | 3/2006 | Randert et al. |
| 2006/0079736 A1 | 4/2006 | Chin et al. |
| 2006/0116692 A1 | 6/2006 | Ward |
| 2006/0136043 A1 | 6/2006 | Cully et al. |
| 2006/0199995 A1 | 9/2006 | Vijay |
| 2006/0229491 A1 | 10/2006 | Sharkey et al. |
| 2006/0259124 A1 | 11/2006 | Matsuoka et al. |
| 2006/0276684 A1 | 12/2006 | Speziali |
| 2006/0293739 A1* | 12/2006 | Vijay ............... A61B 17/12022 607/122 |
| 2007/0129753 A1 | 6/2007 | Quinn et al. |
| 2007/0135889 A1 | 6/2007 | Moore et al. |
| 2007/0162048 A1 | 7/2007 | Quinn et al. |
| 2007/0213578 A1 | 9/2007 | Khairkhahan et al. |
| 2008/0015717 A1 | 1/2008 | Griffin et al. |
| 2008/0045778 A1 | 2/2008 | Lichtenstein et al. |
| 2008/0228205 A1 | 9/2008 | Sharkey et al. |
| 2009/0112050 A1 | 4/2009 | Farnan et al. |
| 2010/0030256 A1 | 2/2010 | Dubrul et al. |
| 2010/0057185 A1 | 3/2010 | Melsheimer et al. |
| 2010/0274227 A1 | 10/2010 | Khairkhahan et al. |
| 2011/0092761 A1 | 4/2011 | Almog et al. |
| 2011/0178362 A1 | 7/2011 | Evans et al. |
| 2011/0264204 A1 | 10/2011 | Khairkhahan |
| 2012/0041257 A1 | 2/2012 | Stankus et al. |
| 2012/0245604 A1 | 9/2012 | Tegzes |
| 2013/0090677 A1 | 4/2013 | Evans et al. |
| 2013/0165735 A1 | 6/2013 | Khairkhahan et al. |
| 2014/0180271 A1 | 6/2014 | Johnson et al. |
| 2014/0343356 A1 | 11/2014 | Nikolic et al. |
| 2015/0209144 A1 | 7/2015 | Khairkhahan |
| 2015/0265405 A1 | 9/2015 | Boutillette et al. |

FOREIGN PATENT DOCUMENTS

| | | |
|---|---|---|
| EP | 2344070 A | 7/2011 |
| EP | 2244661 B1 | 3/2012 |
| EP | 2082690 B1 | 6/2012 |
| JP | H08257031 A | 10/1996 |
| JP | 2001520910 A | 11/2001 |
| JP | 2003512128 A | 4/2003 |
| JP | 2003512129 A | 4/2003 |
| JP | 2005324019 | 11/2005 |
| KR | 10-1070811 B1 | 10/2011 |
| WO | WO 96/37859 A1 | 11/1996 |
| WO | WO 98/03213 A1 | 1/1998 |
| WO | WO 00/27292 A1 | 5/2000 |
| WO | WO 00/42919 A1 | 7/2000 |
| WO | WO 00/50639 A2 | 8/2000 |
| WO | WO 01/30266 A1 | 5/2001 |
| WO | WO 01/78625 A1 | 10/2001 |
| WO | WO 02/30335 A2 | 4/2002 |
| WO | WO 02/45710 A1 | 6/2002 |
| WO | WO 02/071977 A2 | 9/2002 |
| WO | WO 02/087481 A1 | 11/2002 |
| WO | WO 03/007778 A2 | 1/2003 |
| WO | WO 03/043507 A2 | 5/2003 |
| WO | WO 03/073961 A1 | 9/2003 |
| WO | WO 03/090716 A1 | 11/2003 |
| WO | WO 03/099300 A1 | 12/2003 |
| WO | WO 03/099320 A1 | 12/2003 |
| WO | WO 03/103538 A1 | 12/2003 |
| WO | WO 03/103743 A2 | 12/2003 |
| WO | WO 2004/012629 A1 | 2/2004 |
| WO | WO 2004/019866 A2 | 3/2004 |
| WO | WO 2004/066805 A2 | 8/2004 |
| WO | WO 2004/100803 A1 | 11/2004 |
| WO | WO 2005/007031 A2 | 1/2005 |
| WO | WO 2005/007873 A2 | 1/2005 |
| WO | WO 2005/041745 A2 | 5/2005 |
| WO | WO 2005/091860 A2 | 10/2005 |
| WO | WO 2005/102181 A1 | 11/2005 |
| WO | WO 2006/033107 A2 | 3/2006 |
| WO | WO 2006/055683 A2 | 5/2006 |
| WO | WO 2007/016349 A2 | 2/2007 |
| WO | WO 2007/092354 A2 | 8/2007 |
| WO | WO 2007/143560 A2 | 12/2007 |
| WO | WO 2008/010792 A1 | 1/2008 |
| WO | WO 2011/011641 A2 | 1/2011 |
| WO | WO2012/099418 A2 | 7/2012 |
| WO | WO2013065036 A2 | 5/2013 |
| WO | WO 2013/128461 A1 | 9/2013 |

OTHER PUBLICATIONS

Anand et al.; Isolated myocyte contractile function is normal in postinfarct remodeled rat heart with systolic dysfunction; Circulation ; 96(11); pp. 3974-3984; Dec. 1997.

Artrip et al.; Left ventricular volume reduction surgery for heart failure: A physiologic perspective; J Thorac Cardiovasc Surg; vol. 122; No. 4; pp. 775-782; Oct. 2001.

Boersma et al.; Early thrombolytic treatment in acute myocardial infarction: reappraisal of the golden hour; Lancet: vol. 348(9030); pp. 771-775; Sep. 21, 1996.

Bozdag-Turan et al.; Left ventricular partitioning device in a patient with chronic heart failure: Short-term clinical follow-up; Int J Cardiol; 163(1); pp. e1-e3; (Epub) Jul. 2012.

Dang et al.; Akinetic myocardial infarcts must contain contracting myocytes: finite-element model study; Am J Physiol Heart Circ Physiol ; 288; pp. H1844-H1850; Apr. 2005.

Dang et al.; Effect of ventricular size and patch stiffness in surgical anterior ventricular restoration: a finite element model study; Ann Thorac Surg; 79; pp. 185-193; Jan. 2005.

Di Mattia, et al. Surgical treatment of left ventricular post-infarction aneurysm with endoventriculoplasty: late clinical and functioal results. European Journal of Cardio-thoracic Surgery. 15(4):413-418; Apr. 1999.

Dor, et al. Ventricular remodeling in coronary artery disease. Current Opinion in Cardiology. 12(6):533-537; Nov. 1997.

Dor, V. The treatment of refractory ischemic ventricular tachycardia by endoventricular patch plasty reconstruction of the left ventricle. Seminars in Thoracic and Cardiovascular Surgery. 9(2): 146-155; Apr. 1997.

Dor. Surgery for left ventricular aneurysm. Current Opinion in Cardiology. vol. 5; No. 6; pp. 773-780; Dec. 1990.

Gore Medical. www.goremedical.com. "Helex Septal Occluder" product description. Accessed Apr. 3, 2002.

Grossman et al.; Wall stress and patterns of hypertrophy in the human left ventricle; J Clin Invest; 56; pp. 56-64; Jul. 1975.

Guccione et al.; Finite element stress analysis of left ventricular mechanics in the beating dog heart; J Biomech; 28; pp. 1167-1177; Oct. 1995.

Guccione et al.; Mechanics of active contraction in cardiac muscle: Part II—Cylindrical models of the systolic left ventricle; J Biomech Eng; 115; pp. 82-90; Feb. 1993.

Gutberlet et al.; Myocardial viability assessment in patients with highly impaired left ventricular function: comparison of delayed enhancement, dobutamine stress MRI, end-diastolic wall thickness, and TI201-SPECT with functional recovery after revascularization; Eur Radiol; 15; pp. 872-880; May 2005.

Huisman et al.; Measurement of left ventricular wall stress; Cardiovascular Research; 14; pp. 142-153; Mar. 1980.

(56) References Cited

OTHER PUBLICATIONS

Jackson et al.; Extension of borderzone myocardium in postinfarction dilated cardiomyopathy; J Am Coll Cardiol; 40(6); 1160-7; and discussion; pp. 1168-1171; Sep. 2002.

James et al.; Blood Volume and Brain Natriuretic Peptide in Congestive Heart Failure: A Pilot Study; American Heart Journal; vol. 150; issue 5, pp. 984.e1-984.e6 (abstract); Dec. 6, 2005.

Januzzi, James L.; Natriuretic peptide testing: A window into the diagnosis and prognosis of heart failure; Cleveland Clinic Journal of Medicine; vol. 73; No. 2; pp. 149-152 and 155-157; Feb. 2006.

Jones et al.; Coronary Bypass Surgery with or without Surgical Ventricular Reconstruction; N Engl J Med; 360; pp. 1705-1717; Apr. 2009.

Katsumata, et al. An objective appraisal of partial left ventriculectomy for heart failure. Journal of Congestive Heart Failure and Circulator Support. 1(2): 97-106; (year of pub. sufficiently earlier than effective US filing date and any foreign priority date) 1999.

Kawata, et al. Systolic and Diastolic Function after Patch Reconstruction of Left Ventricular Aneurysms. Ann. Thorac. Surg. 5(2)9:403-407; Feb. 1995.

Lee et al.; A novel method for quantifying in-vivo regional left ventricular myocardial contractility in the border zone of a myocardial infarction (author manuscript, 11 pgs.); J Biomech Eng; 133; 094506; Sep. 2011.

Mazzaferri et al.; Percutaneous left ventricular partitioning in patients with chronic heart failure and a prior anterior myocardial infarction: Results of the Percutaneous Ventricular Restoration in Chronic Heart Failure Patients Trial; Am Heart J; 163; pp. 812-820; May 2012.

Nikolic et al.; Percutaneous implantation of an intraventricular device for the treatment of heart failure: experimental results and proof of concept; J Card Fail; 15(9); pp. 790-797; Nov. 2009.

Priola et al.; Functional characteristics of the left ventricular inflow and outflow tracts; Circ Res; 17; pp. 123-129; Aug. 1965.

Sagic et al.; Percutaneous implantation of the left ventricular partitioning device for chronic heart failure: a pilot study with 1-year follow-up. Eur J Heart Fail; 12; pp. 600-606; Apr. 2010.

Sharkey et al.; Left ventricular apex occluder. Description of a a ventricular partitioning device; EuroInterv.; 2(1); pp. 125-127; May 2006.

Sojitra et al.; Electropolishing of 316LVM stainless steel cardiovascular stents: an investigation of material removal, surface roughness and corrosion behaviour; Trends Biomater. Artif. Organs; 23(3); pp. 115-121; (year of pub. sufficiently earlier than effective US filing date and any foreign priority date) 2010.

Sun et al.; A computationally efficient formal optimization of regional myocardial contractility in a sheep with left ventricular aneurysm (author manuscript, 21 pgs.); J Biomech Eng; 131; 111001; Nov. 2009.

U.S. Food & Drug Administration; AneuRx Stent Graft System—Instructions for use; (pre-market approval); Sep. 29, 1999; downloaded Apr. 25, 2013 (http://www.accessdata.fda.gov/cdrh_docs/pdf/P990020c.pdf).

Walker et al; Magnetic resonance imaging-based finite element stress analysis after linear repair of left ventricular aneurysm (author manuscript, 17 pgs.); J Thorac Cardiovasc Surg; 135; pp. 1094-1102 e1-2; May 2008.

Walker et al; MRI-based finite-element analysis of left ventricular aneurysm; Am J Physiol Heart Circ Physiol; 289; pp. H692-H700; Aug. 2005.

Walmsley; Anatomy of left ventricular outflow tract; British Heart Journal; 41; pp. 263-267; Mar. 1979.

Wenk et al.; First evidence of depressed contractility in the border zone of a human myocardial infarction; Ann Thorac Surg; 93; pp. 1188-1193; Apr. 2012.

Wenk et al.; Regional left ventricular myocardial contractility and stress in a finite element model of posterobasal myocardial infarction (author manuscript, pgs.); J Biomech Eng; 133(4); 044501; Apr. 2011.

\* cited by examiner

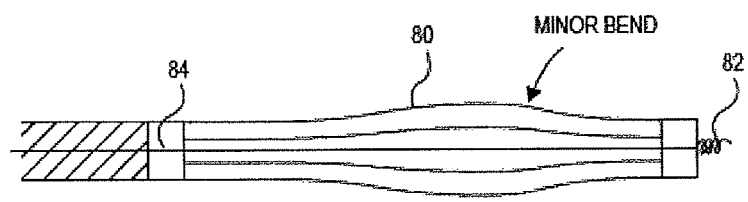
FIG. 22 RESTING SHAPE
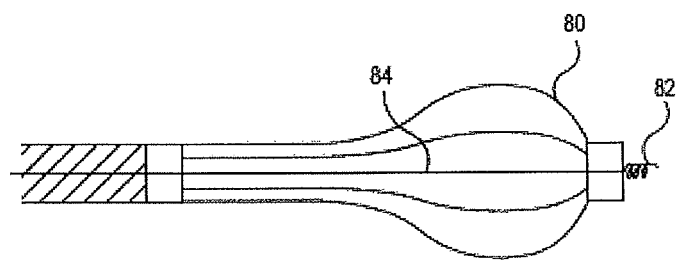
FIG. 23 RESTING SHAPE
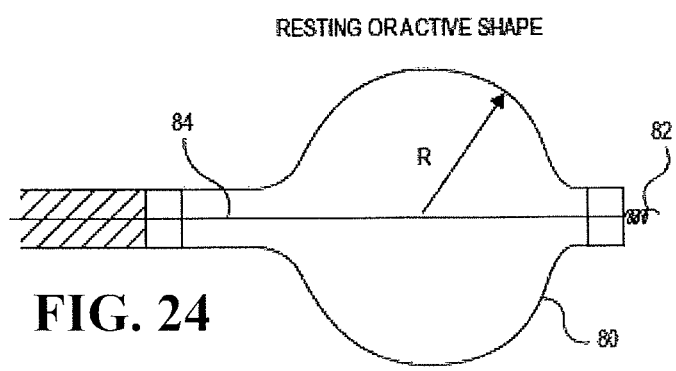
FIG. 24

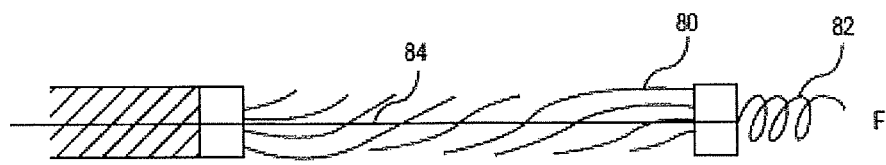
FIG. 25 RESTING SHAPE
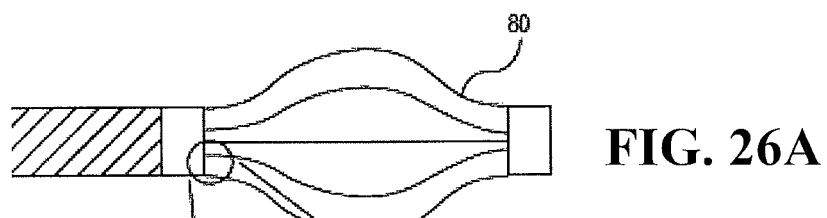
FIG. 26A
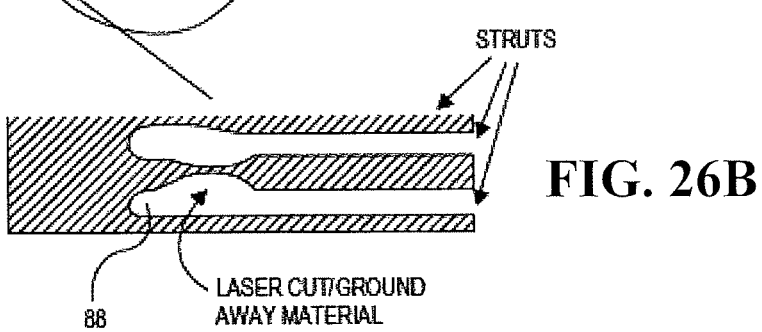
FIG. 26B

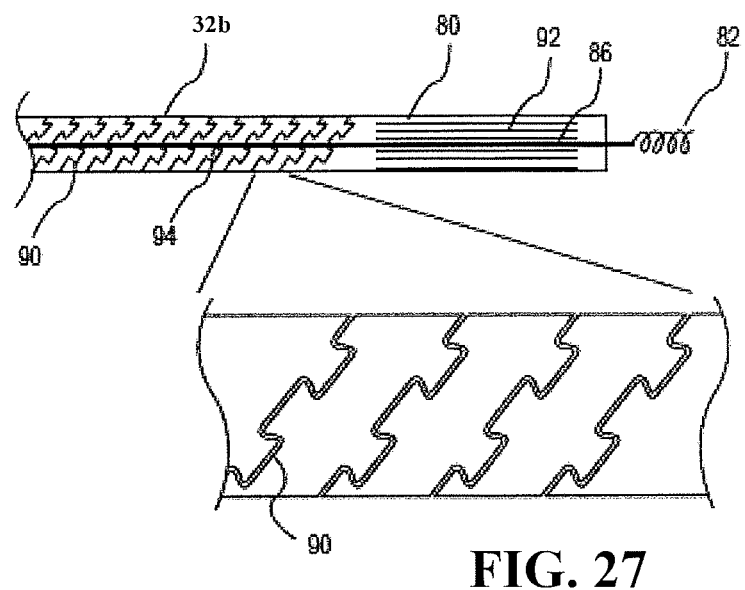
FIG. 27
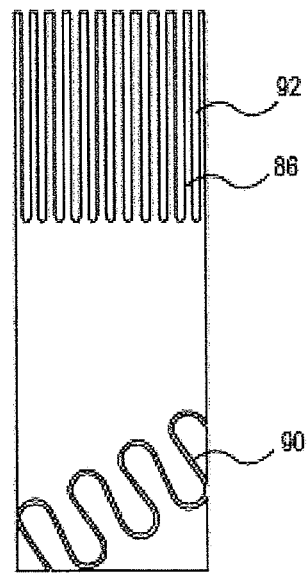 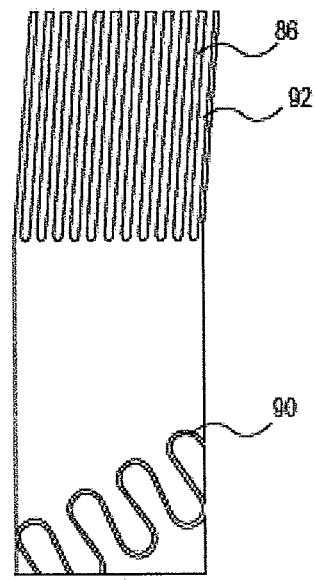
FIG. 28A  FIG. 28B

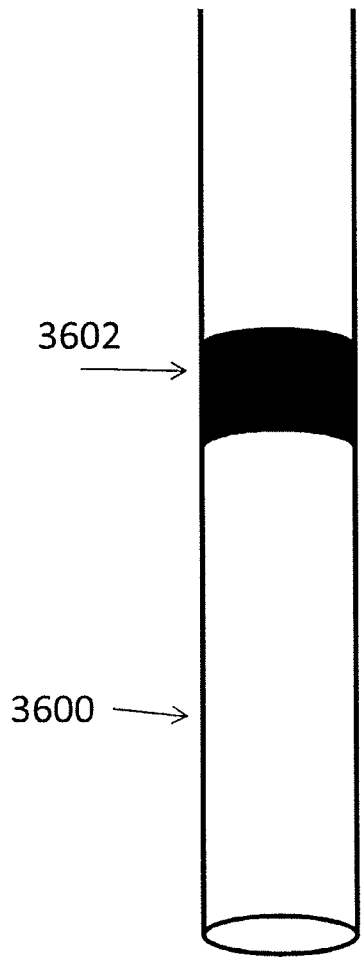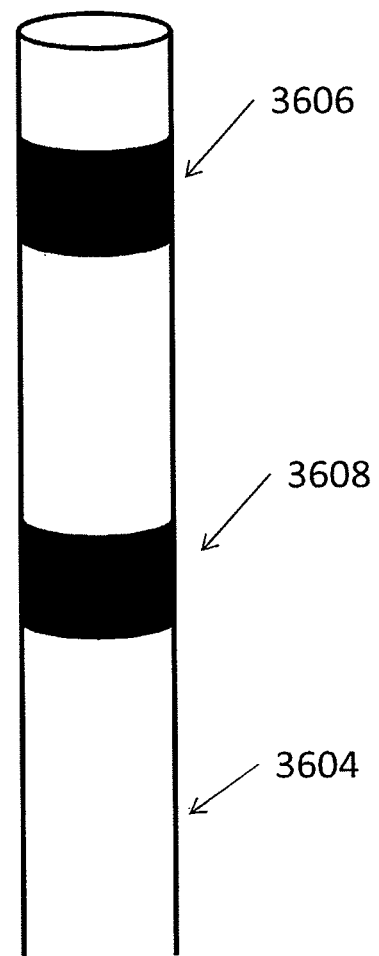
FIG. 41A
FIG. 41B

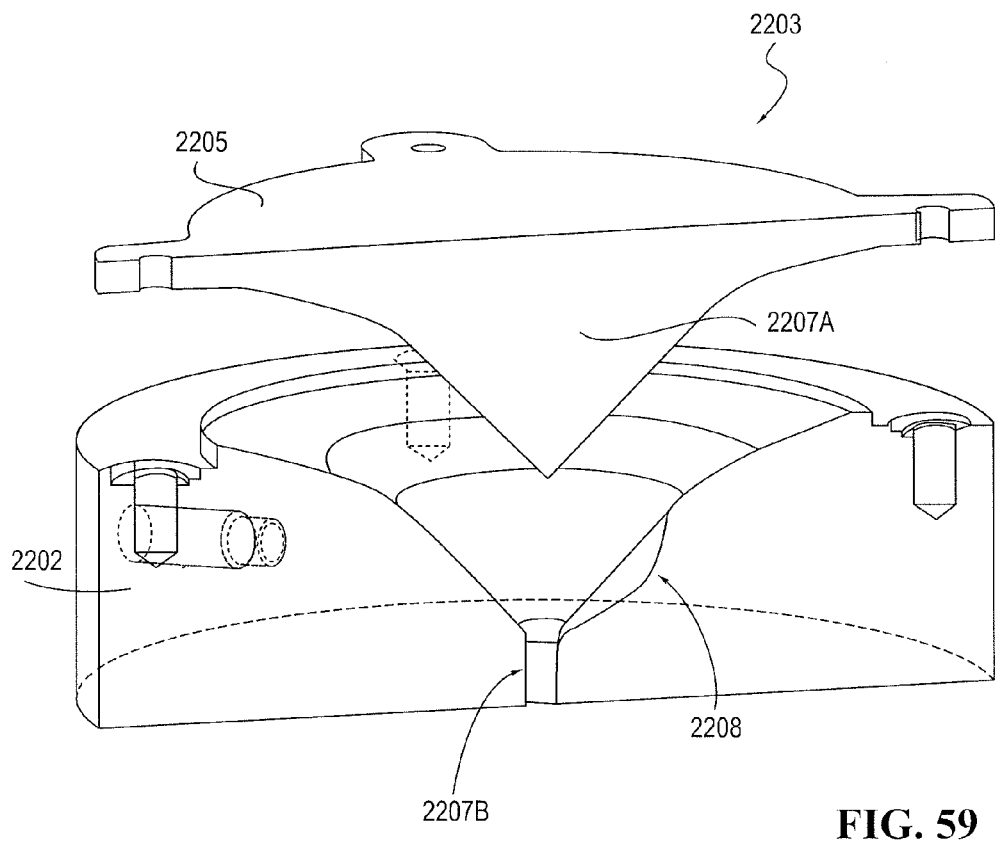
FIG. 59
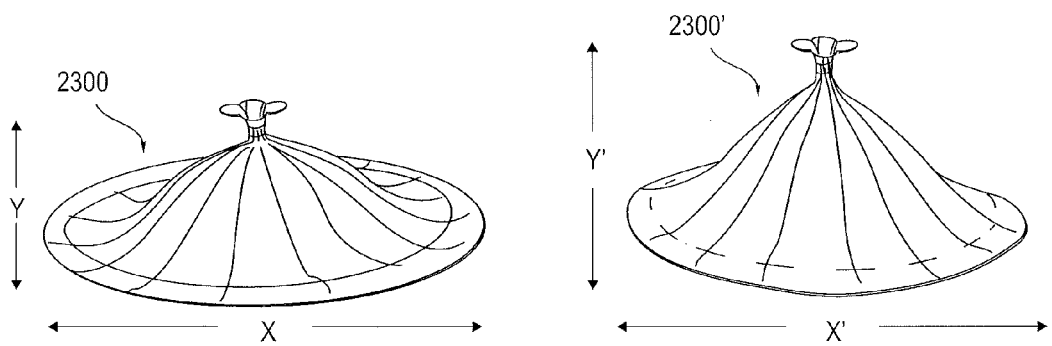
FIG. 60A  FIG. 60B

DEVICES AND METHODS FOR DELIVERING AN ENDOCARDIAL DEVICE

CROSS-REFERENCE TO RELATED APPLICATIONS

This patent application claims priority as a continuation-in-part of U.S. patent application Ser. No. 13/827,927, filed on Mar. 14, 2013, now U.S. Pat. No. 9,332,992, and as a continuation-in-part of U.S. patent application Ser. No. 13/828,184, filed Mar. 13, 2013, now U.S. Pat. No. 9,332,993, both of which are continuations-in-parts of U.S. patent application Ser. No. 12/893,832, filed on Sep. 29, 2010, now U.S. Pat. No. 9,078,660, which is a continuation-in-part of U.S. patent application Ser. No. 11/860,438, filed on Sep. 24, 2007, now U.S. Pat. No. 7,897,086, which is a continuation-in-part of U.S. patent application Ser. No. 10/913,608, filed on Aug. 5, 2004, now abandoned. Each of these patent applications is herein incorporated by reference in their entirety.

U.S. patent application Ser. No. 12/893,832 also claims priority as a continuation-in-part of U.S. patent application Ser. No. 12/509,289, filed on Jul. 24, 2009, now U.S. Pat. No. 8,398,537, which is a continuation of U.S. patent application Ser. No. 11/151,164, filed on Jun. 10, 2005, now U.S. Pat. No. 7,582,051. U.S. patent application Ser. No. 12/893,832 also claims priority to U.S. Provisional Patent Application No. 61/246,920, filed on Sep. 29, 2009. Each of these patent applications is herein incorporated by reference in their entirety.

This application also claims priority as a continuation-in-part of U.S. patent application Ser. No. 14/731,161, filed on Jun. 4, 2015, now U.S. Patent Application Publication No. 2015-0265405, which is a divisional application of U.S. patent application Ser. No. 12/893,832, filed Sep. 29, 2010, now. U.S. Pat. No. 9,078,660, which is a continuation-in-part of U.S. patent application Ser. No. 11/860,438, filed Sep. 24, 2007 (which issued as U.S. Pat. No. 7,897,086 on Mar. 1, 2011), which is a continuation-in-part of U.S. patent application Ser. No. 10/913,608, filed on Aug. 5, 2004, now abandoned. U.S. patent application Ser. No. 12/893,832 also claims priority as a continuation-in-part of U.S. patent application Ser. No. 12/509,289, filed on Jul. 24, 2009, now U.S. Pat. No. 8,398,537, which is a continuation of U.S. patent application Ser. No. 11/151,164, filed Jun. 10, 2005, now U.S. Pat. No. 7,582,051. U.S. patent application Ser. No. 12/893,832 also claims priority to U.S. Provisional Patent Application No. 61/246,920, filed on Sep. 29, 2009. Each of these patent applications is herein incorporated by reference in their entirety.

The devices and methods described herein may be applied to many of the devices and systems described in any of the references listed below. In particular, these references generally describe devices, systems, and methods for improving cardiac function and to ventricular partitioning devices in particular. Thus, the following patents/patent applications are herein incorporated by reference in their entirety: U.S. patent application Ser. No. 09/635,511, which is now abandoned, filed on Aug. 9, 2000 (titled "DEVICE AND METHOD FOR TREATMENT OF HOLLOW ORGANS"); U.S. patent application Ser. No. 10/212,032, which is now U.S. Pat. No. 7,279,007, filed on Aug. 1, 2002 (titled "METHOD FOR IMPROVING CARDIAC FUNCTION"); U.S. patent application Ser. No. 10/212,033, which is now U.S. Pat. No. 7,303,526 filed on Aug. 1, 2002 (titled "DEVICE FOR IMPROVING CARDIAC FUNCTION"); U.S. patent application Ser. No. 10/302,269, which is now abandoned, filed on Nov. 22, 2002 (titled "DEVICE WITH A POROUS MEMBRANE FOR IMPROVING CARDIAC FUNCTION"); U.S. patent application Ser. No. 10/302,272, which is now U.S. Pat. No. 7,887,477, filed on Nov. 22, 2002 (titled "METHOD OF IMPROVING CARDIAC FUNCTION USING A POROUS MEMBRANE"); U.S. patent application Ser. No. 10/382,962, which is now U.S. Pat. No. 6,852,076, filed on Mar. 6, 2003 (titled "METHOD FOR IMPROVING CARDIAC FUNCTION"); U.S. patent application Ser. No. 10/436,959, which is now U.S. Pat. No. 8,257,428, filed on May 12, 2003 (titled "SYSTEM FOR IMPROVING CARDIAC FUNCTION"); U.S. patent application Ser. No. 10/754,182, which is now U.S. Pat. No. 7,399,271, filed on Jan. 9, 2004 (titled "VENTRICULAR PARTITIONING DEVICE"); U.S. patent application Ser. No. 10/791,916, which is now U.S. Pat. No. 7,762,943, filed on Mar. 3, 2004 (titled "IN FLATABLE VENTRICULAR PARTITIONING DEVICE"); U.S. patent application Ser. No. 10/913,608, which is now abandoned, filed on Aug. 5, 2004 (titled "VENTRICULAR PARTITIONING DEVICE"); U.S. patent application Ser. No. 11/151,156, which is now U.S. Pat. No. 7,862,500, filed on Jun. 10, 2005 (titled "MULTIPLE PARTITIONING DEVICES FOR HEART TREATMENT"); U.S. patent application Ser. No. 11/151,164, which is now U.S. Pat. No. 7,582,051, filed on Jun. 10, 2005 (titled "PERIPHERAL SEAL FOR A VENTRICULAR PARTITIONING DEVICE"); U.S. patent application Ser. No. 11/199,633, which is now abandoned, filed on Aug. 9, 2005 (titled "METHOD FOR TREATING MYOCARDIAL RUPTURE"); U.S. patent application Ser. No. 11/640,469, which is now U.S. Pat. No. 7,674,222, filed on Dec. 14, 2006 (titled "CARDIAC DEVICE AND METHODS OF USE THEREOF"); U.S. patent application Ser. No. 11/800,998, which is now U.S. Pat. No. 8,747,454 filed on May 7, 2007 (titled "SYSTEM FOR IMPROVING CARDIAC FUNCTION"); U.S. patent application Ser. No. 11/801,075, which is now U.S. Pat. No. 8,657,873, filed on May 7, 2007 (titled "SYSTEM FOR IMPROVING CARDIAC FUNCTION"); U.S. patent application Ser. No. 11/860,438, which is now U.S. Pat. No. 7,897,086, filed on Sep. 24, 2007 (titled "LAMINAR VENTRICULAR PARTITIONING DEVICE"); U.S. patent application Ser. No. 12/125,015, which is now abandoned, filed on May 21, 2008 (titled "VENTRICULAR PARTITIONING DEVICE"); U.S. patent application Ser. No. 12/129,443, which is now U.S. Pat. No. 8,529,430, filed on May 29, 2008 (titled "THERAPEUTIC METHODS AND DEVICES FOLLOWING MYOCARDIAL INFARCTION"); U.S. patent application Ser. No. 12/181,282, which is now U.S. Pat. No. 7,976,455, filed on Jul. 28, 2008 (titled "INFLATABLE VENTRICULAR PARTITIONING DEVICE"); U.S. patent application Ser. No. 12/198,010, which is now U.S. Pat. No. 8,500,795, filed on Aug. 25, 2008 (titled "RETRIEVABLE DEVICES FOR IMPROVING CARDIAC FUNCTION"); U.S. patent application Ser. No. 12/198,022, which is now U.S. Pat. No. 8,246,671, filed on Aug. 25, 2008 (titled "RETRIEVABLE CARDIAC DEVICES"); and U.S. patent application Ser. No. 12/268,346, which is now U.S. Pat. No. 8,192,478, filed on Nov. 10, 2008 (titled "SYSTEM FOR IMPROVING CARDIAC FUNCTION").

INCORPORATION BY REFERENCE

All publications and patent applications mentioned in this specification are herein incorporated by reference in their entirety, as if each individual publication or patent application was specifically and individually indicated to be incorporated by reference in its entirety.

FIELD

The present invention relates generally to medical/surgical devices and methods pertaining to treating heart disease, particularly heart failure. More specifically, the present invention relates to devices and methods for delivering a partitioning device to a patient's ventricle.

BACKGROUND

Described herein are systems, methods and devices for improving cardiac function. The systems, methods, and devices described herein may relate generally to treating heart disease, particularly heart failure, and more specifically, to systems, methods, and devices for delivering a partitioning device to a patient's ventricle.

Heart failure annually leads to millions of hospital visits internationally. Heart failure is the description given to a myriad of symptoms that can be the result of the heart's inability to meet the body's demand for blood flow. In certain pathological conditions, the ventricles of the heart become ineffective in pumping the blood, causing a back-up of pressure in the vascular system behind the ventricle.

The reduced effectiveness of the heart is usually due to an enlargement of the heart. A myocardial ischemia may, for example, cause a portion of a myocardium of the heart to lose its ability to contract. Prolonged ischemia can lead to infarction of a portion of the myocardium (heart muscle) wherein the heart muscle dies and becomes scar tissue. Once this tissue dies, it no longer functions as a muscle and cannot contribute to the pumping action of the heart. When the heart tissue is no longer pumping effectively, that portion of the myocardium is said to be hypokinetic, meaning that it is less contractile than the uncompromised myocardial tissue. As this situation worsens, the local area of compromised myocardium may in fact bulge out as the heart contracts, further decreasing the heart's ability to move blood forward. When local wall motion moves in this way, it is said to be dyskinetic, or akinetic. The dyskinetic portion of the myocardium may stretch and eventually form an aneurysmic bulge. Certain diseases may cause a global dilated myopathy, i.e., a general enlargement of the heart when this situation continues for an extended period of time.

As the heart begins to fail, diastolic pressures increase, which stretches the ventricular chamber prior to contraction and greatly increases the pressure in the heart. In response, the heart tissue reforms to accommodate the chronically increased filling pressures, further increasing the work that the now compromised myocardium must perform.

A further example is congestive heart failure (CHF), characterized by a progressive enlargement of the heart, particularly the left ventricle. CHF is a major cause of death and disability in the United States and elsewhere. As a patient's heart enlarges, it pumps less efficiently and, in time, the heart becomes so enlarged that it cannot adequately supply blood to the body. The fraction of blood within the left ventricle that is pumped forward at each stroke, commonly referred to as the "ejection fraction", is typically about sixty percent for a healthy heart. A congestive heart failure patient typically has an ejection fraction of 40% or less, and as a consequence, is chronically fatigued, physically disabled, and burdened with pain and discomfort. Further, as the heart enlarges, heart valves lose the ability to close adequately. An incompetent mitral valve allows regurgitation of blood from the left ventricle back into the left atrium, further reducing the heart's ability to pump blood.

Congestive heart failure can result from a variety of conditions, including viral infections, incompetent heart valves, ischemic conditions in the heart wall, or a combination of these conditions. Prolonged ischemia and occlusion of coronary arteries can result in myocardial tissue in the ventricular wall dying and becoming scar tissue. Once a portion of myocardial tissue dies, that portion no longer contributes to the pumping action of the heart. As the disease progresses, a local area of compromised myocardium can bulge during the heart contractions, further decreasing the heart's ability to pump blood, and further reducing the ejection fraction.

In the early stages of heart failure, drug therapy is presently the most commonly prescribed treatment. Drug therapy typically treats the symptoms of the disease and may slow the progression of the disease, but it does not cure the disease. Presently, the only treatment considered curative for heart failure is heart transplantation, but these procedures are high risk, invasive, and costly. Further, there is a shortage of hearts available for transplant, many patients fail to meet transplant-recipient qualifying criteria.

Much effort has been directed toward the development of surgical and device-based treatments for heart failure. Surgical procedures have been developed to dissect and remove weakened portions of the ventricular wall in order to reduce heart volume. As is the case with heart transplant, these procedures are invasive, risky, and costly, and many patients do not qualify medically for the procedure. Other efforts to treat heart failure include the use of an elastic support placed around the heart to prevent further deleterious remodeling, and mechanical assist devices and completely mechanical hearts have been developed. Recently, improvements have been made in treating patients with heart failure by implanting pacing leads in both sides of the heart in order to coordinate the contraction of both ventricles of the heart. While these various procedures and devices have been found to be successful in providing some relief from heart failure symptoms and in slowing disease progression, none has been able to stop the course of the disease.

However, ventricular partitioning devices offer a solution for treating heart failure. These devices generally function to partition a patient's ventricle into a productive region and a non-productive region. For such devices to function properly, they are positioned in a specific location within the patient's heart chamber. Delivery of a partitioning device may be made complicated by the anatomy of a patient and by aspects or characteristics of the delivery device or partitioning device itself. Thus, it would be beneficial to provide devices, systems and methods for delivering and deploying a partitioning device in a patient's ventricle.

SUMMARY OF THE DISCLOSURE

The present invention relates to a ventricular partitioning device and a method of employing the device in the treatment of a patient with heart failure (HF). Embodiments of the device are adapted to span a chamber of the heart, typically the left ventricle, and partition the chamber into a main productive portion and a secondary non-productive portion. This partitioning reduces the total volume of the heart chamber, reduces the stress applied to the heart and, as a result, improves the blood ejection fraction thereof.

Embodiments of the device have a reinforced partitioning component with a concave, pressure-receiving surface which, in part, defines the main productive portion of the partitioned heart chamber when secured therein. The reinforced partitioning component preferably includes a hub and a membrane forming the pressure receiving surface. The partitioning component is reinforced by a radially expandable frame component formed of a plurality of ribs.

The ribs of the expandable frame have distal ends secured to the central hub and free proximal ends. The distal ends are preferably secured to the central hub to facilitate radial self expansion of the free proximal ends of the ribs away from a centerline axis. The distal ends of the ribs may be pivotally mounted to the hub and biased outwardly or fixed to the hub. The ribs may be formed of material such as superelastic NiTi alloy that permits compression of the free proximal ends of the ribs toward a centerline axis into a contracted configuration, and when released, allows for their self expansion to an expanded configuration.

The free proximal ends of the ribs are configured to engage and preferably penetrate the tissue lining a heart chamber, typically the left ventricle, to be partitioned so as to secure the peripheral edge of the partitioning component to the heart wall and to fix the partitioning component within the chamber so as to partition the chamber in a desired manner. The tissue-penetrating proximal tips are configured to penetrate the tissue lining at an angle approximately perpendicular to a centerline axis of the partitioning device. The tissue penetrating proximal tips of the ribs may be provided with attachments such as barbs or hooks that prevent withdrawal of the tips from the heart wall.

The ribs in their expanded configuration angle outwardly from the hub and the free proximal ends curve outwardly so that the membrane secured to the ribs of the expanded frame forms a trumpet-shaped, pressure receiving surface. The partitioning membrane in the expanded configuration has radial dimensions from about 10 to about 160 mm, preferably about 50 to about 100 mm, as measured from the centerline axis.

The partitioning device may be delivered percutaneously or intraoperatively. One particularly suitable delivery catheter has an elongated shaft, a releasable securing device on the distal end of the shaft for holding the partitioning device on the distal end, and an expandable member such as an inflatable balloon on a distal portion of the shaft proximal to the distal end to press the interior of the recess formed by the pressure-receiving surface to ensure that the tissue penetrating tips or elements on the periphery of the partitioning device penetrate sufficiently into the heart wall to hold the partitioning device in a desired position to effectively partition the heart chamber.

More particularly, the invention relates to an intracorporeal partitioning component that includes a frame with a plurality of ribs that is integrated with one or more sheets of fabric to form a unified unilaminar, bilaminar, or multilaminar structure, as well as methods for making the partitioning component. Embodiments of the invention thus include an intra partitioning component that includes a frame having a plurality of ribs with radially extending proximal ends and with distal ends secured to a hub; and a bilaminar sheet secured to the ribs of the frame by fused thermoplastic material within the bilaminar sheet of material. In some of these embodiments, the bilaminar sheet of material comprises expanded polytetrafluoroethylene (ePTFE). In some embodiments, the bilaminar sheet includes a porous material; in other embodiments the bilaminar sheet includes a non-porous material.

Embodiments of the invention further include an intracorporeal partitioning component that includes a frame having a plurality of ribs with radially extending proximal ends and with distal ends secured to a hub; and a single sheet secured to the ribs of the frame by fused thermoplastic material on one side of the sheet of material to form a unilaminar structure.

Embodiments of the invention also include an intracorporeal product that includes a first component configured for intracorporeal deployment, the component encased in thermoplastic material; and at least two sheets of ePTFE material secured to the first component by fused thermoplastic material therebetween to form at least a bilaminar sheet of ePTFE material.

Embodiments of the invention include a method of securing a polymeric sheet material to rib components of a frame structure, including disposing a tube comprising thermoplastic material over each of one or more rib components of the frame to form a thermoplastic-material-encased rib; forming an assembly by applying the thermoplastic-encased rib above a first sheet and a second sheet above the thermoplastic-encased rib; and heating the assembly to fuse the first and second sheets to the thermoplastic material to form a bilaminar sheet, the fusion occurring by the melting and reforming of the thermoplastic material between the sheets, the rib remaining within the melted and reformed thermoplastic material. These embodiments include methods wherein the first sheet and second sheet of material include ePTFE. In other embodiments, the first sheet and second sheet of material include a porous material. And in still other embodiments, the first sheet and second sheets of material may include a porous material, and the other of the first sheet and second sheets may include a nonporous material.

In some of these method embodiments, the heating includes exposure to a temperature of about 500 degrees F., and in some of these embodiments the heating occurs over a period of about 120 seconds. In some of these embodiments, the method further includes applying pressure to the assembly to fuse the thermoplastic material and the ePTFE sheets to the rib component, such applied pressure being between about 60 psi and about 90 psi. In some of these embodiments, pressure is applied for a period of about 120 seconds.

Some embodiments of the invention include a method of making an intracorporeal product, including: (a) providing two ePTFE sheets; (b) providing a rib component of a frame structure; (c) deploying a thermoplastic-material containing element over at least part of the rib component; (d) applying the ePTFE sheets to at least a portion of the rib component covered by the thermoplastic element, the rib component disposed between the sheets, to form an assembly; and (e) heating the assembly to fuse the thermoplastic material and the ePTFE sheets to the rib component, the ePTFE sheets thereby forming a bilaminar ePTFE sheet structure secured to the rib component. In various embodiments, the heating step includes exposure to a temperature ranging between about 260 degrees F. and about 530 degrees F. More particularly, the heating may include exposure to a temperature ranging between about 375 degrees F. and about 520 degrees F. Still more particularly, the heating may include exposure to a temperature ranging between about 490 degrees F. and about 510 degrees F. And in some embodiments, the heating may include exposure to a temperature of about 500 degrees F.

Some embodiments of the method of making an intracorporeal product further include applying pressure to the assembly to fuse the thermoplastic material and the ePTFE sheets to the rib component. In some of these embodiments, the pressure applied is between about 10 psi and about 150 psi. In some particular embodiments, the pressure applied is between about 35 psi and about 120 psi. And in some particular embodiments, the pressure applied is between about 60 psi and about 90 psi.

Some embodiments of the method of making an intracorporeal product include applying heat and pressure to the assembly for a predetermined period of time that ranges between about 30 seconds and about 360 seconds. In some embodiments, the period of time ranges between about 75 seconds and about 240 seconds. And in some particular embodiments, the period of time is about 120 seconds.

Some embodiments of the method of making an intracorporeal product the fusion of polyethylene material and polytetra-fluoro-ethylene (PTFE) material occurs by the polyethylene melting and intercalating into the ePTFE fabric, cooling, and reforming to create interlocking zones of material continuity between polyethylene and polytetrafluoroethylene (PTFE).

Some embodiments of the method of making an intracorporeal product include (a) providing one ePTFE sheet; (b) providing a rib component of a frame structure; (c) deploying a thermoplastic-material containing element over at least part of the rib component; (d) applying the ePTFE sheet to at least a portion of the rib component covered by the thermoplastic element, the rib component disposed adjacent to the sheet, to form an assembly; and (e) heating the assembly to fuse the thermoplastic material and the ePTFE sheets to the rib component, the ePTFE sheet thereby forming a unilaminar ePTFE sheet structure secured to the rib component.

Also described herein is a method of securing a polymeric sheet to rib components of a frame structure, wherein the rib components are jointed at a hub to form an expandable and collapsible implant. In general, the method may include the steps of disposing a tube comprising thermoplastic material over each of one or more rib components of the frame; forming an assembly by applying the thermoplastic-encased rib adjacent to at least one polymeric sheet of material; and heating the assembly to fuse the sheet to the thermoplastic material to form a fused sheet, the fusion occurring by the heating and reforming of the thermoplastic material to the sheet, the rib remaining within the reformed thermoplastic material, wherein the implant is adapted to span a left ventricle. In some embodiments, the method further includes the step applying pressure to the assembly to form a fused sheet.

In some embodiments, the disposing step may further include forming a thermoplastic-material-encased rib. In some embodiments, the disposing step may further include forming thermoplastic-material-encased ribs having proximal portions that are not encased in the thermoplastic material. In some embodiments, the disposing step may further include forming thermoplastic-material-encased ribs having tissue-penetrating proximal ends that are not encased in the thermoplastic material. In some embodiments, the disposing step may further include forming thermoplastic-material-encased ribs, wherein the thermoplastic material is disposed over a first portion of a first rib and a second portion of a second rib, wherein the first and second ribs are adjacent to one another and the first portion is at a different position along the length of the rib than the second portion.

In some embodiments, at least one polymeric sheet of material comprises ePTFE. In some embodiments, the fused sheet is a unilaminar sheet.

Also described herein are methods of securing a polymeric sheet to rib components of a frame structure, wherein the rib components are jointed at a hub to form an expandable and collapsible implant, wherein the implant is adapted to span a left ventricle. In general, the method includes the steps of providing an assembly, the assembly comprising a frame structure disposed between a first and second polymeric sheet; and heating the assembly under pressure to fuse the first polymeric sheet to the second polymeric sheet around the frame structure to form a fused sheet. In some embodiments, the first and second polymeric sheets comprise ePTFE.

Also described herein are methods for securing a polymeric sheet to rib components of a frame structure, wherein the rib components are jointed at a hub to form an expandable and collapsible implant. In general the method may include the steps of decreasing a diameter of the frame structure; placing the frame structure into an assembly fixture, wherein the assembly fixture is configured to hold the frame structure in a loaded configuration with a decreased diameter; placing a polymeric sheet into the assembly fixture; and heating the assembly under pressure to fuse the sheet to the frame structure.

In some embodiments, the method further includes the step of disposing a tube comprising thermoplastic material over each of one or more rib components of the frame. In some embodiments, the method further includes the step of forming an assembly by applying the thermoplastic-encased rib adjacent to at least one polymeric sheet of material. In some embodiments, the fusion occurs by the heating and reforming of the thermoplastic material to the sheet.

Also described herein is an assembly fixture for securing a polymeric sheet to rib components of a frame structure, wherein the rib components are jointed at a hub to form an expandable and collapsible implant. In general, the fixture may include a first platen having male shaping portion and a rim portion positioned around the periphery of the first platen; and a second platen having female shaping portion and a rim portion positioned around the periphery of the second platen; wherein the male and female shaping portions are configured to hold the rib components of the frame structure in a loaded configuration with a decreased diameter.

In some embodiments, the male and female shaping portions have complimentary curved shapes configured to hold the frame in a curved, loaded configuration with a decreased diameter.

In some embodiments, the two rim portions form complementary planar surfaces which serve to hold edges of the polymeric sheet. In some embodiments, the male and female shaping portions are further configured to press the polymeric sheet. In some embodiments, the polymeric sheet comprises ePTFE.

Described herein are systems, devices, and methods for partitioning a heart. The systems may include a partitioning device or implant, applicators for inserting, repositioning and/or removing them, and methods of positioning, deploying and removing them. The implants described herein are cardiac implants that may be inserted into a chamber of a patient's heart, particularly the left ventricle. The implant may support the heart wall, or in some variations the implant is a ventricular partitioning device for partitioning the ventricle into productive and non-productive regions, and/or for reducing the volume of the ventricle.

For example, the devices and systems described herein may include a delivery system (or insertion tools, such as a catheter and sheath/guide tool) and a ventricular partitioning device including a plurality of ribs, configured to expand within the patient's ventricle. The delivery system may include one or more catheters (e.g., a guide catheter, delivery catheter, etc.). In some embodiments, the systems described herein include an elongate catheter having an expandable member at the distal end of the delivery catheter configured to expand the ventricular partitioning device and a coupling element at the distal tip of the delivery catheter configured to couple the ventricular partitioning device to the delivery catheter.

Described herein are systems for reducing the volume of a patent's ventricle. The system may include a delivery device (or delivery system) as described in detail herein, as well as a ventricular partitioning device. Any combination of any of the delivery systems and partitioning devices described herein may be used.

For example, a system for delivering a ventricular partitioning device into a patient's ventricle and deploying the partitioning device to reduce the effective volume of the ventricle by expanding the partitioning device from a collapsed delivery configuration into an expanded deployed configuration, may include: an elongate delivery catheter having a proximal end and a distal end; an expansion member near the distal end of the delivery catheter and configured to expand a plurality of struts of the partitioning device by applying pressure to the collapsed partitioning device to open the partitioning device and secure it in the ventricle; and a coupling element distal to the expansion member and configured to deployably secure to a hub of the partitioning device to retain the expansion member at least partially surrounded by the collapsed partitioning device prior to deployment.

The system may further comprise an expansion control for expanding the expansion member to apply pressure and expand the ventricular partitioning device. Any appropriate expansion control may be used, including an inflation lumen connected to the expansion member, a pullwire for pulling on the expansion member to expand it, or the like. The expansion control may also include a manipulatable control, such as a button, knob, slider, or dial on the proximal end of the elongate delivery catheter for controlling expansion of the expansion member.

The system may also include a deployment control for releasing the coupling element from the hub of the ventricular partitioning device. Any appropriate deployment control may be used, including (but not limited to) a torque shaft connected to the coupling element for unscrewing the coupling element from the ventricular partitioning device, a pullwire connected to the coupling element for pulling a hitch pin to release the ventricular partitioning device, or the like.

The deployment control and the expansion control may be separately activated. In some variations, the expansion control may be repeatedly activated to expand/contract the partitioning device.

As mentioned, any of the systems described herein may also include a ventricular partitioning device. For example, a system may include a ventricular partitioning device comprising an umbrella-like structure having a plurality of struts joined at a central hub.

The catheter (e.g., delivery catheter) may include any appropriate expansion member. For example, the expansion member may be a hydraulic expansion member comprising a plurality of openings for releasing pressurized fluid to apply pressure to expand the ventricular partitioning device, an inflatable expansion member (e.g., a balloon), or a mechanical expander. A mechanical expansion member may include a plurality of struts joined at their proximal and distal ends and configured to expand outwards when the proximal and distal ends are brought closer together.

The catheter may also include any appropriate coupling element, including mechanical coupling members such as helical screws, hitch pins, or the like.

In some variations of the system, the delivery catheter further comprises a proximal handle having a one-handed activation release.

The systems described herein may also include a steering mechanism that bends the distal end region of the delivery catheter. The steering mechanism may include tendons or pull wires that pull one or more sides of the catheter to bend the catheter for steering. In some variations, described in greater detail below, the catheter is adapted to be steered by bending selectively in one or more directions. In some variations, the catheter includes hinge-points or cut-out regions that allow for column strength (allowing pushing/pulling of the catheter axially), while making the catheter flexible in one or more directions. The catheter may also be formed of multiple layers; for example, a guide catheter may include an outer catheter formed of a metal or other appropriate material providing column strength and having a lumen in which an inner catheter resides. The inner catheter may also include one or more lumen (e.g., an inflation lumen, a perfusion lumen, etc.). The catheter may also include a pullwire and/or a torque wire.

In one variation, a system for delivering a ventricular partitioning device into a patient's ventricle and deploying the partitioning device to reduce the effective volume of the ventricle by expanding the partitioning device from a collapsed delivery configuration into an expanded deployed configuration may include: an elongate delivery catheter having a proximal end and a distal end; an expansion member near the distal end of the delivery catheter and configured to expand the partitioning device by applying pressure to open the collapsed partitioning device and secure it in the ventricle; a coupling element distal to the expansion member and configured to deployably secure to a hub of the partitioning device to retain the expansion member at least partially surrounded by the collapsed partitioning device prior to deployment; an expansion control at the proximal end of the elongate delivery catheter for expanding the expansion member to apply pressure and expand the partitioning device; and a deployment control for releasing the partitioning device from the delivery catheter by separating the coupling element from the hub of the partitioning device.

As mentioned above, any of the systems described herein, including the system for delivery a partitioning device into a patient's ventricle and deploying the partitioning device, may include any of the features described. For example, the system may include an expansion control comprising an inflation lumen connected to the expansion member, a pullwire for pulling on the expansion member to expand it, etc. The system may also include controls such as a button, knob, slider, or dial on the proximal end of the elongate delivery catheter for controlling expansion of the expansion member.

Also described herein are delivery systems for delivering an umbrella-shaped ventricular partitioning device into a patient's ventricle and mechanically deploying the partitioning device to reduce the effective volume of the ventricle by expanding the partitioning device from a collapsed configuration into an expanded configuration. These systems may comprise: an elongate delivery catheter having a proximal end and a distal end; a mechanical expander near the distal end of the delivery catheter having a plurality of arms configured to extend outwards when operated to apply pressure to the partitioning device to open the partitioning device; and a coupling element distal to the expansion member and configured to deployably secure to a central hub of the partitioning device and to retain the expansion member at least partially surrounded by the collapsed partitioning device prior to deployment.

Also described herein are delivery systems for delivering an umbrella-shaped ventricular partitioning device into a patient's ventricle and deploying the partitioning device to reduce the effective volume of the ventricle by expanding the partitioning device from a collapsed configuration into an expanded configuration, the system comprising: an elongate delivery catheter having a proximal end and a distal end; a mechanical expander near the distal end of the delivery catheter comprising a plurality of arms joined at their proximal and distal ends and configured to expand outwards when the proximal and distal ends are brought closer together, the mechanical expander configured to apply pressure to the partitioning device to open the partitioning device and secure it in the ventricle; and a coupling element distal to the expansion member and configured to deployably secure to a hub of the partitioning device and to retain the expansion member at least partially surrounded by the collapsed partitioning device prior to deployment.

In some variations, a delivery system for delivering an umbrella-shaped ventricular partitioning device into a patient's ventricle and deploying the partitioning device to reduce the effective volume of the ventricle by expanding the partitioning device from a collapsed configuration into an expanded configuration, includes: an elongate delivery catheter having a proximal end and a distal end; an inflatable expander near the distal end of the delivery catheter configured to extend outwards when inflated to apply pressure to open the partitioning device and to secure the partitioning device in the ventricle; a distal nose spacer distal to the inflatable expander on the delivery catheter and configured to space the inflatable expander proximally from a central hub region of the partitioning device; a taper region between the distal nose spacer and the inflatable expander; and a coupling element distal to the expansion member and configured to deployably secure to the central hub of the partitioning device and to retain the expansion member at least partially surrounded by the partitioning device prior to deployment.

Also described herein are delivery systems for delivering an umbrella-shaped ventricular partitioning device into a patient's ventricle and mechanically deploying the partitioning device to reduce the effective volume of the ventricle by expanding the partitioning device from a collapsed configuration into an expanded configuration, the system comprising: an elongate delivery catheter having a proximal end and a distal end; a pressure expander near the distal end of the delivery catheter comprising a plurality of openings from a fluid source line extending along the length of the elongate delivery catheter, the plurality of openings positioned near the distal end region of the elongate delivery catheter and configured to release fluid and apply pressure to the proximal end region of the partitioning device to expand the partitioning device; and a coupling element distal to the expansion member and configured to deployably secure to a central hub of the partitioning device and to retain the expansion member at least partially surrounded by the partitioning device prior to deployment.

Also described are systems for reducing the effective volume of the ventricle by securing a ventricular partitioning device within the ventricle, the system comprising: an umbrella-shaped ventricular partitioning device having a central hub, a plurality of struts, and a membrane, wherein the partitioning device has a collapsed delivery configuration and an expanded deployed configuration; and a delivery system. The delivery system may include: an elongate delivery catheter having a proximal end and a distal end; a mechanical expander near the distal end of the delivery catheter comprising a plurality of arms configured to extend outwards to expand the ventricular partitioning device by applying pressure against the struts to open the ventricular partitioning device; a expansion pullwire coupled to the mechanical expander; and a coupling element distal to the expansion member and configured to deployably secure to the central hub of the partitioning device and to retain the expansion member at least partially surrounded by the collapsed partitioning device prior to deployment.

Methods of partitioning a ventricle, and method of reducing ventricular volume, are also described. The methods described herein may generally include the steps of advancing the distal end of a delivery or guide catheter into the patient's ventricle, positioning the distal end of the delivery catheter within the ventricle, expanding a ventricular partitioning device within the ventricle to partition the ventricle, and deploying the ventricular partitioning device from the distal end of the delivery catheter. The device may be secured, and/or sealed, to the ventricle wall(s).

For example, described herein are methods of reducing ventricular volume to treat heart disease, the method comprising: positioning an umbrella-shaped, expandable partitioning device having a reinforced membrane in a contracted configuration near the apex of a patients' ventricle using an elongate delivery catheter to which the partitioning device is releasably coupled; expanding an expansion member near the distal end of the delivery catheter to apply pressure to the proximal end region of the contracted partitioning device to expand the partitioning device; and releasing a coupling element distal to the expansion member on the delivery catheter to deploy the partitioning device.

In some variations, the method also includes a step of securing the periphery of the partitioning device to the ventricle wall. For example, the delivery catheter may be configured to expand to drive open the partitioning device and secure it to the wall of the ventricle. The method may also include the step of sealing the periphery of the partitioning device to the ventricle wall.

In some variations, the method also includes percutaneously guiding the partitioning device on the end of the delivery catheter into the ventricle. For example, the method may include advancing the partitioning device into the ventricle through an inner lumen of a delivery catheter.

The method may include the step of expanding the expansion member by expanding an inflatable expansion member near the distal end of the delivery catheter. The step of expanding the expansion member may comprise expanding a plurality of arms joined at their proximal and distal ends by bringing the proximal and distal ends closer together. In some variations, the step of expanding the expansion member comprises expelling fluid from a plurality of openings positioned near the distal end region of the delivery catheter to apply pressure to the proximal end region of the partitioning device to expand the partitioning device.

The step of releasing a partitioning device from the catheter (delivery catheter that has guided and positioned the device) may be performed after the device has been positioned in the appropriate region of the ventricle, typically the apical region. This guidance may be performed under visualization, such as fluoroscopy. Once positioned, the device may be deployed and released from the catheter by disengaging the coupling member. For example, the coupling element may be released by rotating a torque shaft that rotates to withdraw a helical coil screw (e.g., the screw and torque shaft may form part of the coupling element) from a hub of the partitioning device.

Also described are delivery systems for transvascular delivery of a ventricular partitioning device into a patient's ventricle and deploying the partitioning device to reduce the effective volume of the ventricle by expanding the partitioning device from a collapsed delivery configuration into an expanded deployed configuration. In general, the delivery systems may include an elongate guide catheter having a proximal end and a distal end; a conical dilator at the distal end of the elongate guide catheter, the conical dilator being removable to enable delivery of the ventricular partitioning device; a delivery catheter having a proximal end and a distal end; an expansion member near the distal end of the delivery catheter and configured to expand a plurality of struts of the partitioning device by applying pressure to the collapsed partitioning device to open the partitioning device and secure it in the ventricle; a coupling element configured to deployably secure to a hub of the partitioning device to retain the expansion member at least partially surrounded by the collapsed partitioning device prior to deployment. In some embodiments, the expansion member is an inflatable balloon. In some embodiments, the coupling element comprises a helical screw.

In some embodiments, the delivery system may further include a ventricular partitioning device wherein the ventricular partitioning device comprises an umbrella-like structure having a plurality of struts joined at a central hub. In some embodiments, the central hub is coupled to the coupling element such that the central hub is distal to the plurality of struts. In some embodiments, the partitioning device has a central axis of symmetry. In some embodiments, the partitioning device has an asymmetric configuration around the hub.

In some embodiments, the delivery system may further include a steering mechanism that bends the distal end region of the guide catheter. In some embodiments, the delivery catheter is steerable. In some embodiments, the delivery system may further include at least one radio-opaque marker. In some embodiments, the delivery system may further include a guidewire lumen. In some embodiments, the guidewire lumen is continuous through the length of the delivery system. In some embodiments, the guidewire lumen is configured as a rapid-exchange feature. In some embodiments, the delivery system may further include a guidewire. In some embodiments, the guidewire includes a distal tip with an anchoring mechanism for anchoring to a cardiac wall.

Also described herein are methods for reducing ventricular volume to treat heart disease. In general the methods may include the steps of positioning an umbrella-shaped, expandable partitioning device having a reinforced membrane in a contracted configuration near the apex of a patients' ventricle using an elongate delivery catheter to which the partitioning device is releasably coupled; expanding an expansion member near the distal end of the delivery catheter to apply pressure to the proximal end region of the contracted partitioning device to expand the partitioning device; and releasing a coupling element distal to the expansion member on the delivery catheter to deploy the partitioning device.

In some embodiments, the methods may further include the step of securing the periphery of the partitioning device to the ventricle wall. In some embodiments, the methods may further include the step of percutaneously delivering the partitioning device on the end of the delivery catheter into the ventricle. In some embodiments, the methods may further include the step of advancing the partitioning device into the ventricle through an inner lumen of a delivery catheter.

In some embodiments, the step of expanding the expansion member comprises expanding an inflatable expansion member near the distal end of the delivery catheter. In some embodiments, the step of releasing comprises rotating a torque shaft to withdraw a helical coil screw from a hub of the partitioning device.

In some embodiments, the methods may further include the step of positioning the delivery system using a guidewire. In some embodiments, the step of positioning the delivery system using a guidewire further comprises positioning the delivery system over a guidewire. In some embodiments, the guidewire is anchored to an intended landing zone on the patient's ventricle.

In some embodiments, the patient's ventricle is obtained using a vascular conduit as an access route. In some embodiments, the vascular conduit is part of an arterial circulation. In some embodiments, the vascular conduit is part of a venous circulation, and the access route comprises a transseptal passage. In some embodiments, the transseptal passage is an inter-atrial passage through a foramen ovale.

Also described herein are delivery systems for transapical delivery of a ventricular partitioning device into a patient's ventricle and deploying the partitioning device to reduce the effective volume of the ventricle by expanding the partitioning device from a collapsed delivery configuration into an expanded deployed configuration. In general the systems include an elongate access sheath having a proximal end and a distal end; an elongate delivery catheter having a proximal and distal end; an expansion member near the distal end of the delivery catheter and configured to expand a plurality of struts of the partitioning device by applying pressure to the collapsed partitioning device to open the partitioning device and secure it in the ventricle; and a coupling element proximal to the expansion member and configured to deployably secure to a hub of the partitioning device to retain the expansion member at least partially surrounded by the collapsed partitioning device prior to deployment.

In some embodiments, the partitioning device has a central axis of symmetry; while in some embodiments, the partitioning device has an asymmetric configuration around the hub. In some embodiments, the elongate delivery catheter is a delivery shaft. In some embodiments, the delivery shaft is rigid.

In some embodiments, the delivery system further includes a ventricular partitioning device wherein the ventricular partitioning device comprises an umbrella-like structure having a plurality of struts joined at a central hub. In some embodiments, the central hub is coupled to the elongate delivery catheter such that the central hub is proximal to the plurality of struts. In some embodiments, the expansion member is an inflatable balloon. In some embodiments, the coupling element comprises a helical screw.

Also described herein is a transapical method of reducing ventricular volume to treat heart disease. In general, the method may include the steps of positioning an umbrella-shaped, expandable partitioning device having a reinforced membrane in a contracted configuration near the apex of a patient's ventricle using an elongate access sheath to which the partitioning device is releasably coupled; expanding an expansion member to apply pressure to the proximal end region of the contracted partitioning device to expand the partitioning device; and releasing a coupling element proximal to the expansion member to deploy the partitioning device. In some embodiments, the positioning step further comprises accessing the patient's ventricle through the apex of the patient's heart. In some embodiments, the method may further include the step of creating a cardiotomy near the apex of the patient's heart. In some embodiments, the method may further include the step of accessing the patient's heart through an intercostal access route. In some embodiments, the accessing step further comprises accessing the patient's heart percutaneously, while in some embodiments, the accessing step further comprises accessing the patient's heart surgically.

In some embodiments, the method may further include the step of pulling a delivery sheath in the proximal direction to release the partitioning device. In some embodiments, the method may further include the step of pushing a delivery sheath in the distal direction over the partitioning device to collapse the partitioning device for removal or redeployment.

BRIEF DESCRIPTION OF THE DRAWINGS

FIG. 22 illustrates one embodiment of a mechanical expansion member in a resting configuration.

FIG. 23 illustrates one embodiment of a mechanical expansion member in a resting configuration.

FIG. 24 illustrates one embodiment of a mechanical expansion member in resting configuration.

FIG. 25 illustrates one embodiment of a mechanical expansion member in resting configuration.

FIGS. 26A and 26B illustrate one embodiment of the delivery system including a mechanical expansion member.

FIG. 27 illustrates one embodiment of the delivery system including the frame and the delivery catheter formed from a single tube.

FIGS. 28A and 28B illustrate one embodiment of the delivery system including the frame and the delivery catheter formed from a single tube.

FIGS. 41A and 41B illustrates a delivery device configured for a transvascular approach and a transapical approach, respectively, embodying features of the invention, including at least one marker band.

FIG. 51A shows an exploded and partially cutaway view of the components of the device assembled for lamination; FIG. 51B provides of cutaway view of the device within a press, the press in a closed position; FIG. 51C shows a perspective view of an exemplary device; FIG. 51D provides a frontal view of the device after assembly.

FIG. 52A shows an exploded and partially cutaway view of the components of the device assembled for lamination; FIG. 52B provides of cutaway view of the device within the press in a closed position; FIG. 52C shows a perspective view of an exemplary device; and FIG. 52D provides a frontal view of the device after assembly.

FIG. 53A shows a polyethylene-encased rib sandwiched between two sheets of ePTFE material as assembled prior to processing in a mold or press. In this embodiment, the rib is substantially cylindrical in form, or substantially circular in cross section. FIG. 53B shows the same materials after the application of heat and pressure, to form a bilaminar sheet, the sheets held together by melted and reformed polyethylene material to which they are both fused, a rib disposed within and adherent to the polyethylene.

FIG. 54A shows a polyethylene-encased rib sandwiched between two sheets of ePTFE material as assembled prior to processing in a mold or press. In this embodiment, the rib is substantially rectangular, but curved in cross section. FIG. 54B shows the same materials after the application of heat and pressure, to form a bilaminar sheet, the sheets held together by melted and reformed polyethylene material to which they are both fused, a rib disposed within and adherent to the polyethylene.

FIG. 55A shows a polyethylene-encased rib overlaying a sheet of ePTFE material as assembled prior to processing in a mold or press. In this embodiment, the rib is substantially circular in cross section. FIG. 55B shows the same materials after the application of heat and pressure, to form a unilaminar sheet fused to a rib by the melted and reformed polyethylene, the polyethylene interposed between the rib and the ePTFE sheet, adhering to both.

FIG. 56A shows a polyethylene-encased rib overlaying a sheet of ePTFE material as assembled prior to processing in a mold or press. In this embodiment, the rib is substantially rectangular but curved in cross section. FIG. 56B shows the same materials after the application of heat and pressure, to form a unilaminar sheet fused to a rib by the melted and reformed polyethylene, the polyethylene interposed between the rib and the ePTFE sheet, adhering to both.

FIG. 59 shows an exploded and partially cutaway view of the components of an assembly for lamination of an intracorporeal partitioning device.

FIGS. 60A and 60B show an assembled device as a result of an assembly for lamination of an intracorporeal partitioning device.

DETAILED DESCRIPTION

Systems and Devices

Figure 1:
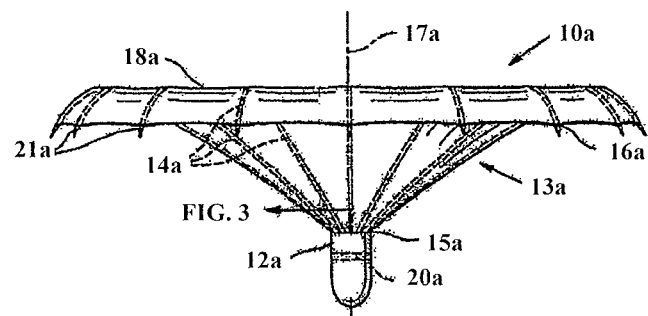
FIG. 1 is an elevational view of a partitioning device embodying features of the invention in an expanded configuration.

FIGS. 1-4 illustrate a partitioning component 10*a* which embodies features of the invention and which includes a partitioning membrane 11*a*, a hub 12*a*, preferably centrally located on the partitioning device, and a radially expandable reinforcing frame 13*a* formed of a plurality of ribs 14*a*. Embodiments of the partitioning component 10*a* may be alternatively referred to as an intracorporeal partitioning component or an intracorporeal product, referring to its position within a ventricle of the heart, and to its function in partitioning the ventricle. Preferably, the partitioning membrane 11*a* is secured to the proximal or pressure side of the frame 13*a* as shown in FIG. 1. The ribs of the intracorporeal device 14*a* have distal ends 15*a* which are secured to the hub 12*a* and free proximal ends 16*a* which are configured to curve or flare away from a center line axis 17*a*. Radial expansion of the free proximal ends 16*a* unfurls the membrane 11*a* secured to the frame 13*a* so that the membrane presents a relatively smooth, pressure receiving surface 18*a* which defines in part the productive portion of the patient's partitioned heart chamber.

Figure 3:
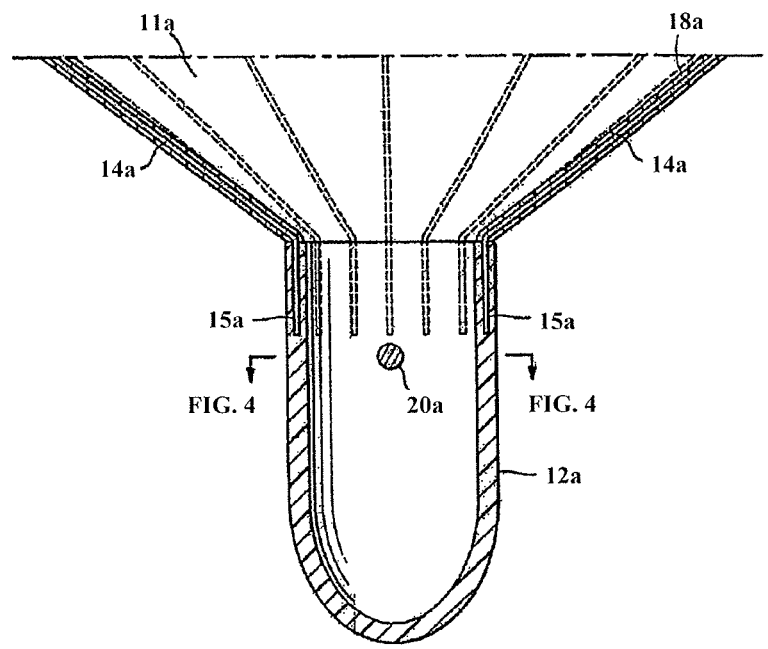
FIG. 3 is a partial longitudinal cross-sectional view of the hub of the partitioning device shown in FIG. 1.
Figure 4:
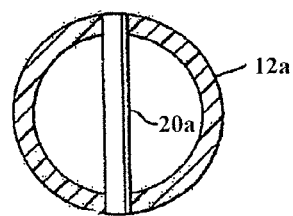
FIG. 4 is a transverse cross sectional view of the hub shown in FIG. 3 taken along the lines 4-4.

As shown in more detail in FIGS. 3 and 4, the distal ends 15*a* of the ribs 14*a* are secured within the hub 12*a* and a transversely disposed connector bar 20*a* is secured within the hub which is configured to secure the hub 12*a* and thus the partitioning component 10*a* to a delivery system such as shown in FIGS. 5A-5C and 6*a*. The curved free proximal ends 16*a* of ribs 14*a* are provided with sharp tip elements 21*a* which are configured to hold the frame 13*a* and the membrane 11*a* secured thereto in a deployed position within the patient's heart chamber. Preferably, the sharp tip elements 21*a* of the frame 13*a* penetrate into tissue of the patient's heart wall in order to secure the partitioning component 10*a* within the heart chamber so as to partition the ventricular chamber into a productive portion and a non-productive portion.

Figure 7:
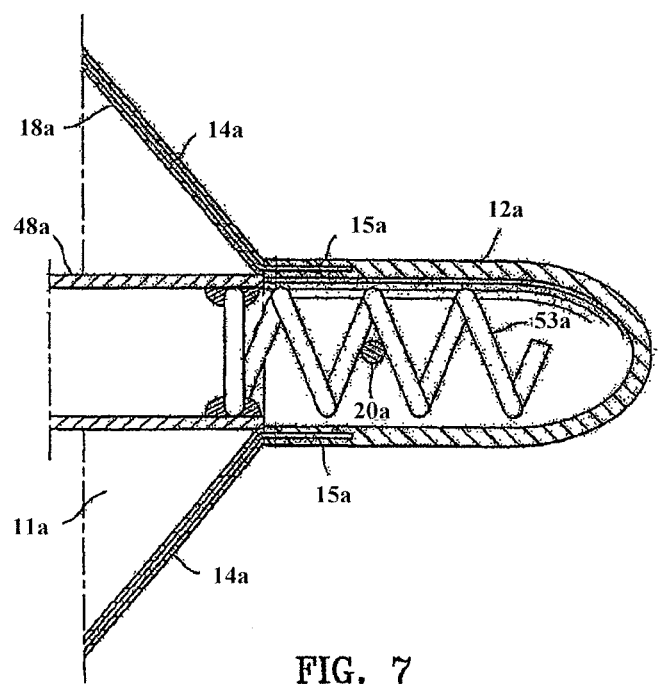
FIG. 7 is an elevational view, partially in section, of the hub shown in FIG. 3 secured to the helical coil of the delivery system shown in FIG. 5B.

The connector bar 20*a* of the hub 12*a*, as shown in FIGS. 4 and 7, allows the partitioning device 10*a* to be secured to a delivery system and to be released from the delivery system within the patient's heart chamber. The distal ends 15*a* of the reinforcing ribs 14*a* are secured within the hub 12*a* in a suitable manner or they may be secured to the surface defining the inner lumen or they may be disposed within channels or bores in the wall of the hub 12*a*. The ribs 14*a* are pre-shaped so that when not constrained other than by the membrane 11*a* secured thereto (as shown in FIGS. 1 and 2), the free proximal ends 16*a* thereof expand to a desired angular displacement away from a center line axis 17*a* which is about 20 degrees to about 90 degrees, preferably about 50 degrees to about 80 degrees.

Figure 2:
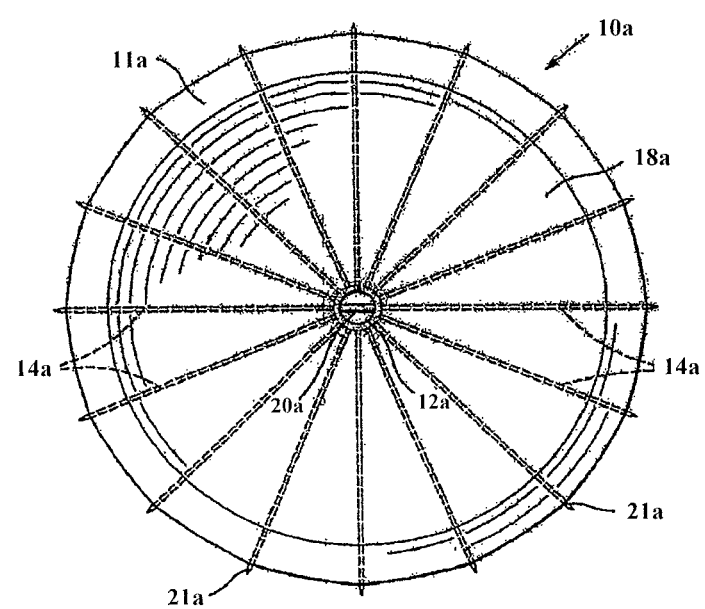
FIG. 2 is a plan view of the partitioning device shown in FIG. 1.
Figure 5A:
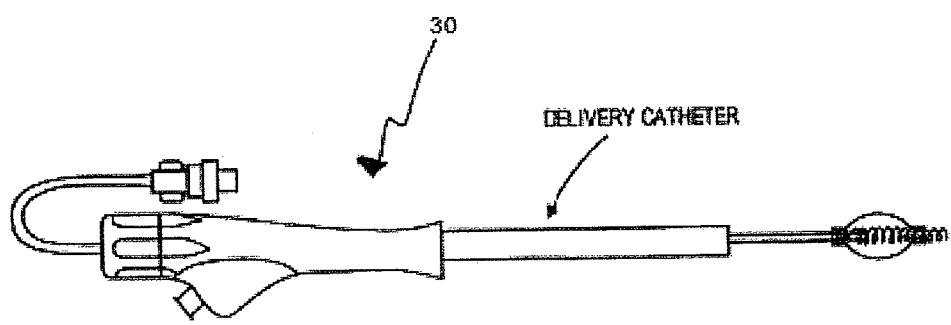
FIG. 5A illustrates a system for reducing ventricular volume including a delivery system (delivery catheter).
Figure 5B:
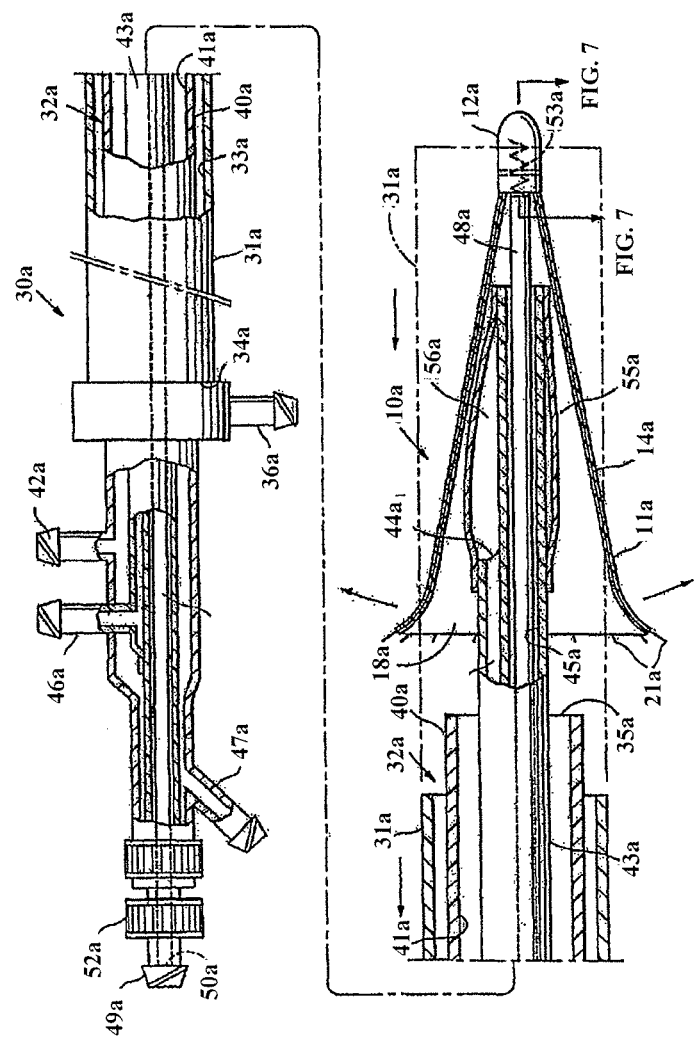
FIG. 5B is a schematic elevational view of a delivery system for the partitioning device shown in FIGS. 1 and 2.
Figure 5C:
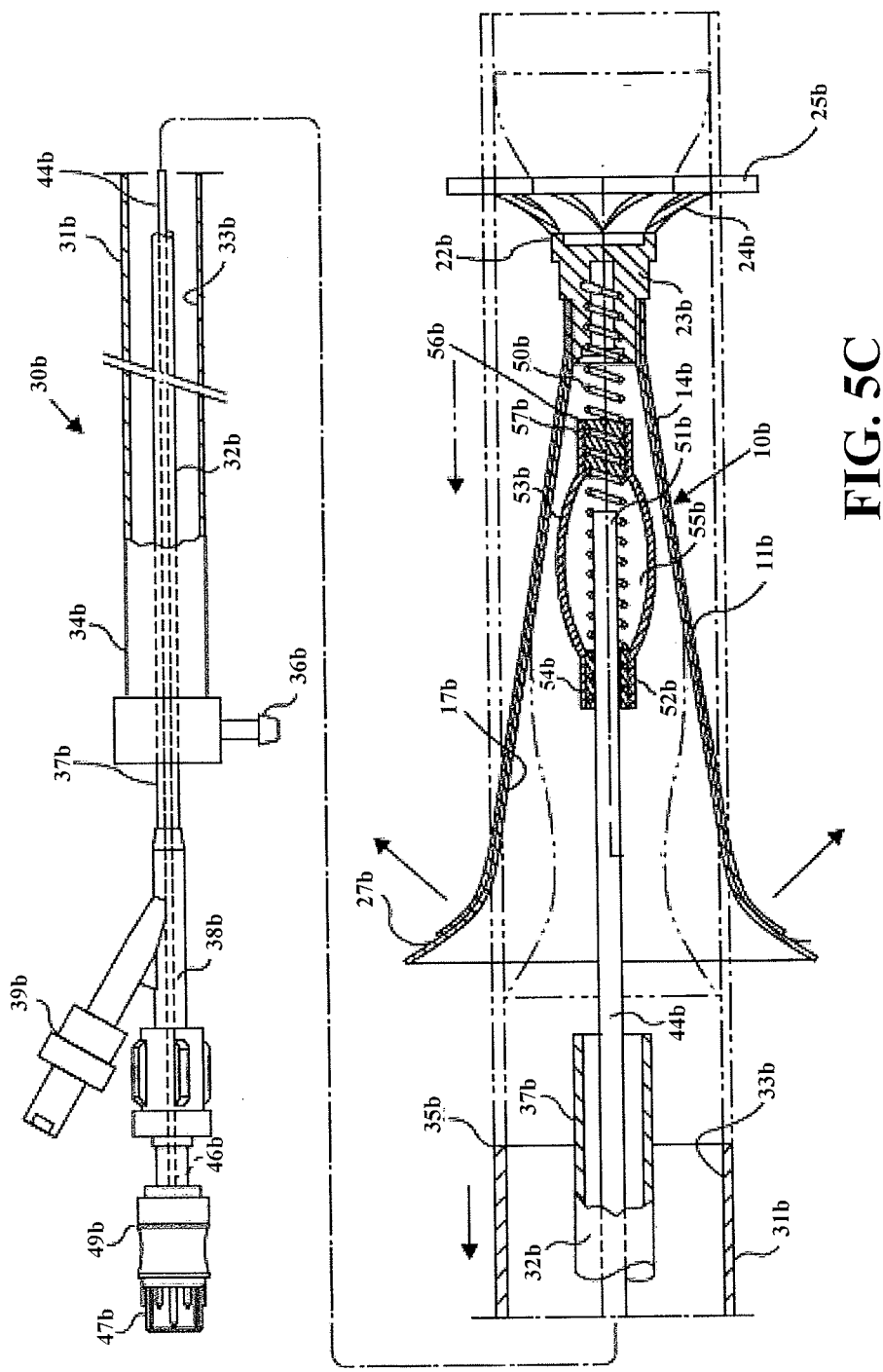
FIG. 5C shows another variation of a system for reducing ventricular volume including a partitioning device.
Figure 6:
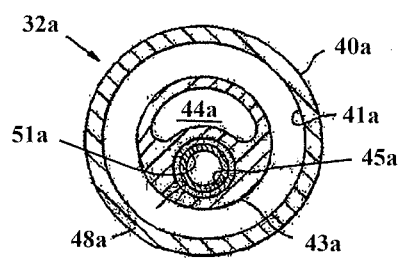
FIG. 6 is a transverse cross-sectional view of the delivery system shown in FIG. 5B taken along the lines 6-6.

FIGS. 5A-7 illustrate a suitable delivery system 30 delivering the partitioning component 10*a*, 10*b* shown in FIGS. 1 and 2 into a patient's heart chamber and deploying the partitioning component 10*a*, 10*b* to partition the heart chamber as shown in FIGS. 8A-8E and FIG. 9. The delivery system 30*a*, 30*b* includes a guide catheter 31*a*, 31*b* and a delivery catheter 32*a*, 32*b*. A transverse, cross-sectional view of delivery catheter 32*a* is shown in FIG. 6.

As shown in FIG. 5B, the guide catheter has an inner lumen 33*a* extending between the proximal end 34*a* and distal end 35*a*. A hemostatic valve (not shown) may be provided at the proximal end 34*a* of the guide catheter 31*a*. A flush port 36*a* on the proximal end 34*a* of guide catheter 31*a* is in fluid communication with the inner lumen 33*a*.

Further, as shown in FIGS. 5B and 6, the delivery catheter 32*a* has an outer shaft 40*a* with an inner lumen 41*a* and a proximal injection port 42*a*, an inner shaft 43*a* disposed within the inner lumen 41*a* with a first lumen 44*a* and a second lumen 45*a*. Balloon inflation port 46*a* is in fluid communication with the first lumen 44*a* and flush port 47*a* is in fluid communication with the second lumen 45*a*. Torque shaft 48*a* is rotatably disposed within the second lumen 44*a* of the inner shaft 43*a* and has an injection port 49*a* provided at its proximal end 50*a* in fluid communication with the inner lumen 51*a* of the torque shaft. The torque shaft 48*a* is preferably formed at least in part of a hypotube formed of suitable material such as superelastic Nitinol or stainless steel. A torque knob 52*a* is secured to the proximal end 50*a* of torque shaft 48*a* distal to the injection port 49*a*. As shown in FIGS. 5B and 7, A helical coil screw 53*a* is secured to the distal end of the torque shaft 48*a* and rotation of the torque knob 52*a* on the proximal end 50*a* of the torque shaft 48*a* rotates the screw 53*a* on the distal end of torque shaft 48*a* to facilitate deployment of a partitioning device 10*a*. An inflatable balloon 55*a* is sealingly secured to the distal end of the inner shaft 43*a* and has an interior 56*a* in fluid communication with the first lumen 44*a*. Inflation fluid may be delivered to the interior 56*a* through port 44*a* in the portion of the inner shaft 43*a* extending through the balloon 55*a*. Inflation of the balloon 55*a* by inflation fluid through port 46*a* facilitates securing the partitioning component 10*a*.

To deliver the partitioning component 10*a*, as shown in FIGS. 8A-8E, the partitioning component 10*a* is secured to the distal end of the delivery catheter 32*a* by means of the helical coil screw 53*a*. The partitioning component 10*a* is collapsed to a first, delivery configuration which has small enough transverse dimensions to be slidably advanced through the inner lumen 33*a* of the guide catheter 31*a*. Preferably, the guide catheter 31*a* has been previously percutaneously introduced and advanced through the patient's vasculature, such as the femoral artery, in a conventional manner to the desired heart chamber. The delivery catheter 32*a* with the partitioning component 10*a* attached is advanced through the inner lumen 33*a* of the guide catheter 31*a* until the partitioning component 10*a* is ready for deployment from the distal end of the guide catheter 31*a* into the patient's heart chamber 57*a* to be partitioned, as shown in FIGS. 8A-8E.

FIG. 5C illustrates another variation of a system 30*b* for delivering a partitioning device 10*b*. Although the embodiments of the delivery systems show in various embodiments may be different, common features are labeled similarly.

The delivery system 30*b* includes a guide catheter 31*b* and a delivery catheter 32*b*. As in the variation shown in FIG. 5B, the guide catheter 31*b* has an inner lumen 33*b* extending between the proximal end 34*b* and distal end 35*b*. A hemostatic valve (not shown) may be provided at the proximal end 34*b* of the guide catheter 31*b* to seal about the outer shaft 37*b* of the delivery catheter 32*b*. A flush port 36*b* on the proximal end 34*b* of guide catheter 31*b* is in fluid communication with the inner lumen 33*b*.

Figure 9:
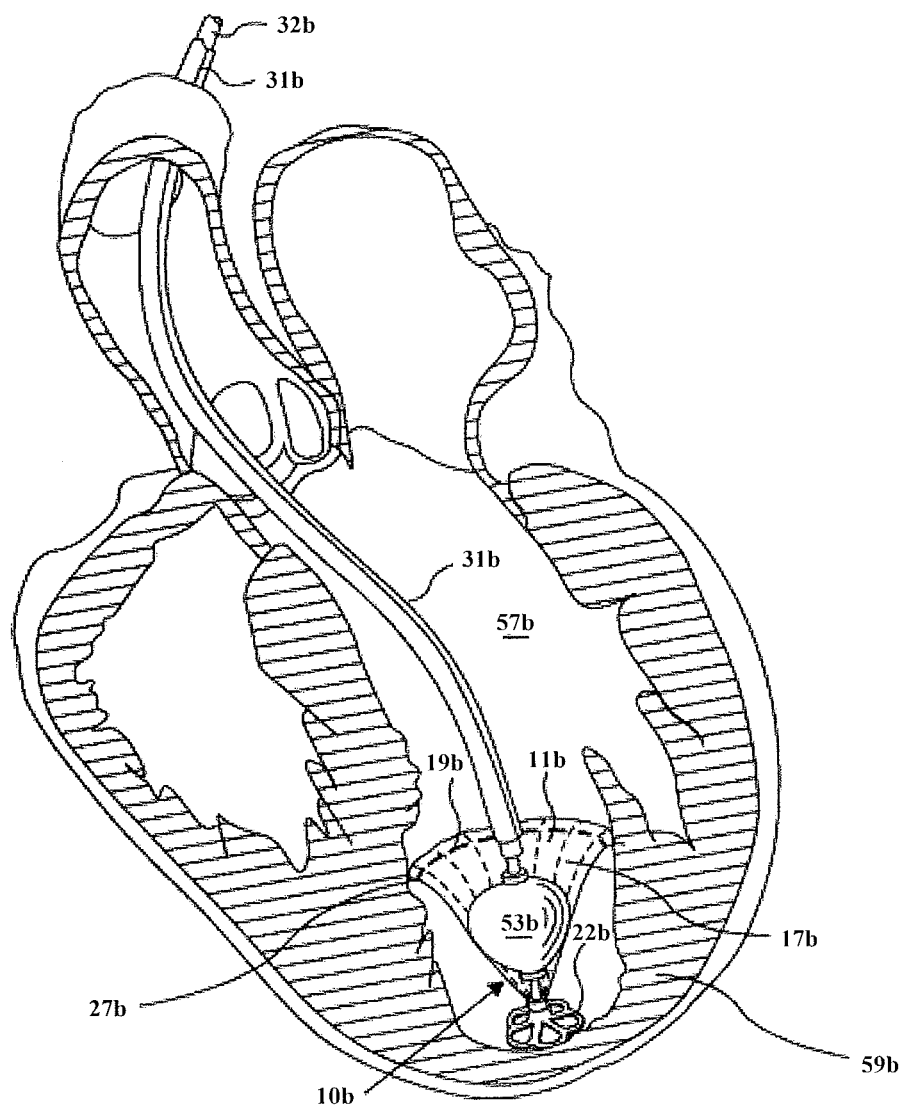
FIG. 9 illustrates deployment of the partitioning device shown in FIG. 5C.

The delivery catheter 32*b* has an outer shaft 37*b* with an adapter 38*b* on the proximal end thereof having a proximal injection port 39*b* which is in fluid communication with the interior of the shaft 37*b*. The outer shaft 37*b* may have an inner shaft which is disposed within the interior thereof and is secured to the inner surface of the outer shaft by webs which extend along a substantial length of the inner shaft. The injection port may be in fluid communication with the passageways between the inner and outer shafts and defined in part by the webs. A torque shaft, which is preferably formed of hypotubing (e.g. formed of stainless steel or superelastic NiTi), may be disposed within the inner lumen of the inner shaft and has a proximal end 46*b* secured within the adapter 38*b*. Balloon inflation port 47*b* is in fluid communication with the inner lumen of the torque shaft 44*b*. Torque shaft 44*b* is rotatably disposed within the inner lumen 45*b* of the inner shaft 41*b* and is secured to rotating knob 49*b*. A helical coil screw 50*b* is secured to the distal end 51*b* of the torque shaft 44*b* and rotation of the torque knob 49*b* on the proximal end 46*b* of the torque shaft 44*b* rotates the screw 51*b* to facilitate deployment of a partitioning device 10*b*. The proximal end 52*b* of inflatable balloon 53*b* is sealingly secured by adhesive 54*b* about the torque shaft 44*b* proximal to the distal end 51*b* of the torque shaft 44*b*. The balloon 53*b* has an interior 55*b* in fluid communication with the inner lumen 48*b* of the torque shaft 44*b*. Inflation fluid may be delivered to the balloon interior 55*b* through port 47*b* which is in fluid communication with the inner lumen 48*a* (shown in FIG. 5B) of the torque shaft 44*b*. The distal end 56*b* of the balloon 53*b* is sealingly secured by adhesive 57*b* to the helical screw 50*b*. The proximal and distal ends 52*b* and 56*b* of the balloon 53*b* are blocked by the adhesive masses 54*b* and 57*b* to prevent the loss of inflation fluid delivered to the interior 55*b* of the balloon 53*b*. Delivery of inflation fluid through a fluid discharge port 58*b* in the distal end 51*b* of the torque shaft 44*b* inflates the balloon 53*b* which in turn applies pressure to the proximal surface of the partitioning device 10*b* to facilitate securing the partitioning component 10*b* to the wall 59*b* of a heart chamber 57b, as shown in FIG. 9. The device may be inserted substantially as shown in FIG. 9 as described elsewhere herein.

Figure 8A:
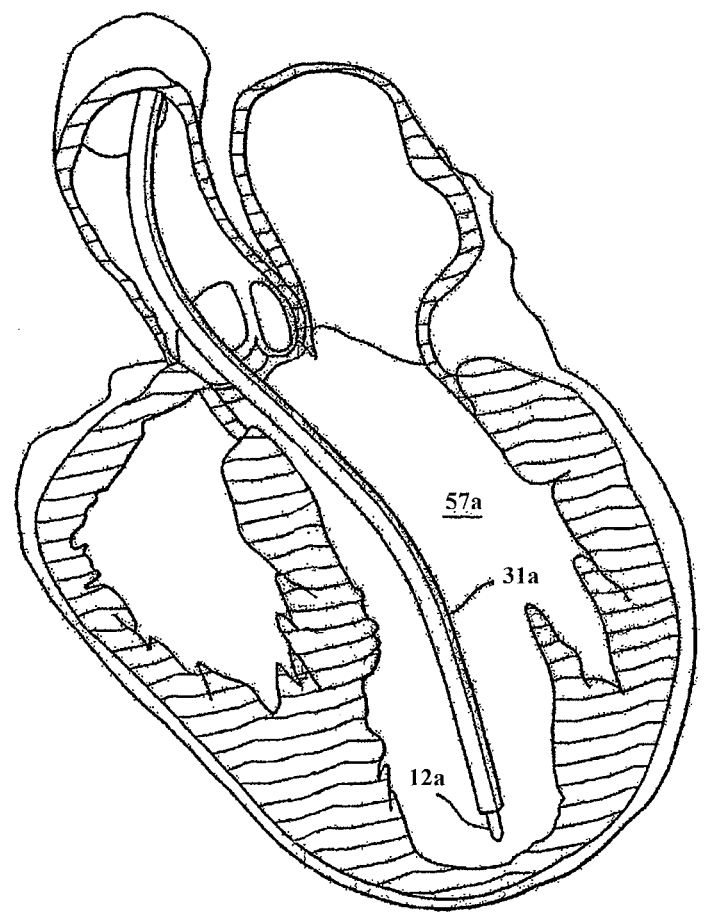
FIGS. 8A-8E are schematic views of a patient's left ventricular chamber illustrating the deployment of the partitioning device shown in FIGS. 1 and 2 with the delivery system shown in FIG. 5B to partition the heart chamber into a primary productive portion and a secondary, non-productive portion.
Figure 8B:
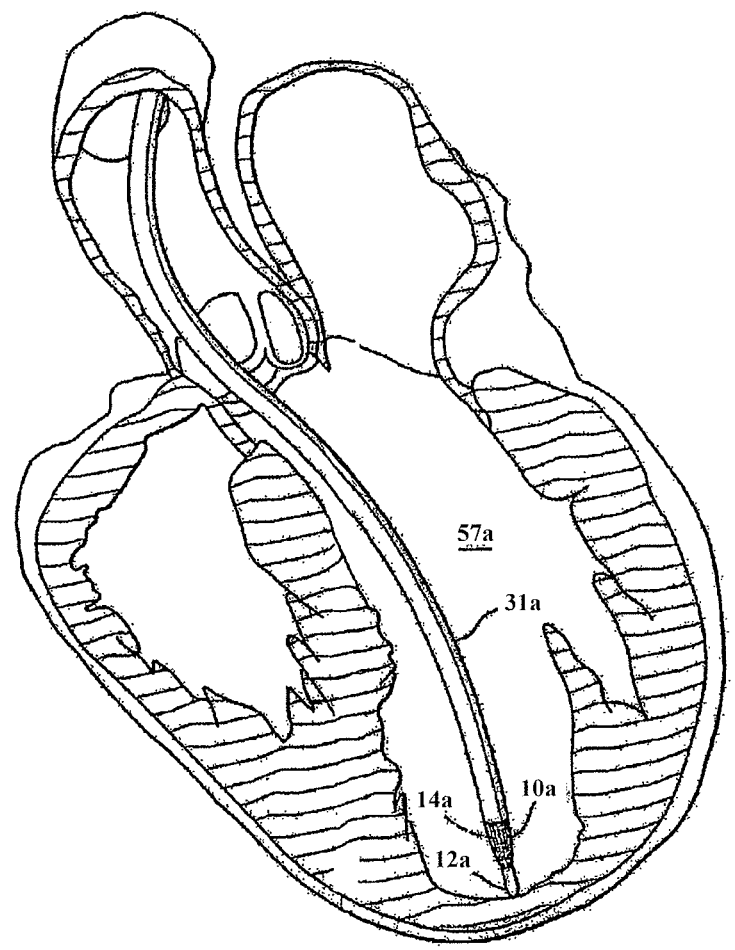
Figure 8C:
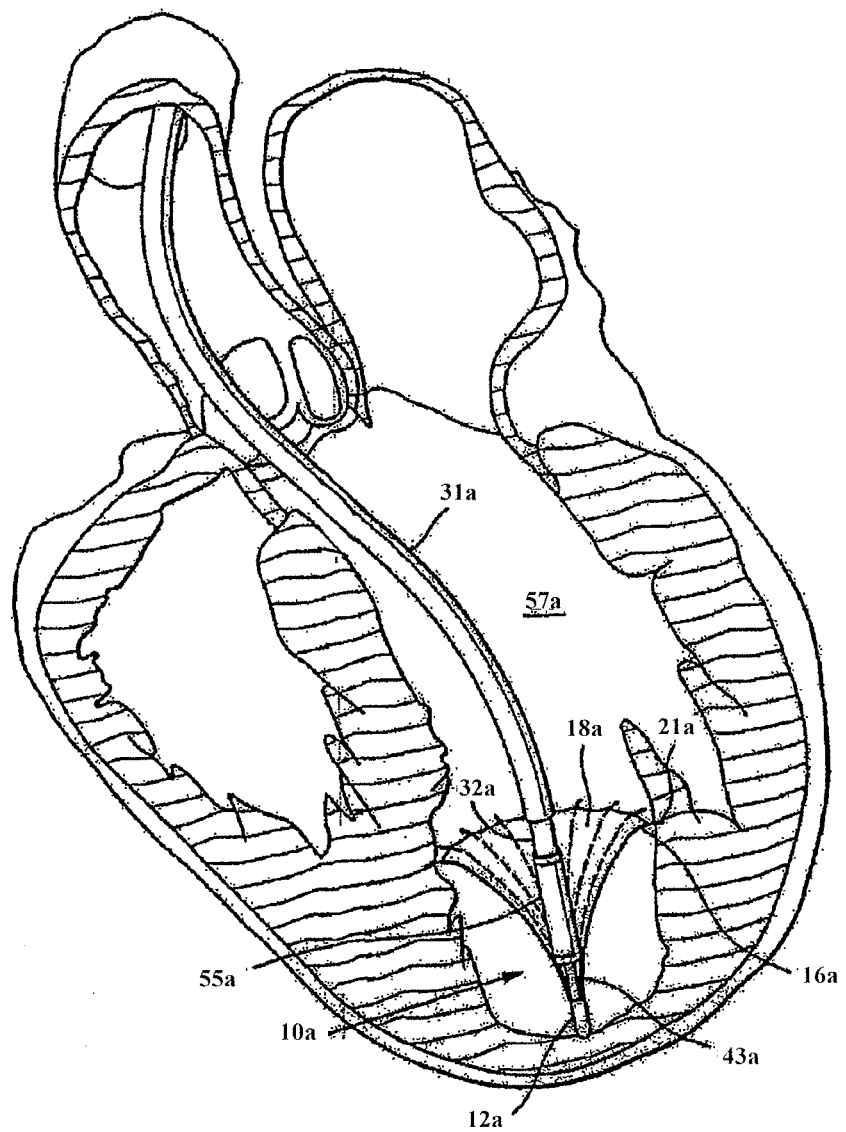
Figure 8D:
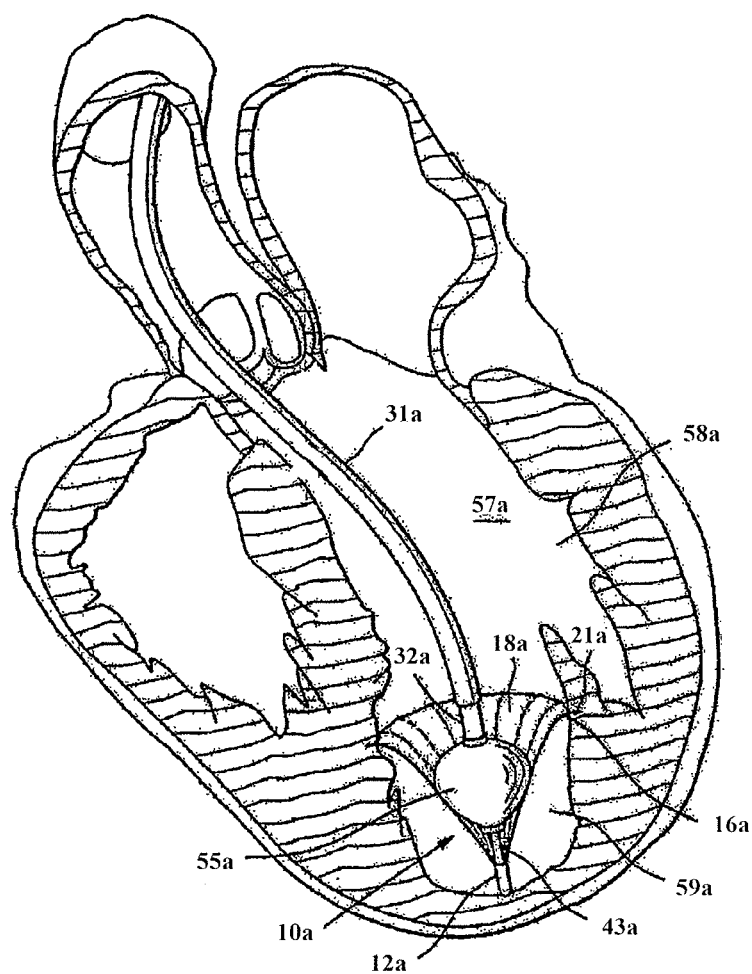

Returning to FIG. 5B, the partitioning component 10a mounted on the screw 53a is urged partially out of the inner lumen 33a of the guide catheter 31a until the hub 12a engages the heart wall as shown in FIG. 8B with the free proximal ends 16a of the ribs 14a in a contracted configuration within the guide catheter. The guiding catheter 31a is withdrawn while the delivery catheter 32a is held in place until the proximal ends 16a of the ribs 14a exit the distal end of the guiding catheter. The free proximal ends 16a of ribs 14a expand outwardly to press the sharp proximal tips 21a of the ribs 14a against and preferably into the tissue lining the heart chamber, as shown in FIG. 8C.

Figure 8E:
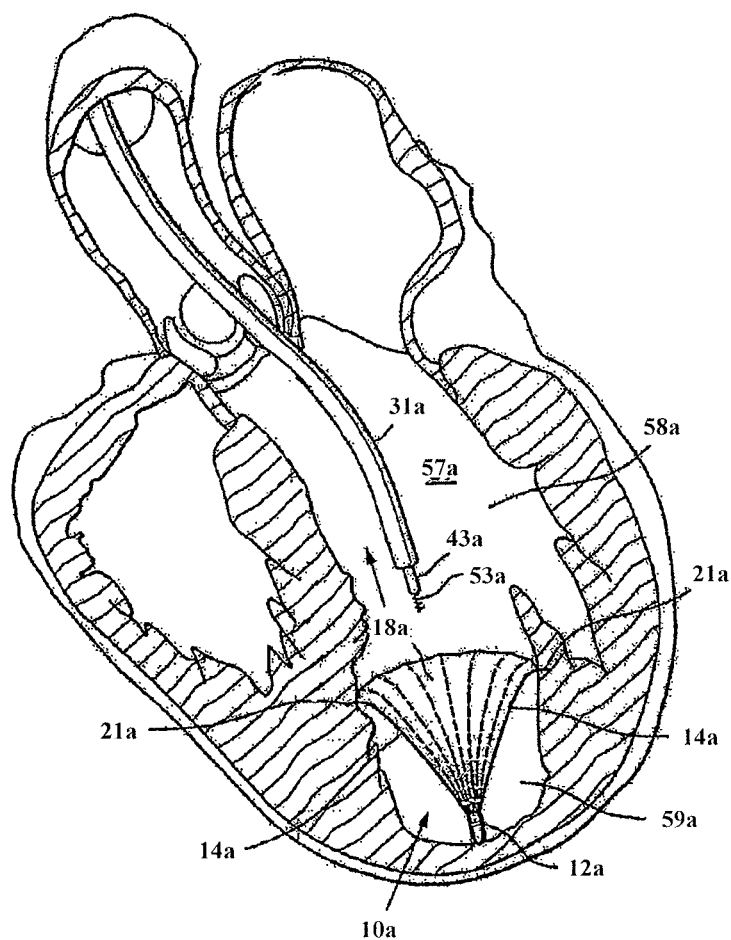

In FIG. 8E, with the partitioning device 10a properly positioned within the heart chamber 57a, the knob 49a on the torque shaft 43a is rotated counter-clockwise to disengage the helical coil screw 53a of the delivery catheter 32a from the stem secured within hub 12a. The counter-clockwise rotation of the torque shaft 43a rotates the helical coil screw 53a which rides on the connector bar 20a (shown in FIGS. 4 and 7) secured within the hub 12a. Once the helical coil screw 53a disengages the connector bar 20a (shown in FIGS. 4 and 7), the delivery system 30a, including the guide catheter 31a and the delivery catheter 32a, may then be removed from the patient. As shown in FIG. 8E, the partitioning component 10a partitions the patient's heart chamber 57a into a main productive or operational portion 58a and a secondary, essentially non-productive portion 59a. In some embodiments, the operational portion 58a is much smaller than the original ventricular chamber 57a and provides for an improved ejection fraction. The partitioning increases the ejection fraction and provides an improvement in blood flow. In some embodiments, it may be desirable to select a partitioning device that is most suitably sized and configured for a specific patient. This may be done in one of several different variations. In some embodiments, the patient may be pre-measured to determine a suitable device size. The patient may be measured in one of many suitable ways, including, but not limited to, mechanical or hydraulic measurement, 3D echo, CAT scan or LV-gram. FIG. 9 illustrates deployment of the partitioning device and delivery catheter similar illustrated in FIG. 5C; this FIG. 9 resembles FIG. 8D, above.

Returning to FIG. 5B, with the partitioning component deployed within the heart chamber and preferably partially secured therein, inflation fluid is introduced through the inflation port 46a into first lumen 44a of inner shaft 43a of the delivery catheter 32a where it is directed through port 44a into the balloon interior 56a to inflate the balloon. The inflated balloon presses against the pressure receiving surface 18a of the partitioning component 10a to ensure that the sharp proximal tips 21a are pressed well into the tissue lining the heart chamber.

With the partitioning device 10a properly positioned within the heart chamber, the knob 52a on the torque shaft 48a is rotated counter-clockwise to disengage the helical coil screw 53a of the delivery catheter 32a from the hub 12a. The counter-clockwise rotation of the torque shaft 48a rotates the helical coil screw 53a which rides on the connector bar 20a (shown in FIGS. 4 and 7) secured within the hub 12a. Once the helical coil screw 53a disengages the connector bar 20a (shown in FIGS. 4 and 7), the delivery system 30a, including the guide catheter 31a and the delivery catheter 32a, may then be removed from the patient.

The proximal end of the guide catheter 31a is provided with a flush port 36a to inject therapeutic or diagnostic fluids through the inner lumen 33a. Similarly, the proximal end of the delivery catheter 32a is provided with a flush port 42a in communication with inner lumen 41a for essentially the same purpose. An inflation port 46a is provided on the proximal portion of the delivery catheter for delivery of inflation fluid through the first inner lumen 44a to the interior 56a of the balloon 55a. Flush port 47a is provided in fluid communication with the second inner lumen 45a of the inner shaft 43a. An injection port 49a is provided on the proximal end of the torque shaft 48a in fluid communication with the inner lumen 51a of the torque shaft for delivery of a variety of fluids.

Returning to FIG. 8E, the partitioning component 10a partitions the patient's heart chamber 57a into a main productive or operational portion 58a and a secondary, essentially non-productive portion 59a. The operational portion 58a is much smaller than the original ventricular chamber 57a and provides for an improved ejection fraction. The partitioning increases the ejection fraction and provides an improvement in blood flow. Over time, the non-productive portion 59a fills first with thrombus and subsequently with cellular growth. Bio-resorbable fillers such as polylactic acid, polyglycolic acid, polycaprolactone, and copolymers and blends may be employed to initially fill the non-productive portion 59a. Fillers may be suitably supplied in a suitable solvent such as DMSO. Other materials which accelerate tissue growth or thrombus may be deployed in the non-productive portion 59a.

In some embodiments, as shown in FIG. 9, the implant also includes a sealing element, strand 19b, which may be used to help stiffen the edge of the membrane so that it may lie against the ventricle wall 59b and form a seal against the wall 59b. The strand 19b may also be used to help retrieve the device.

Figure 10:
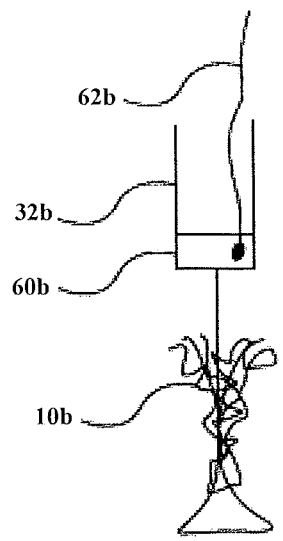
FIG. 10 illustrates one embodiment of the delivery system configured to maintain the position of the partitioning device while the guide catheter is withdrawn.

In some embodiments, as the guide catheter 31a, 31b is withdrawn, it begins to bend as it is withdrawn through the vascular anatomy of the patient, through the aortic arch, for example. In some instances, this bend may drive the distal tip of the delivery catheter, and therefore the partitioning device, out of position. For example, the guide catheter may drive the device towards the center of the heart, i.e. towards the ventricular septum. In some instances, it may be preferred that the delivery catheter and/or partitioning device are not moved or repositioned by the guide catheter as it is withdrawn. This may be accomplished in one of several embodiments. In a first embodiment, as shown in FIG. 10, a ring 60b is added to the distal end of the delivery catheter 32b. A wire 62b may be coupled to the ring 60b. The wire may be disposed along the length of the delivery and/or guide catheter, and may be configured to maintain the position of the distal end of the delivery catheter as the guide catheter is retracted into the vascular anatomy. For example, in some variations the wire is a rigidifying wire (or other element) that locks or holds the shape of the delivery catheter. In some variations, the wire is a pull wire. By pulling on or tensioning the pull wire, as shown in FIG. 10, the pull wire pulls on the ring 60b, bending the delivery catheter. This may prevent the ring and distal end of the delivery catheter, and therefore the partitioning device, from moving out of position. The pull wire, for example, may be used to pull the delivery catheter and partitioning device toward the apex of the heart, rather than towards the ventricular septum. In this embodiment, the guide catheter may be flexible such that the pull wire may effectively steer the delivery catheter as the guide catheter is withdrawn.

Figure 11:
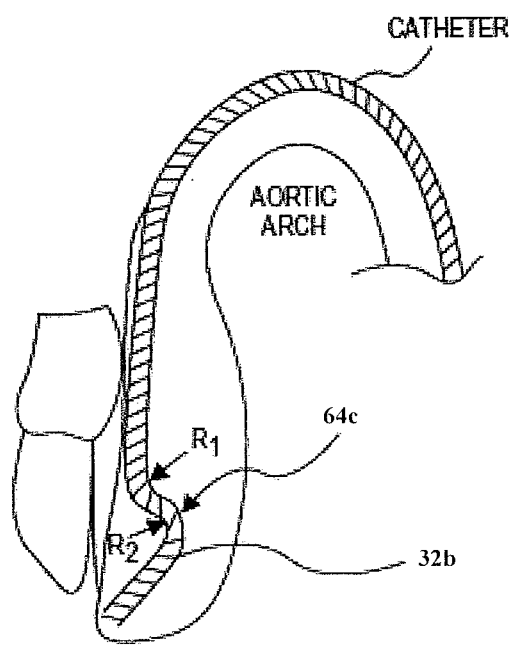
FIG. 11 illustrates one embodiment of the delivery system configured to maintain the position of the partitioning device while the guide catheter is withdrawn.
Figure 12:
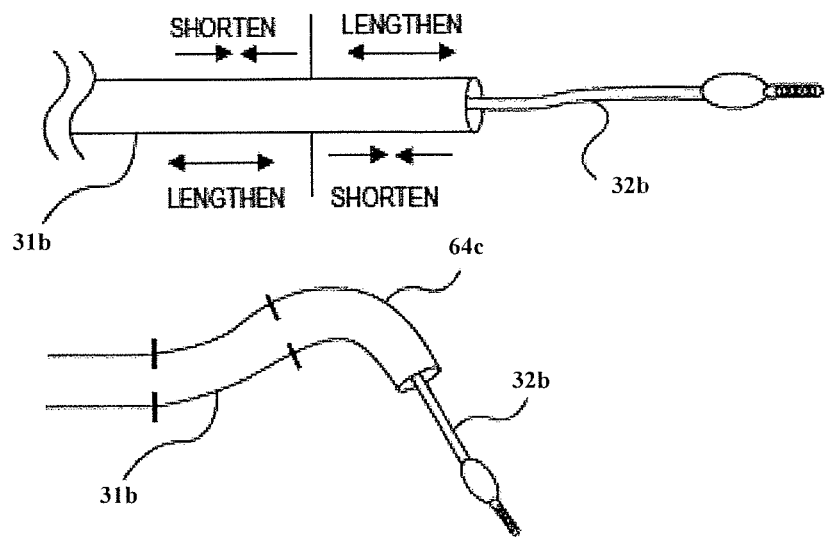
FIG. 12 illustrates one embodiment of the delivery system configured to maintain the position of the partitioning device while the guide catheter is withdrawn.
Figure 13:
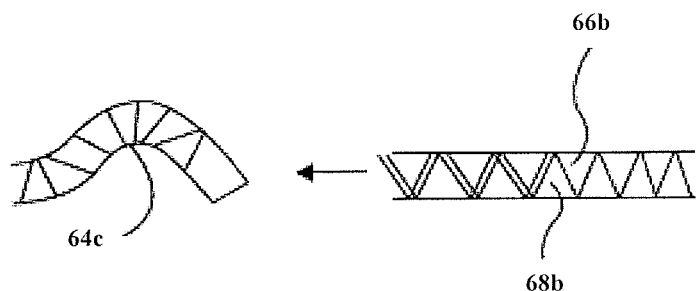
FIG. 13 illustrates one embodiment of the delivery system configured to maintain the position of the partitioning device while the guide catheter is withdrawn.

In some alternative embodiments, as shown in FIG. 11, the delivery catheter 32b is steerable. In some variations, the guide catheter is steerable (not shown). By having a steerable delivery catheter, the positioning of the partitioning device may be more controlled. For example, a steerable delivery catheter may hold the implant in place as the guide catheter is retracted to expose and/or deploy the partitioning device. The steerable delivery catheter may be steered or positioned into any number of suitable geometries. For example, the delivery catheter may be positioned into an S-curve 64c. This S-curve, as shown in FIG. 11, may be configured to position the catheter away from the ventricular septum and toward the apex of the heart, for example. The delivery catheter could be steerable by one of several different mechanisms. For example, as shown in FIG. 12, pull wires (not shown) may be used to lengthen and shorten various portions of the delivery catheter 32b (within the guide catheter 31b) to form the S-curve 64c. As shown in FIG. 13, the delivery catheter may include interlocking shafts, such as hypotubes 66b, 68b. The interlocking shafts may move with respect to one another to form the S-cure 64c.

In another alternative embodiment, not shown, the delivery catheter may be a shape set material, such as Nitinol. In some variations, the delivery catheter may be stiffer than the guide catheter, such that as the guide catheter is retracted or withdrawn, it imparts minimal forces on the more stiff delivery catheter. The delivery catheter may be set into any suitable shape, and be configured for any suitable vascular anatomy.

Figure 14:
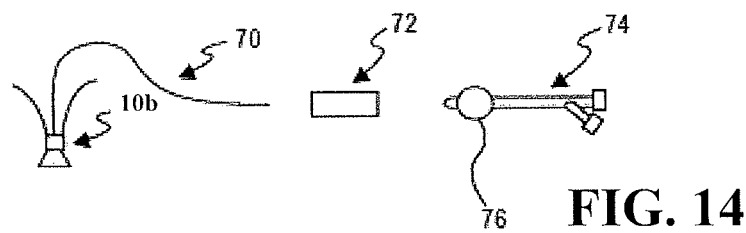
FIG. 14 illustrates one embodiment of the delivery system including an "over the wire" balloon system.

In some variations, the size of the expandable member may be limited by the size of the delivery diameter. For example in the stored configuration, i.e. when the expandable member, partitioning device, and the delivery catheter are within the guide catheter, each of the components contributes to the overall delivery diameter. The delivery diameter is preferably small to enable the passing of the guide catheter through the vasculature of the patient, therefore limiting the size of the expandable member and/or the size of the delivery catheter. To address these restrictions, in some variations (e.g., FIG. 14) the components of the delivery system 30a, 30b may be decoupled or separable from each other. For example, the delivery system may be decoupled into four separate components: a partitioning device 10b, a wire 70, a detachable handle 72, and an "over the wire" balloon system 74. The wire 70 may include a coupling mechanism, such as a helical screw, at the distal end that is configured to couple to the partitioning device 10b. The wire may be a conventional cardiovascular wire, or any other suitable wire. The wire may have a ground profile to optimize performance. The handle 72 may be coupled to the wire during the initial placement of the device, and then may be removed to allow the balloon system 74 to be coupled to the wire and advanced toward the partition device. Coupling to the wire in this example may be defined as positioning the handle, or balloon system, over the wire such that the wire is disposed along the length of an inside diameter of the handle or system. The handle may be replaced once the balloon system is in place, or alternatively, the balloon system may include a separate handle. The balloon system 74, having expandable member 76 (a balloon), may be a conventional balloon catheter or may be any other suitable "over the wire" system that is configured to expand the partitioning device.

Figure 15:
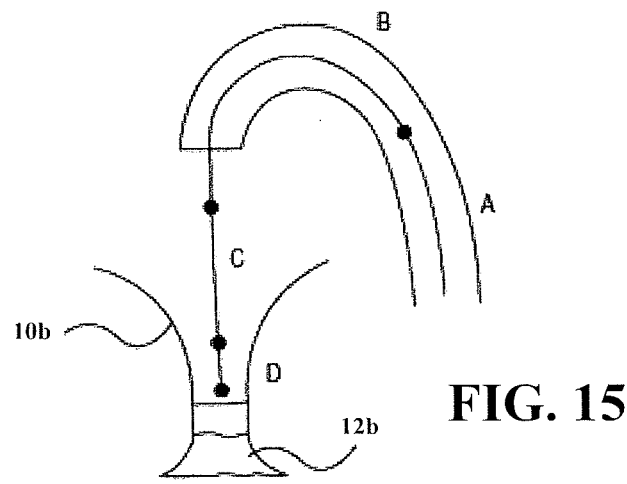
FIG. 15 illustrates one embodiment of the delivery system including an "over the wire" balloon system.
Figures 16A, 16B:
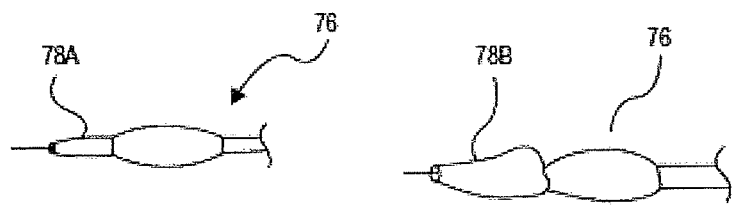
FIGS. 16A and 16B illustrates one embodiment of the delivery system including an "over the wire" balloon system.

In one variation, illustrated in FIG. 15, there may be four distinct regions of the delivery system (e.g., guide catheter), each having various requirements and characteristics. For example, in FIG. 15, the guide catheter includes four regions, A-D. Region A is pushable such that it may advance the guide catheter through the vasculature of the patient and/or push the partitioning device 10b out of the guide catheter. Region A may also be torqueable depending on the configuration of the coupling mechanism, for example, if the coupling mechanism is a screw. Region A may include a hypotube or a braided or coil wound shaft. Region B may be flexible to ensure that the device is positioned correctly, and not repositioned toward the septum, for example, during deployment. As with region A, region B may also be torqueable. Region B may include a highly flexible rigid shaft such as Nitinol (or other shape memory materials) or a braided or coil wound shaft. Region C may have a low profile such that is does not largely affect the overall delivery diameter or profile. Region C may also be pushable, such that it may advance the device and/or position the hub 12b or foot of the device. Region C may be a hypotube or solid shaft. Region D may be removably attached to the partitioning device 10b. Region D may include a coupling mechanism such as a coiled screw, a suture, or a hitch-pin (described below). In some variations, regions A through C may form a wire, similar to wire 70 in FIG. 14. A balloon system 74 may be advanced over regions A through C. FIGS. 16A and 16B illustrate one variation of a delivery system including an expandable member that is a balloon that is deliverable over a wire forming part of the guide catheter. In this example, the balloon may be configured to minimize the overall profile of the system.

Figure 17:
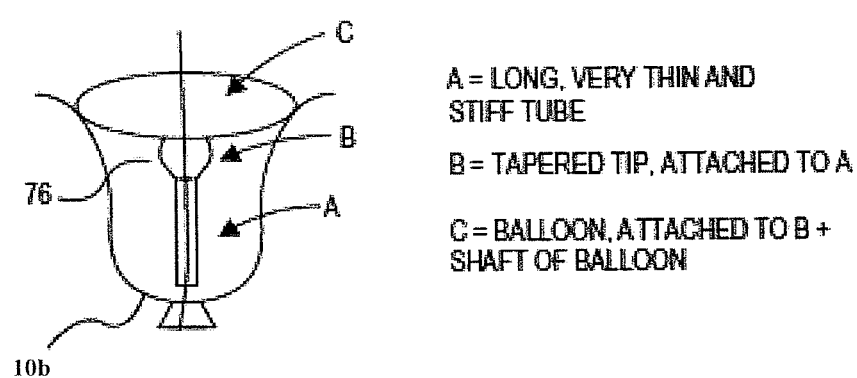
FIG. 17 illustrates one embodiment of the delivery system including an "over the wire" balloon system.
Figure 18A:
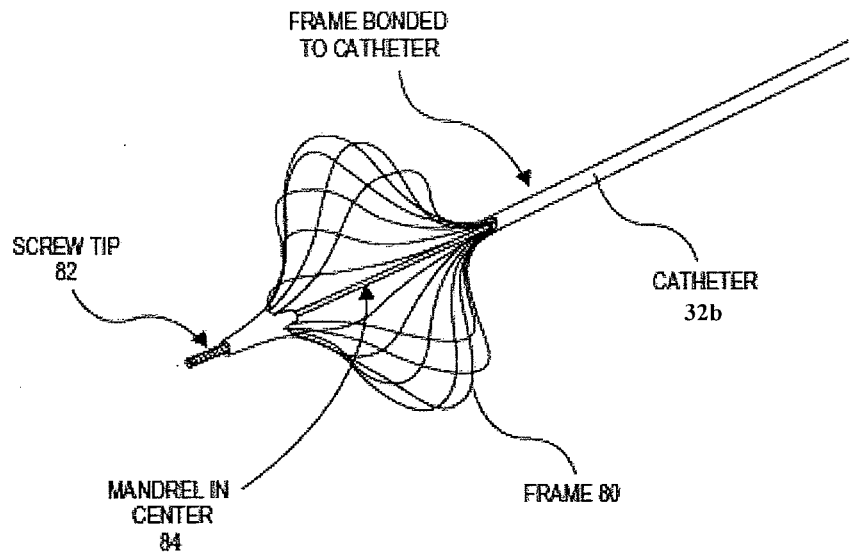
FIGS. 18A-18F illustrate one embodiment of the delivery system including an expandable member.
Figure 18B:
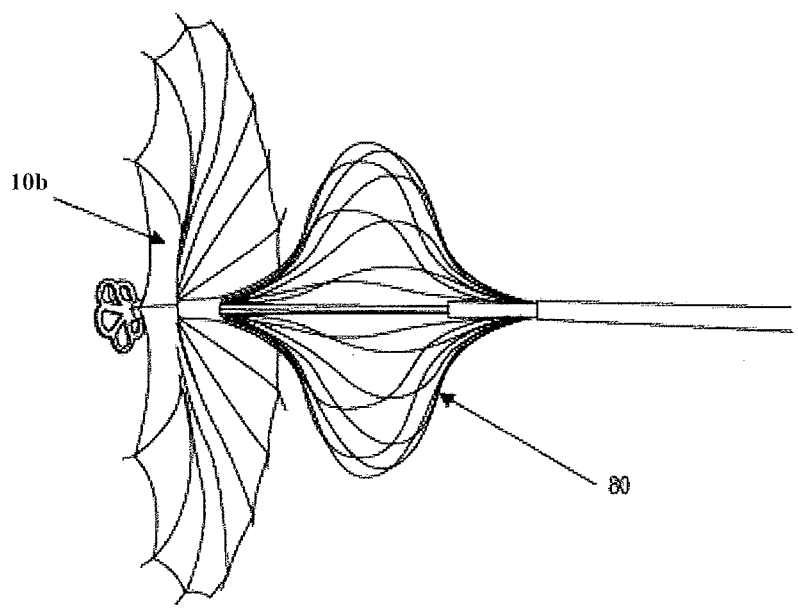
Figure 18C:
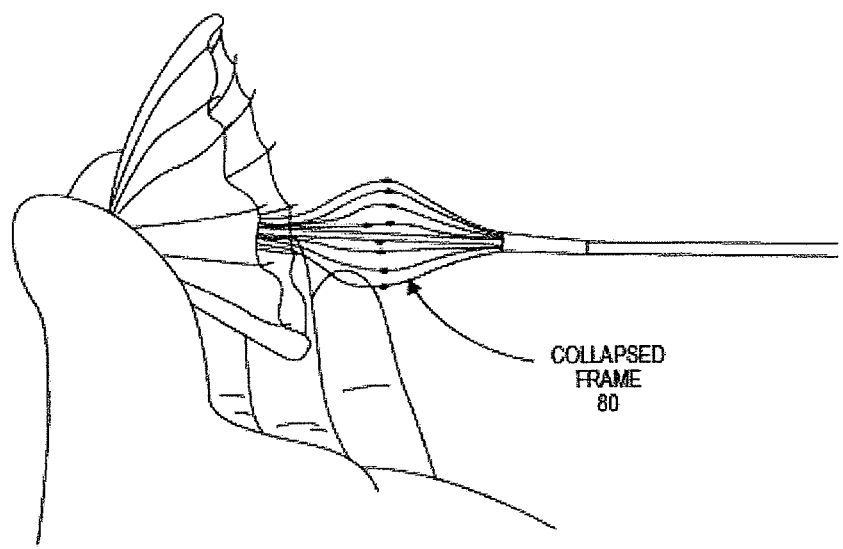
Figure 18D:
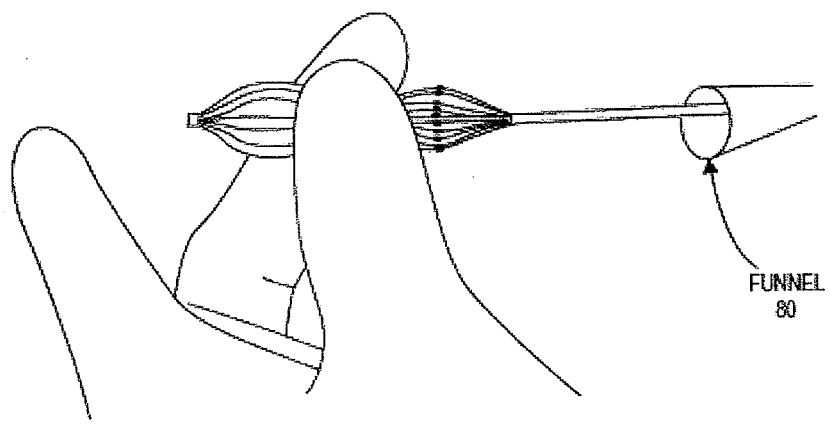
Figure 18E:
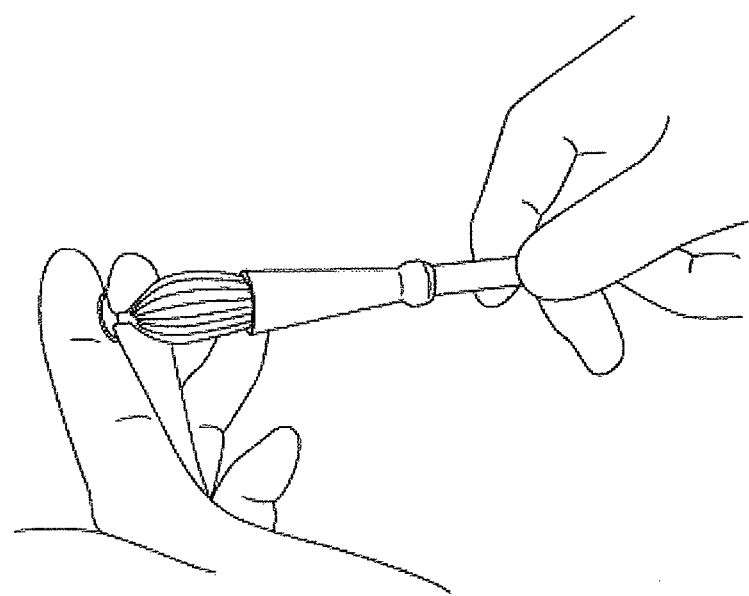
Figure 18F:
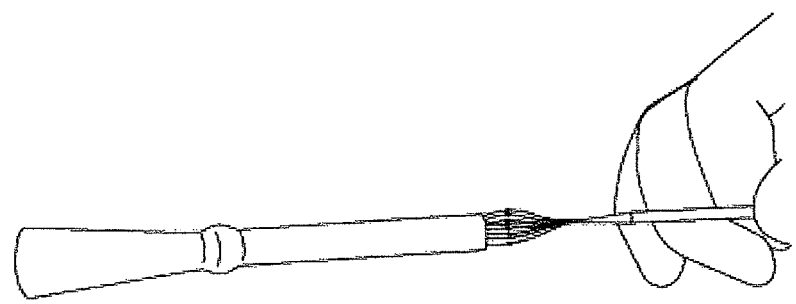

As shown in FIGS. 16A-17, balloon 76 of the balloon system 74 may include any number of features such that it is configured to expand the partitioning device 10b. FIG. 16A shows a conventional angioplasty balloon tip 78A. FIG. 16B shows a more aggressive tip 78B configured to insert into the distal portion of the partitioning device 10b when it is collapsed. As shown in FIG. 17, the balloon 76 may include three portions A, B, C. In some embodiments, portion A remains within the distal end of the partitioning device 10b during delivery. The tip portion, portion A, is a distal nose region that may have a small profile such that it is configured to not largely contribute to the overall delivery profile. Portion A is also configured to position portions B and/or C in the correct position with respect to the partitioning device. For example, the length of portion A may be selected so that when balloon 76 is fully advanced, the distal tip of portion A contacts the partitioning device, and the expandable balloon (portion C) is optimally positioned to expand the partitioning device. Portion A may be part of the balloon, or it may be a separate portion such as a tube. Portion A may be stiff in some embodiments. Portion C is the expandable balloon portion and is configured to interact with the distal end of the partitioning device. Portion B may be a tapered region. The taper may be relatively gradual or more extreme, and allows the transition between the distal tip and the balloon, allowing the entire expandable region to be inserted into the collapsed partitioning device.

Another example of an expandable member is shown in FIGS. 18A-20. In this example, the expandable member is a mechanical expander. The mechanical expander in this example is a frame 80 formed of a plurality of arms or struts that are joined at their proximal and distal ends, as shown. The arms may be collapsed down or expanded by moving the proximal and distal ends of the frame relative to one another. The proximal end of the frame 80 may be coupled to the delivery catheter 32b and the distal end of the frame may include a coupling mechanism 82, such as a screw tip. The coupling mechanism may be coupled to the partitioning device 10a/10b, as shown in FIG. 18B. The frame 80 may further include a mandrel 84 configured to move the frame 80 from a collapsed to an expanded configuration. A pull wire or other suitable mechanism may be coupled to the mandrel 84 such that it may be moved and thereby move the frame 80. FIGS. 18C to 18F illustrate loading the implant 10b (partitioning device) onto a guide catheter such as the one shown in FIGS. 18A and 18B. The implant may be coupled to the guide catheter in an expanded state, and then collapsed down (around the mechanical expander as shown in FIG. 18D). A loading tool (e.g., funnel) device may be used to help load the implant onto the delivery system, as shown in FIGS. 18E and 18F. Once the implant is in the loading tool the system may be loaded into a delivery catheter for inserting into the patient. The implant may be flushed (e.g., with saline) first.

Figure 19:
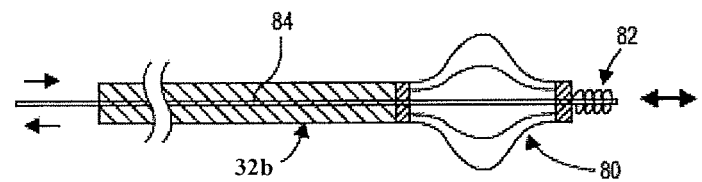
FIG. 19 illustrates one embodiment of the delivery system including an expandable member.
Figure 20:
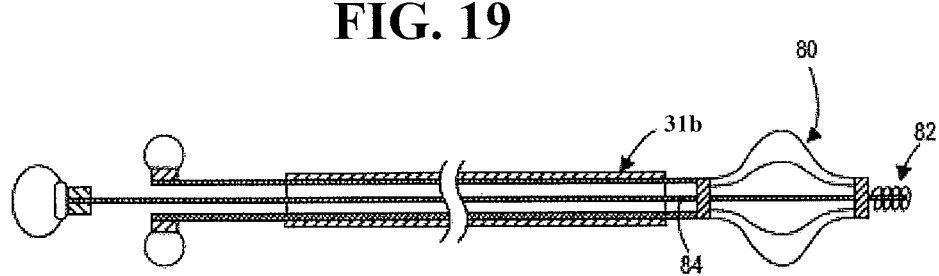
FIG. 20 illustrates one embodiment of the delivery system including an expandable member.

FIGS. 19 and 20 illustrate another variation of a delivery catheter including a mechanical expander. In this variation, the expander region is controlled by a mandrel 84 that is extendable and retractable to collapse or expand the mechanical expander region. FIG. 20 shows one variation in which a proximal handle includes grips (finger grips) for actuating the expander relative to the rest of the catheter. Expanding the mechanical expander pushes against the inner portion of a collapsed implant and aids the implant in expansion and attachment (sealing) to the ventricle wall(s). The mechanical expanders described herein may have advantages compared to the balloon expanders mentioned above. For example, the mechanical expanders may be precisely controlled. In addition, the mechanical expander may be shaped to more optimally contact the implant. Finally, the mechanical expander may be expanded larger than the balloons, while having a smaller cross-sectional area, thereby allowing smaller diameter delivery/guide catheters. In addition, the mechanical expander may not require the pressurized inflation fluid.

Figure 21:
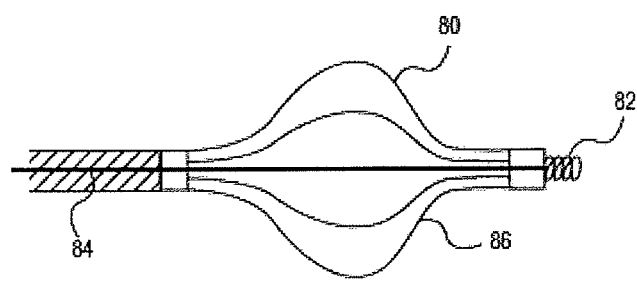
FIG. 21 illustrates one embodiment of the delivery system including an expandable member.

FIGS. 21-26 illustrate variations of mechanical expanders. For example, as shown in FIG. 21, the frame 80 may be formed of heat set Nitinol, or other shape memory material, in a shape such that the resting position is the expanded position, as shown. The frame may be made out of a tube that is laser cut to form the struts 86 of the frame 80. In this configuration, the mandrel 84 may be pushed to compress the frame radially such that it may be advanced through the guide catheter. The mandrel 84 may then be pulled to expand the struts 86 radially to expand the frame 80. As shown in FIG. 22, the frame 80 may be collapsed by pulling proximal and distal ends apart. As mentioned, the frame (arms/struts) may be made at least in part from heat set Nitinol, or other shape memory material, in an expanded or unexpanded shape. The frame may be made out of a tube that is laser cut to form the struts 86 of the frame 80. In this configuration, the mandrel 84 may be pushed to compress the frame radially such that it may be advanced through the guide catheter. The mandrel 84 may then be pulled to expand the struts 86 radially to expand the frame 80. The material of the frame 80, such as Nitinol, may be heat treated such that the struts are predisposed to expand. As shown in FIG. 23, the frame 80 may have a symmetric or asymmetric shape along its axial length. For example, in FIG. 23, the frame is a teardrop shape. In some variations the wider diameter region of the tear drop shape is located more proximally, nearer the region where the implant will expand the most (and contact the wall of a ventricle). The material of the frame 80, such as Nitinol, may be heat treated such that the struts are predisposed to expand at the distal or proximal end of the frame. In this embodiment, the frame may contact the device 10a, 10b further down on the device, requiring less radial expansion to open the implant. As shown in FIG. 24, the frame 80 may expand into a fully circular shape. As shown in FIG. 25, the frame 80 may be made out of a spiral cut tube. The material of the frame 80, such as Nitinol, may be heat treated such that the struts are predisposed to expand. This configuration is such that at least a portion of the frame 80 will contact the device 10a on the ribs 14a of the device, since the spiral of the expansion member frame will place the frame arms at an angle relative to the ribs of the implant. Thus the frame may push against the ribs of the implant preferentially, rather than the membrane. FIG. 21 illustrates an example in which the arms forming the frame are cut to bias the bending (hinge) region. In this example, cuts 88 in the frame material are configured to predispose bending of the frame at specified locations. A detailed view is shown in FIG. 26A. The cuts 88 may be placed in any suitable location for any suitable device geometry.

As shown in FIGS. 27-28B, the mechanical expansion member (e.g., frame 80) and the catheter 32b (e.g., guide catheter, delivery catheter) may be made out of a single length of tube. In the example shown in FIG. 27, the distal end region of the tube includes keyed slots 90 cut into the tube to form a flexible portion of the delivery catheter 32b. Toward the more distal end of the tube, slots 92 have been cut into the tube to form the expandable struts 86 of frame 80. In some variations the keyed slots 90 may be formed by a single, continuous helical cut. Alternatively, keyed slots may be formed by multiple circumferential cuts along the length of the delivery catheter portion. The catheter 32 in this embodiment may be more flexible than a standard hypotube, while still being torqueable and having a good push/pull response. FIGS. 28A and 28B illustrate partial views of "unrolled" templates for some of the laser cuts that may be made to form a catheter having a mechanical expansion member. For example, FIG. 28A shows a version with laser cut arms that run parallel to the long axis of the catheter, while FIG. 28B shows a variation in which the laser cut arms spiral around the circumference of the catheter once it has been constructed.

Figure 29:
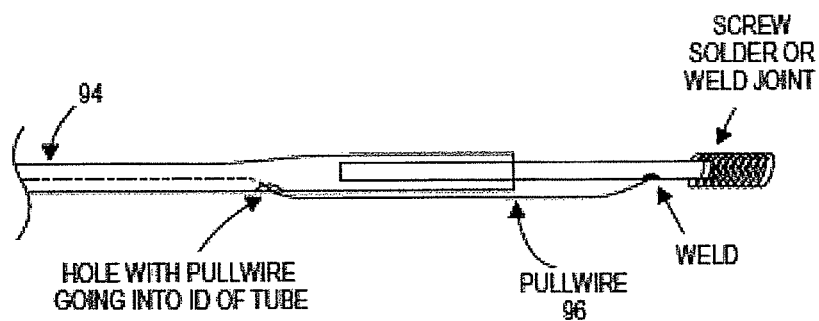
FIG. 29 illustrates one embodiment of the delivery system including the frame and the delivery catheter formed from a single tube.
Figure 30:
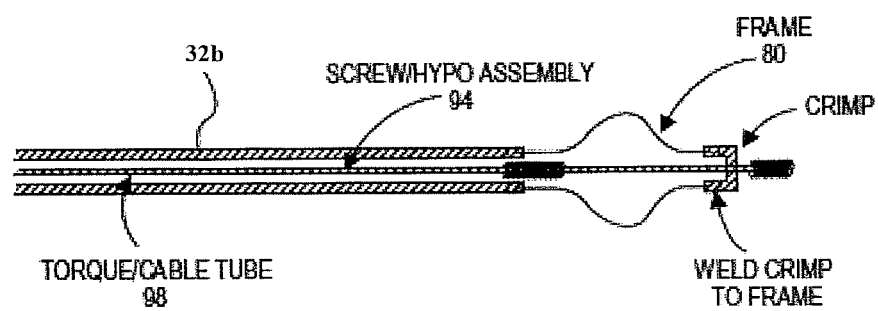
FIG. 30 illustrate an alternative embodiment of a delivery system wherein the frame and catheter are formed from separate components.

As shown in FIG. 27, the delivery system may further include a tube and/or shaft 94 within the catheter. FIG. 29 shows a more detailed example of this tube. A tube/shaft 94 may be configured to couple to the coupling mechanism 82 (or to be part of the coupling mechanism) to release the device 10. The tube/shaft 94 may move independently from the rest of the catheter 32b, and may be referred to as a torque shaft. Alternatively or additionally, the tube/shaft 94 may include a lumen through which any suitable liquid may be injected. As shown in FIG. 29, the system may further include a pull wire 96. In this example, the pull wire may function to pull and/or deflect the distal end of the catheter to steer and position the partitioning device. As shown, the pull wire does not have to go through torque tube 94, but could run along the outside of the tube and/or delivery catheter 32b. FIG. 30 shows one variation of a guide catheter including an extruded plastic cover 98 over a portion of the guide catheter. In another variation, the catheter is plastic, and the mechanical expansion members are secured thereto. In some embodiments, a reflow process may be utilized to bond the plastic onto the torque tube.

Figure 31:
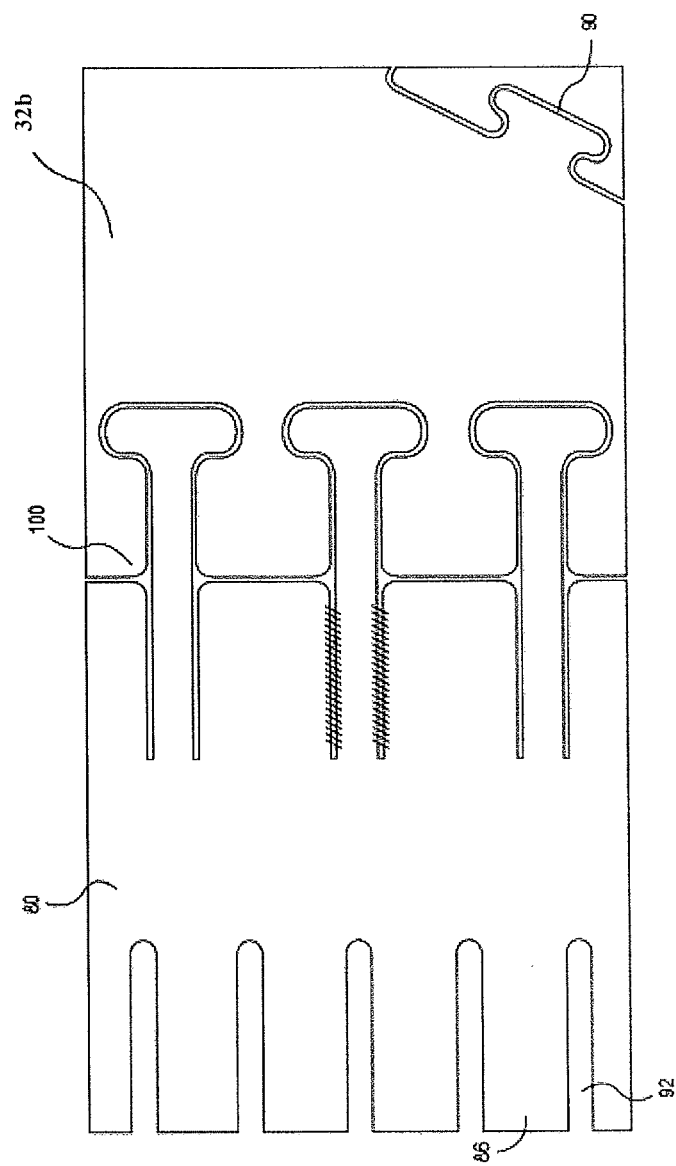
FIG. 31 illustrates an alternative embodiment of the delivery system wherein the frame and the guide catheter are formed from tubes and snapped together.

In general, it may be beneficial to have the mechanical expansion member be formed of a shape memory or hyperelastic material such as Nitinol. However, it may be desirable to have the rest of the catheter (e.g., the rest of the body region proximal to the expansion member) formed of a different material, such as stainless steel. FIG. 31 illustrates one variation of a catheter (or region of a catheter) having a Nitinol mechanical expansion region and a stainless steel proximal region. In FIG. 31, rather than forming the guide catheter 32b and the frame 80 out of a single tube, the catheter may be formed out of a first tube of a first material (e.g., stainless steel), and the frame 80 forming the arms of the mechanical expansion member may be formed out of a second material (e.g., Nitinol). This configuration may allow the delivery system to be made in a more cost effective manner. As shown in FIG. 31, the proximal end of the frame 80 and the distal end of the delivery catheter may include cuts 100 that are configured to snap the proximal end of the frame 80 onto the distal end of the delivery catheter. Cuts 100 provide a good mechanical interface between the frame 80 and the delivery catheter 32b, providing enhanced column strength beyond what a simple weld may produce. Cuts 100 may also allow the tabs to bend and the tubes to be joined. After snapping the tubes together, cuts 100 are welded closed, eliminating the flexibility of the tabs thereby locking the tubes together (without requiring dissimilar metals to be welded, which may cause faults in the final product).

Figure 32A:
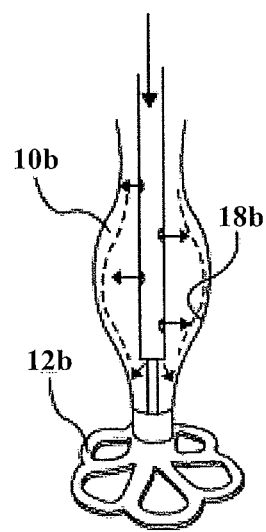
FIGS. 32A and 32B illustrate various embodiments of the delivery system wherein the expandable member is a hydraulic system.
Figure 32B:
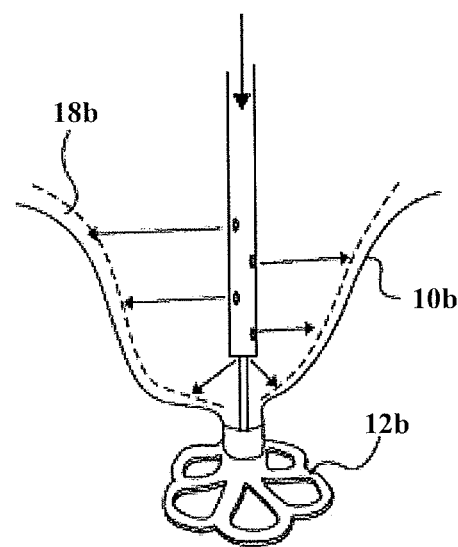

In some variations, the expandable member is a pneumatic, or fluid-pressure based member, as shown in FIGS. 32A and 32B. In this example, the expandable member may include a hydraulic system that is configured to apply pressure to the inner surface 18b of the partitioning device 10b to drive it open and/or seal it to the ventricle wall. The system may use a rapid saline injection or any other suitable system to apply pressurized fluid flow against the inner surface 18b of the partitioning device 10b to expand the device 10b. In some variations, the system may inject a contrast to aid in the radiopacity of the device and/or area surrounding the device. The expansion member may include a fluid delivery member (tube, passage, etc.) that has multiple ports oriented at different directions/angles to drive the fluid against the partitioning device to deploy the partitioning device.

Figure 33A:
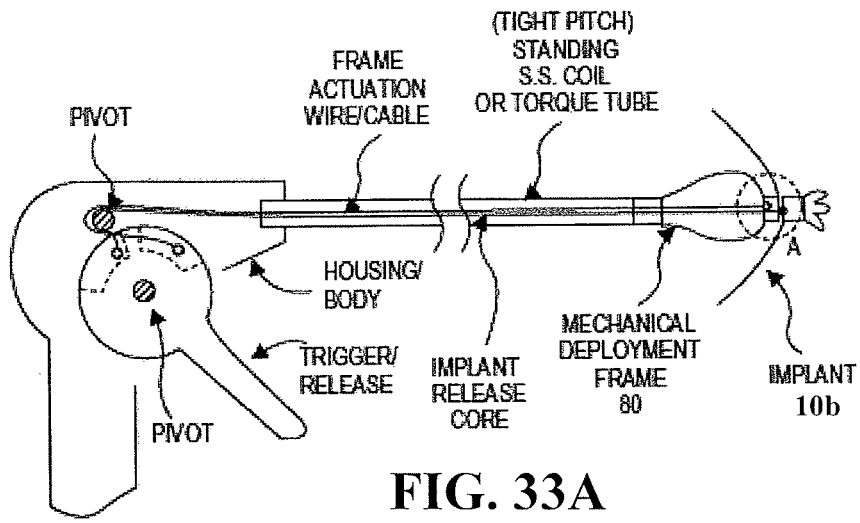
FIGS. 33A and 33B illustrate one embodiment of a deployment system, i.e. handles.
Figure 33B:
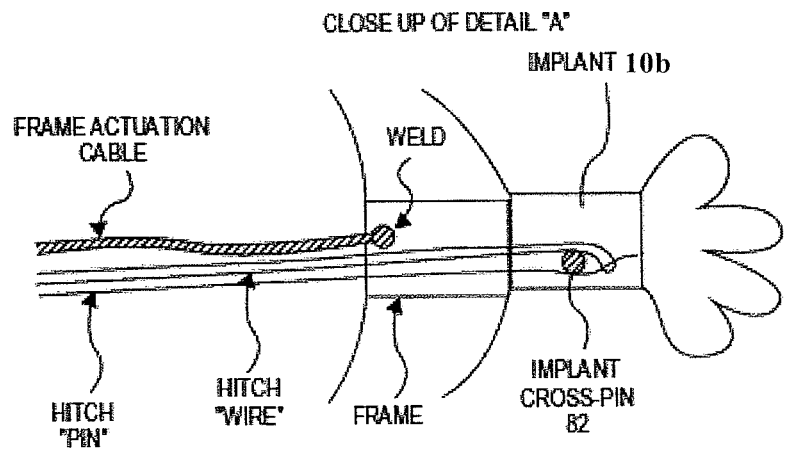

In general, after a partitioning device 10a has been properly positioned within the ventricle, the partitioning device 10b may be deployed and/or released from the guide catheter. As shown in FIGS. 33A-37, the delivery system may include one of several variations of deployment systems, i.e. handles. The deployment of the device is preferably performed in a controlled manner. As shown in FIGS. 33A and 33B, the system may include a "pistol grip" handle. This embodiment may include any of the following features: one handed actuation/deployment and release of the partitioning device 10b, a keyed interaction between the handle and the catheter to allow for rotation of the partitioning device prior to release, a torsion spring to allow for multiple expansions of the deployment frame 80 prior to release of the partitioning device, a hitch-pin coupling mechanism 82 as described in more detail below, and a preloaded partitioning device within the delivery system.

Figure 34:
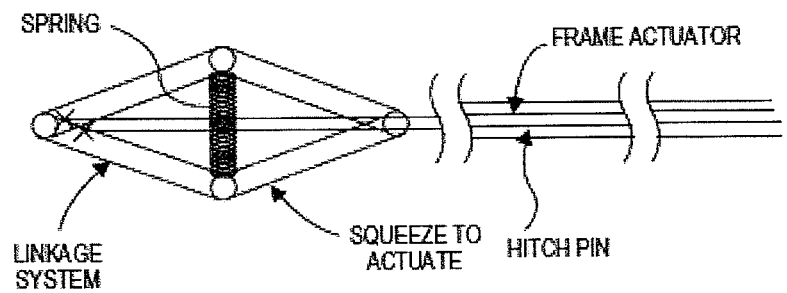
FIG. 34 illustrates one embodiment of a deployment system, i.e. handles.
Figure 35:
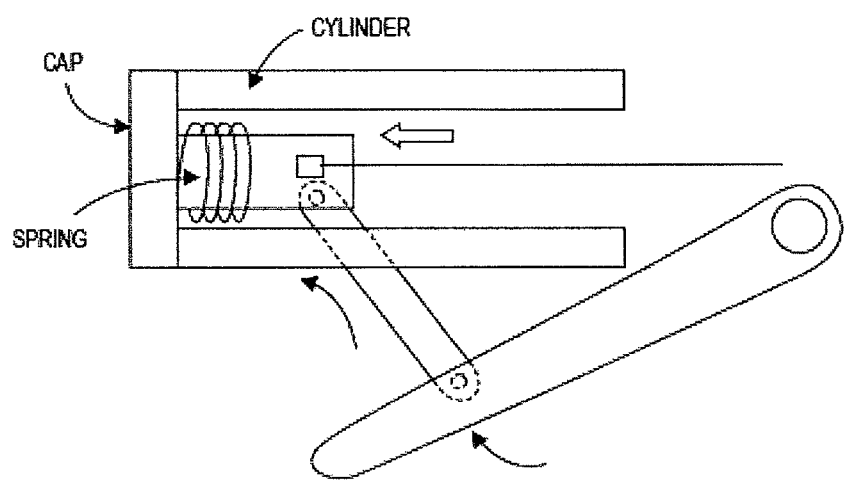
FIG. 35 illustrates one embodiment of a deployment system, i.e. handles.
Figure 36:
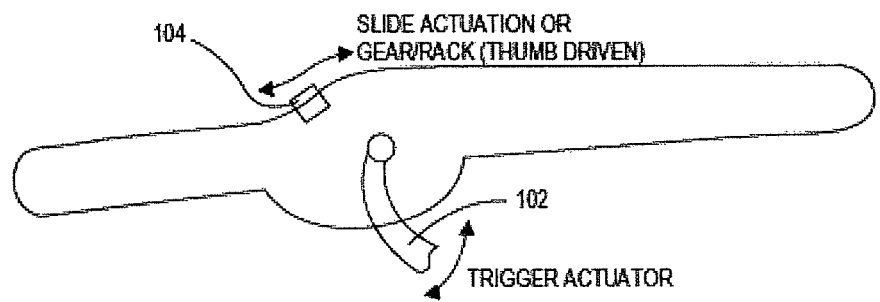
FIG. 36 illustrates one embodiment of a deployment system, i.e. handles.
Figure 37:
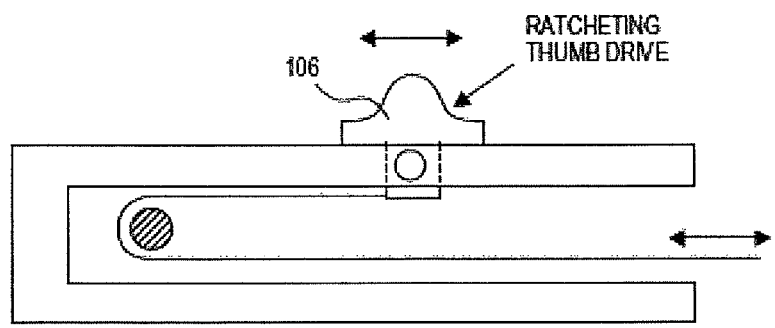
FIG. 37 illustrates one embodiment of a deployment system, i.e. handles.

In one variation, shown in FIG. 34, the system may include a "squeeze grip" handle. This handle may also include any combination of the features listed above. FIG. 35 shows another variation of a "squeeze grip" handle, having a trigger-like control for driving contraction/extension of a pullwire, which may be connected to a mechanical expansion member and/or a coupling element. As shown in FIG. 36, the system may include a "remote grip" handle. This handle may be actuated by a mechanism such as a trigger 102, a slide 104, and/or a button. As shown in FIG. 37, the system may include a "sliding grip" handle. This handle may be actuated by a mechanism such as a ratcheting thumb button 106. Any of the handles described herein may be used as part of an expansion control and/or a deployment control.

Figure 38:
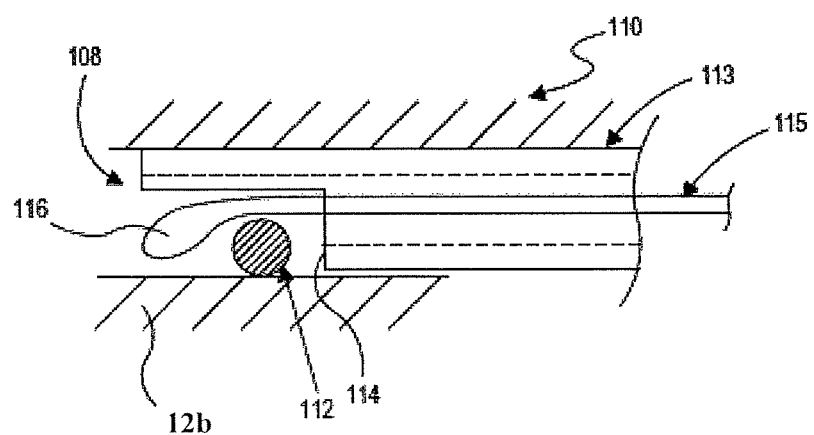
FIG. 38 illustrates one embodiment of a coupling mechanism.

The partitioning device may be coupled to the delivery catheter and then released in one of several embodiments. In some embodiments, a torque shaft within the delivery system is rotated to disengage the helical coil screw 53a, 50b of the delivery catheter 32a, 32b from the hub 12a, 12b. The rotation of the torque shaft 48a, 44b rotates the helical coil screw 53a, 50b which rides on the connector bar 20a secured within the hub 12a, 12b. Once the helical coil screw 53a, 50b disengages the connector bar 20a, the delivery system 30a, 30b, including the guide catheter 31a, 31b and the delivery catheter 32a, 32b, may then be removed from the patient. In alternative embodiments, as shown in FIG. 38, the coupling mechanism is a hitch-pin mechanism 108. The hitch-pin 108 may include several components. For example, the hitch pin may include a feature 110 in the device foot 12b allowing for entry of the retention/release mechanism. Further, the hitch pin includes element 112 within element 110 that is configured to partially restrict the hole (feature 110). In some variations, element 112, is a cross pin. Element 113 may be a tube with a notch 114 in the distal end of the tube. Element 115 may be a rod with a bulbous feature 116 on the distal end of the rod. With tube 113 in place, the bulbous feature 116 cannot fit past cross pin 112, however, once tube 113 is removed, the rod 115 and end 116 can be removed. Tube 113 is removed by pulling the tube in the proximal direction. This motion may be simpler than a torque motion required to decouple the helical screw embodiment.

Figure 39:
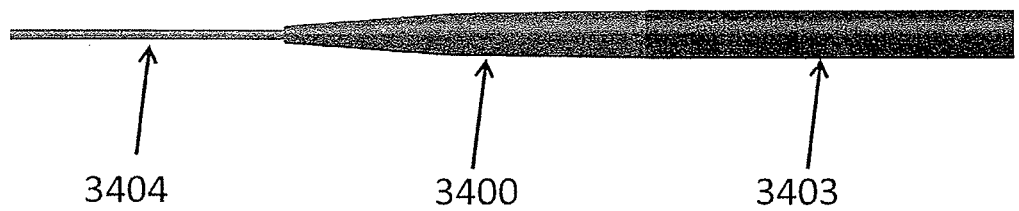
FIG. 39 illustrates an embodiment of a conical dilator.

In some embodiments a conical dilator 3400, as illustrated in FIG. 39 may be used in combination with a guide catheter 3403 and wire 3404 to facilitate access to the vasculature. The use of a conical dilator may avoid the need to use a procedural introducer sheath, thereby reducing the size of an arteriotomy or venotomy, and reducing at least one of the time, cost, and loss of blood from the patient throughout the overall procedure. Additionally, the conical dilator may facilitate vessel navigation and tracking of the device through the vasculature, for instance tracking through the aortic arch. For example, the tapered tip may travel through the aortic arch and across the valve less traumatically than a blunt ended catheter. In some embodiments, the conical dilator may be utilized during transseptal access procedures, as described in detail below.

Once the guide catheter is delivered within the patient's heart, specifically within the left ventricle, the conical dilator may be removed from the guide catheter, prior to introduction of the delivery catheter-implant assembly into the guide catheter and/or prior to the delivery of the implant. In some embodiments, the tapered dilator may be removed by and/or with the guidewire.

Figure 40:
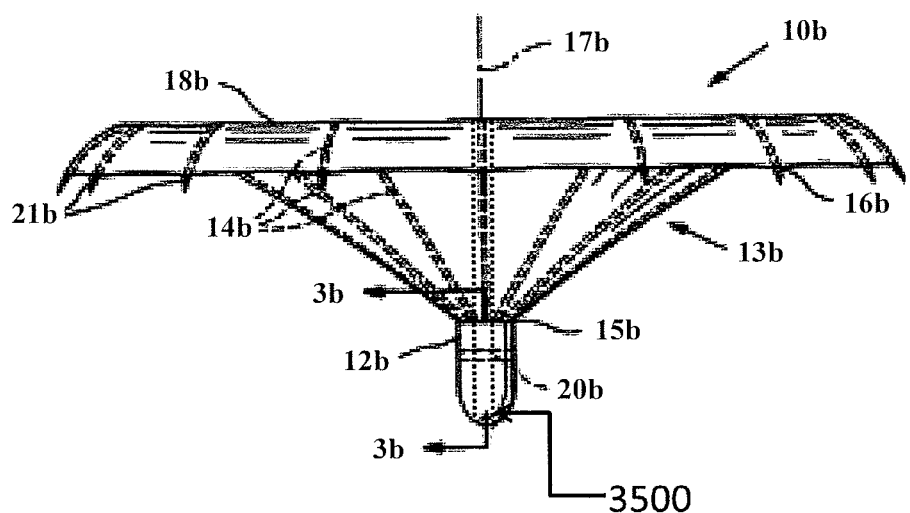
FIG. 40 illustrates a partitioning device embodying features of the invention, including a guidewire lumen, the device shown in an expanded configuration.

In some embodiments, as shown in FIG. 40, a guidewire lumen 3500 may be incorporated in the device. The guidewire lumen may extend throughout the whole device, as shown, or may be configured as a rapid-exchange feature. In both cases delivery of the device over a guidewire may be enabled, allowing for an additional mechanism of targeting the distal end of the device to the intended landing zone. In some embodiments, in order to protect the inner surface of the device, or more specifically the membrane, from abrasion as the device is passed over the wire, a lubricious coating may be applied to the guidewire, or alternatively a protective sleeve may be incorporated in the device.

In some embodiments, the guidewire may include an anchoring mechanism at the distal tip of the guidewire, for instance a threaded tip, which may be employed to anchor the wire at the intended anchoring site within the patient's ventricle, thus allowing the wire to act as an anchor for delivery of the partitioning device. For example, the guidewire may be positioned within the ventricle, and the distal tip of the guidewire may then be anchored or otherwise coupled to the ventricular wall. Once the guidewire is in position, the implant may be deployed over the guidewire into the patient's ventricle.

In some embodiments of the device, radio-opaque markers may be incorporated into the device. The markers may be included on the implanted partitioning device and/or on the delivery system. Radio-opaque markers may be constructed from biocompatible heavy metals, such as gold, platinum, and tantalum, and may be fabricated in any form or shape suitable for the intended device, such as bands, tabs, ribbons, disks, and the like. They may be in the form of components specifically included for the purpose of providing radio-opacity, or they may be inherent components of a device, made out of a radio-opaque material to provide radio-opacity. In some embodiments, as shown in FIG. 41A, the distal end of the elongate guide catheter and/or delivery catheter 3600 for a transvascular approach may include a marker band 3602. As shown, the catheter 3600 may be delivered to the apex of the patient's heart, and the marker band 3602 may indicate the height and/or position of the anchors in their deployed configuration. Alternatively, the marker band 3602 may be positioned on catheter 3600 to indicate any other suitable positioning information of the implant or other component of the system.

In some embodiments the systems and methods described herein may be capable of delivering a partitioning device to a ventricle by a transseptal approach. This approach may advantageously be used in patients with compromised femoral arterial anatomy, with a compromised aorta or aortic valve, and/or where delivery through an arterial approach may be considered undesirable or unfeasible.

In a typical transseptal procedure access to the left heart is achieved by way of the right heart, typically the right atrium. Access to the right heart is generally achieved by means of a venous access, for instance through a femoral or jugular vein. A guidewire may be used to establish the access route, and may be threaded through a cardiac septum, for instance through the inter-atrial foramen ovale to establish access to the left heart. Subsequently, the guidewire may be routed through the mitral valve into the left ventricle and into vicinity of the apex of the heart. Alternatively, the use of the guidewire may be limited to access to the left atrium.

Passage of a guide catheter through the foramen may be enabled by the use of a conical dilator, as described above in reference to FIG. 39, in combination with a guide catheter to dilate the transseptal aperture to allow passage of the guide catheter. The conical dilator may be removed with the guidewire prior to loading the delivery catheter into the guide catheter. In the case where targeting the landing zone is established with a guide wire, the guidewire may be left in place during removal of the conical dilator and advanced to its desired position. As described above, in some embodiments, the guidewire may be anchored in the landing zone prior to delivering the implant. The delivery catheter may then be advanced over the guidewire to the landing zone, and the partitioning device may be delivered as described above.

Alternatively, positioning of the delivery catheter may be achieved with a steerable guide catheter and/or delivery catheter, as described above in reference to FIG. 11. In this approach, the guidewire may be removed prior to the introduction of the delivery catheter. The steerable guide catheter may be advanced through the septum into the left atrium and used to guide the delivery catheter through the mitral valve into the left ventricle and to the intended landing zone. In some embodiments, a steerable guide catheter may be combined with a steerable delivery catheter.

In some embodiments, as shown in FIGS. 42 to 45, the partitioning device may be alternatively delivered through a transapical approach. In a transapical approach, a device is generally delivered from the apex of the heart, in contradistinction to the orientation of transvascular delivery, as described above. Therefore, locations and orientations on the partitioning device that are "distal" in transvascular delivery may become "proximal" in transapical delivery and vice versa. As described herein, the terms "distal" and "proximal" refer to locations and orientations of the devices and procedures of the invention. The term "distal" refers to a location or direction away from a user. The term "proximal" refers to a location or direction towards a user.

Figure 42:
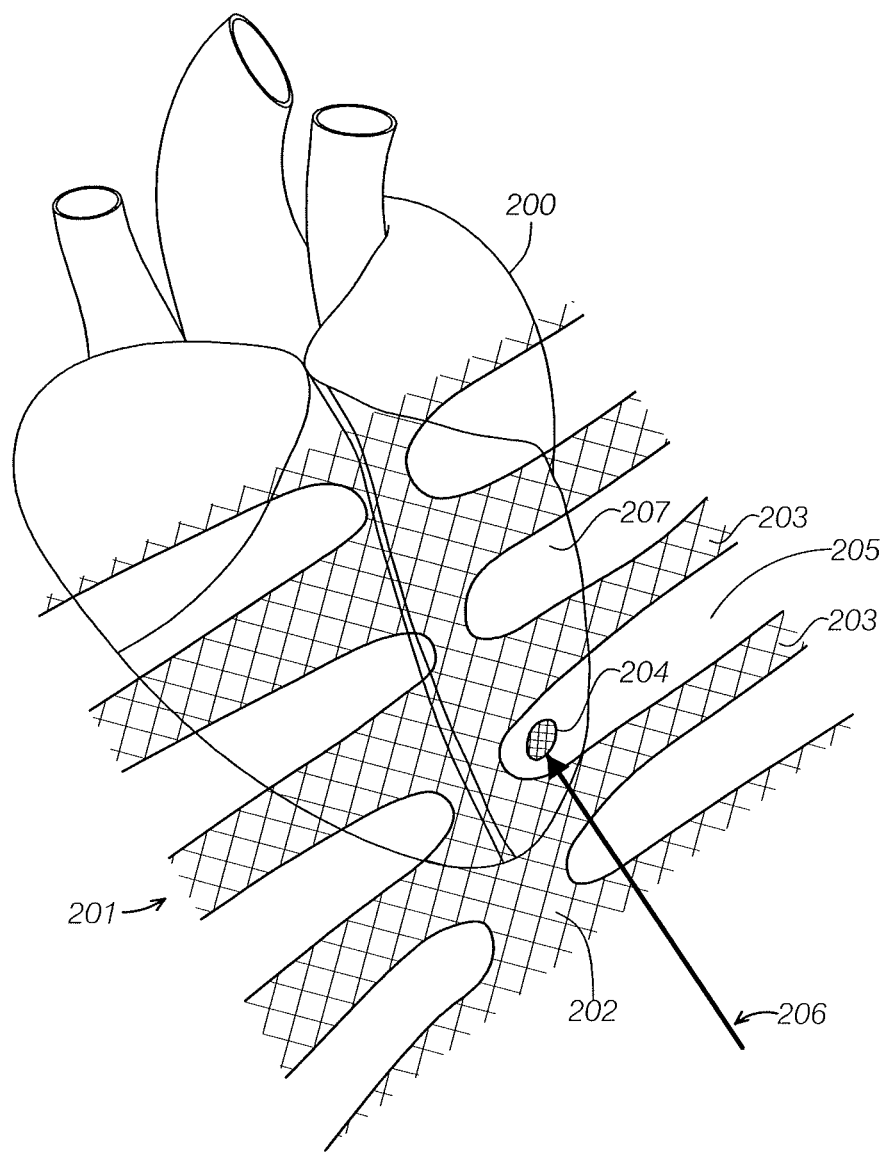
FIG. 42 illustrates a position of a transapical access zone

The transapical approach may be advantageously used in patients with extensive vascular or valvular disease, where delivery through a transvascular approach is undesirable or even unfeasible. As shown in FIG. 42, in a transapical approach, an intercostal access route to the left ventricle may be established by creating a cardiotomy near to the apex of the heart, using a surgical or a percutaneous procedure. FIG. 42 illustrates the location of a transapical access zone. A heart 200 is shown, underneath the rib cage 201, showing the sternum 202 and the ribs 203. A transapical access zone 204 is visible through the intercostal space 205. Arrow 206 illustrates a possible direction of access between the ribs and through the transapical access zone to the left ventricle 207. In an embodiment of a surgical transapical method of delivery of the device, access to the heart may be achieved by a mini-thoracotomy in an intra-costal space 205, followed by a rib spread. Access to the ventricle 207 may be achieved by micropuncture in the transapical access zone 204, and dilation of the puncture to create a cardiotomy 301 (shown in FIG. 43). A procedural access sheath (not shown) may be placed. The procedural sheath may have a function similar to a guide catheter in vascular placement of the device. In some embodiments, the procedural sheath may be a specifically designed guide catheter. The sheath or catheter may be placed with the distal end in the left ventricle 207 of the heart 200.

Figure 43:
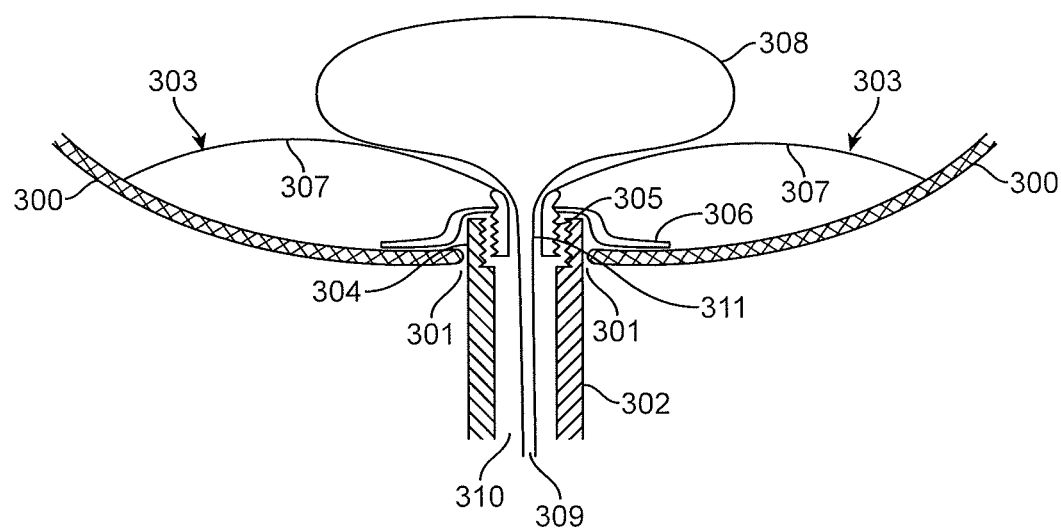
FIG. 43 illustrates an exemplary embodiment of a transapical delivery of a partitioning device into a ventricle.
Figure 44A:
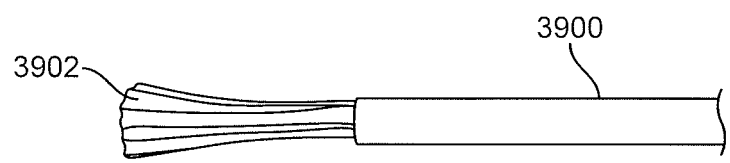
FIGS. 44A and 44B illustrate a partitioning device and delivery system embodying features of the invention and configured for delivery via a transapical approach.
Figure 44B:
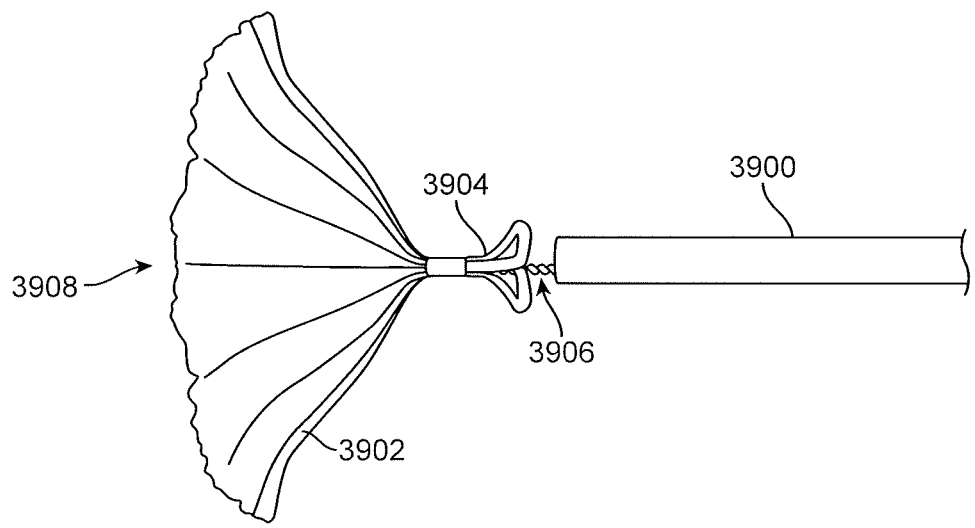

As shown in FIG. 43, an exemplary embodiment of a transapically placed partitioning device 303 is shown in position within a patient's ventricle. As shown, ventricular wall 300 may be perforated at cardiotomy 301. The cardiotomy may be located in the transapical access zone 204, as shown in FIG. 42. Returning to FIG. 43, a delivery shaft 302 may be located in the cardiotomy 301. The delivery shaft 302 may be a rigid or a flexible hollow member, like a rigid tube or a flexible catheter. The delivery shaft 302 may be connected to the partitioning device 303 on the proximal side of the device, i.e. the side of the device facing the ventricular wall. As shown in FIGS. 44A and 44B, the delivery device 3900 may be coupled to the back side of the central hub 3904 via coupling element 3906, such that the open end 3908 of the umbrella-like structure having a plurality of struts 3902 faces away from the delivery device 3900. Returning to FIG. 43, the connection may be achieved with the same coupling mechanisms described for the devices delivered by the transvascular approach described herein. For example, the coupling element may be a threaded coupler 304, as illustrated in FIG. 43. As shown, the partitioning device 303 may comprise threaded end 305, central hub 306 and ribs 307. Deployment and expansion of the partitioning device 303 may be achieved by the same mechanisms as those deployed for the device delivered by the transvascular approach described herein. However, in a transapical delivery system, an expansion member may be placed on the distal side of the partitioning device, i.e. the side of the device facing the ventricular lumen. This is illustrated for a device expanded with the aid of a balloon 308 in FIG. 43. The balloon 308 may be connected to a control device (not shown) operated by a user through an inflation lumen 309. The inflation lumen 309 may run through a continuous lumen 310 in the delivery shaft 302, and continuous lumen 311 in the partitioning device 303. The delivery shaft 302 may be a rigid tube or a flexible catheter. In some embodiments, as shown in FIG. 43, a lumen 310 may run through the delivery shaft 302 and a lumen 311 may run through the device 303 to accommodate a means for controlling an expansion member 308 located on the device 303. The device/delivery shaft assembly may be loaded into the access sheath or guide catheter in a manner analogous to the loading procedure in transvascular delivery. The device may be delivered into the ventricle 207 through the access sheath or guide catheter, and be allowed to expand or partially expand.

The access sheath or guide catheter may be withdrawn from the cardiotomy 301, allowing the ventricular wall 300 to seal against the delivery shaft 302. In some embodiments the access sheath may be a splittable sheath, to facilitate removal from the cardiotomy and the delivery shaft. The delivery shaft 302 may be moved in a proximal direction (i.e. out of the heart) in the cardiotomy 301, allowing it to pull a central hub 306 of the partitioning device onto the ventricular wall 300. In some embodiments an expansion member, such as a balloon 308 or a mechanical expansion member may be located on the device 303 in a location distal to the device, i.e. in a location facing the ventricular lumen and away from the apex. The expansion member 308 may be expanded to fully deploy and anchor the partitioning device 303. After collapsing or deflating, the expansion device 308 may be withdrawn through the continuous lumens 310 and 311. Alternatively, the expansion device may be removed together with the delivery shaft 302 after passing lumen 311. The delivery 302 shaft may be disconnected from the partitioning device 303 and withdrawn from the cardiotomy 301, and the cardiotomy 301 may be closed in a standard manner, for instance with a purse-string suture.

In some alternative embodiments of a percutaneous transapical method of delivery of the device 303, access may be achieved by direct puncture of the ventricular wall 300 at the transapical access zone 204 with a micropuncture needle, followed by advancing a guidewire (not shown) through the needle and exchanging the needle for an appropriate access sheath or a specifically designed guide catheter. Deployment of the device 303 and retrieval of the delivery shaft 302 may be similar or identical to the procedures used after surgical access. Closure of the cardiotomy 301 may be achieved with a percutaneous closure device.

Figure 45:
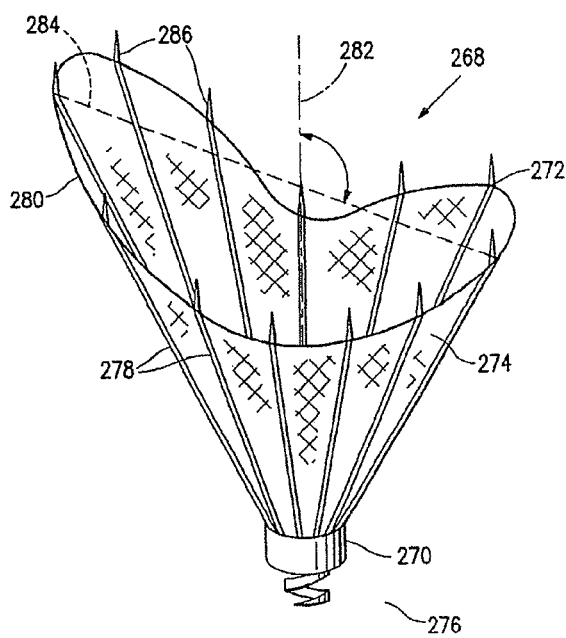
FIG. 45 illustrates one embodiment of a partitioning device in which the hub is in an asymmetric position.

During transapical access, the central hub of the partitioning device may be located co-axially with the cardiotomy. However, the cardiotomy may not be located centrally to the segment of the ventricular wall to be partitioned away from the lumen of the ventricle. Therefore, in some cases, the use of a partitioning device with an axis of symmetry at a central hub may not result in optimal coverage of an ineffective segment of the ventricular wall. In such cases, use of an asymmetric partitioning device, as illustrated in FIG. 45, and described in US patent application 20070213815, to Khairkharan et al. filed. May 7, 2007, may provide a more appropriate device configuration.

In some embodiments, as shown in FIGS. 44A and 44B, during access of the heart and delivery of the implant, the sheath 3900 may be fully deployed over the implant to hold the implant in a collapsed configuration. As shown in FIG. 44A, the sheath may be pulled back, away from the device, to begin to allow the expansion of the device. As shown in FIG. 44B, once the sheath is pulled completely off of the implant, the implant is free to fully expand, either by the nature of the implant materials and design and/or with the aid of an expansion member, such as an inflatable balloon (not shown). In some embodiments, it may be desirable to re-collapse the implant while it is within the patient. For example, a user may wish to reposition the implant or remove the implant all together. To collapse the implant, the sheath 3900 may be pushed back over the implant, thereby pushing the struts of the implant back into a collapsed or partially collapsed configuration, as shown for example in FIG. 44A.

In some embodiments of the device, radio-opaque markers may be incorporated into the device. The markers may be included on the implanted partitioning device and/or on the delivery system. Radio-opaque markers may be constructed from biocompatible heavy metals, such as gold, platinum and tantalum, and may be fabricated in any form or shape suitable for the intended device, such as bands, tabs, ribbons, disks and the like. They may be in the form of components specifically included for the purpose of providing radio-opacity, or they may be inherent components of a device, made out of a radio-opaque material to provide radio-opacity. In some embodiments, as shown in FIG. 41B, the distal end of the elongate access and/or delivery sheath 3604 for a transapical approach may include marker bands 3606 and 3608. As shown, the sheath 3604 may be delivered through the apex of the patient's heart, and the marker band 3606 may indicate the height and/or position of the anchors in their deployed configuration. Marker band 3608 may indicate the position of the central hub of the implant. Alternatively, the marker bands may be positioned on the sheath to indicate any other suitable positioning information of the implant or other component of the system.

Manufacture and Assembly

Figure 46:
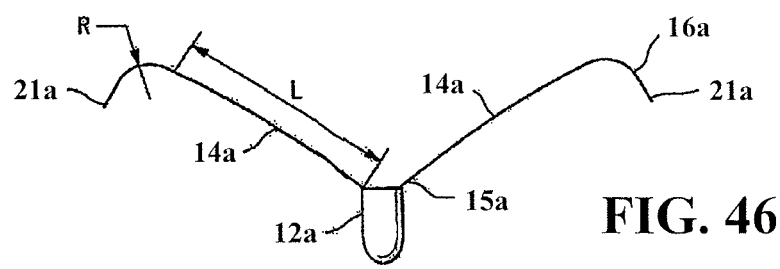
FIG. 46 is a partial schematic view of the expandable frame of the partitioning device shown in FIGS. 1 and 2 in an unrestricted configuration.
Figure 47:
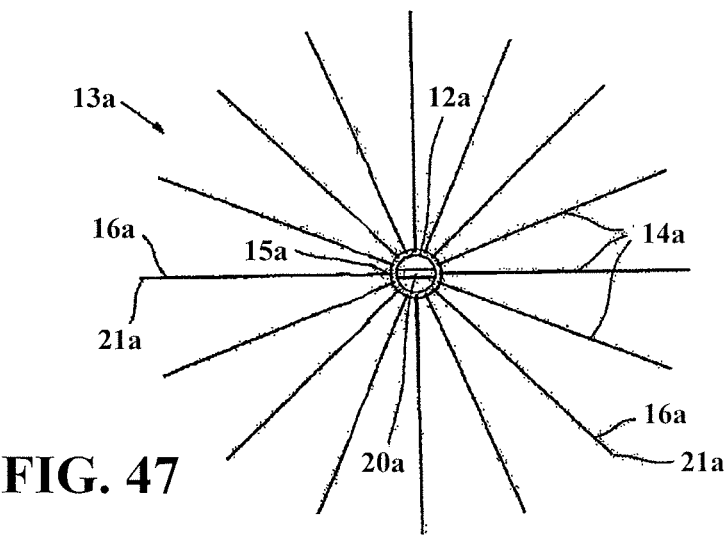
FIG. 47 is a top view of the expandable frame shown in FIG. 46.

FIGS. 46 and 47 illustrate the reinforcing frame 13a in an unstressed configuration and include the ribs 14a and the hub 12a. In some embodiments, the ribs 14a have a length L of about 1 to about 8 cm. In one embodiment, the ribs 14a have a length L of about 1.5 to about 4 cm for most left ventricle deployments. The proximal ends 16a have a flared construction. To assist in properly locating the device during advancement and placement thereof into a patient's heart chamber, parts, e.g. the distal extremity, of one or more of the ribs and/or the hub may be provided with markers at desirable locations that provide enhanced visualization by eye, by ultrasound, by X-ray, or other imaging or visualization means. Radiopaque markers may be made with, for example, stainless steel, platinum, gold, iridium, tantalum, tungsten, silver, rhodium, nickel, bismuth, other radiopaque metals, and alloys and oxides of these metals.

Figure 48:
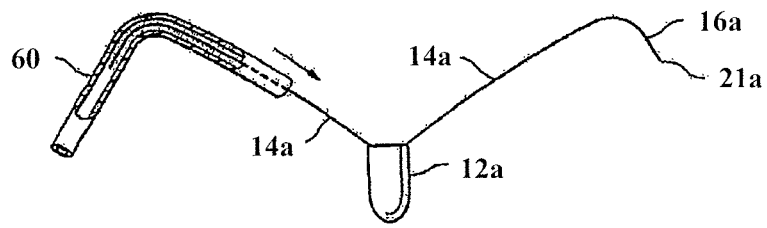
FIG. 48 is a schematic illustration of a method of forming the partitioning device shown in FIGS. 1 and 2 from the expandable frame shown in FIGS. 46 and 47.
Figure 49:
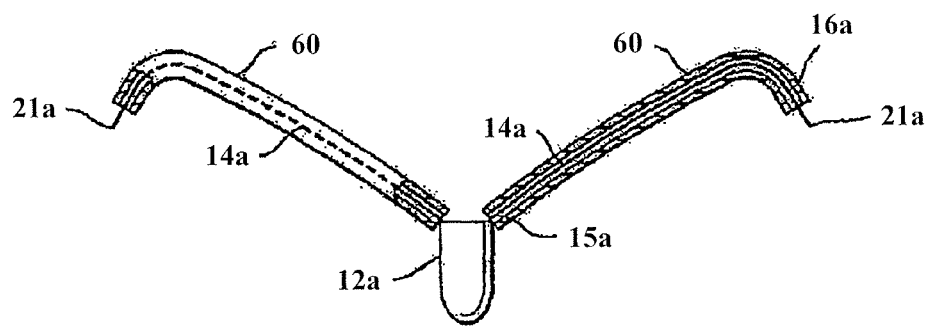
FIG. 49 is a schematic illustrations of a method of forming the partitioning device shown in FIGS. 1 and 2 from the expandable frame shown in FIGS. 46 and 47.
Figure 50:
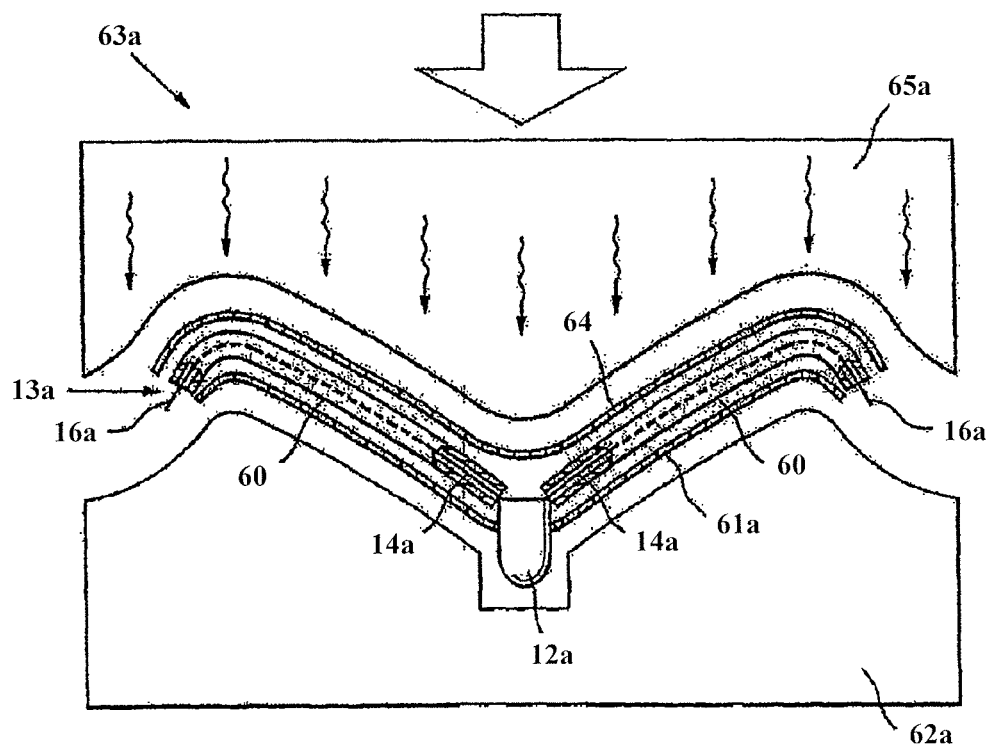
FIG. 50 is a schematic view of the assembled components shown in FIG. 49, as they are situated in a laminating press.

Embodiments of the partitioning device 10a, both unilaminar and bilaminar embodiments, are conveniently formed by placing a thermoplastic tube 60, e.g. polyethylene or high density polyethylene (HDPE), over the ribs 14a of the frame 13a as shown in FIG. 48 until the proximal ends 16a of the ribs 14a extend out the ends of the thermoplastic tubes as shown in FIG. 49, to form thermoplastic-encased ribs. Further steps in the process of forming a unilaminar or bilaminar partitioning device make use of a press or lamination mold 63*a* that includes a female platen 62*a* and a male platen 65*a*, one or both of which can be heated and cooled according to process specifics. A first expanded polytetrafluoroethylene (ePTFE) sheet 61*a* of appropriate size is placed in the female platen 62*a* of the mold or press 63*a*. The frame 13*a*, with tubes 60 slidably disposed or deployed over the ribs 14*a*, is placed in platen 62*a* on top of the ePTFE sheet 61*a*. In some alternative embodiments, the ePTFE sheet may be placed over the ribs. The center portion of the sheet 61*a* may be provided with an opening through which the hub 12*a* extends. In the case of forming a bilaminar embodiment, a second ePTFE sheet 64*a* is placed on top of the ribs 14*a* of frame 13*a* as shown in FIG. 50. The melting point of the thermoplastic material is lower than that of the ePTFE, thus the application of heat and pressure, as detailed below, is sufficient to melt the thermoplastic material but does not cause melting of the ePTFE.

Embodiments of methods to form a partitioning device that joins ePTFE sheet material, polyethylene material, and ribs into an integral structure include the application of heat and pressure. Heat and pressure may be applied through a mold or press 63*a* for a period of predetermined period of time, such as from about 30 seconds to about 360 seconds, or more particularly from about 75 seconds to about 240 seconds, or still more particularly, for about 120 seconds. Either the male platen 65*a* or the female platen 62*a*, or both male and female platens may be heated so as to attain an operating temperature of between about 260 degrees F. and 530 degrees F., particularly to a temperature between about 375 degrees F. and 520 degrees F., and more particularly to temperature between about 490 degrees F. and about 510 degrees F., and still more particularly to a temperature of about 500 degrees F. In some embodiments, the assembly may be pressed (i.e., pressured or pressurized), the applied pressure being in the range of about 10 psi to about 150 psi. In some particular embodiments, the pressure is between about 35 psi and about 120 psi, and in more particular embodiments, between about 60 psi and about 90 psi. In some embodiments, a single sheet of ePTFE is utilized to make a unilaminar device, the single sheet corresponding to the first sheet 61*a* of FIG. 50.

PTFE fabric is a woven material that varies with regard to the thickness of fibers and in the internodal distance between fibers. The presence of the space or volume between fibers provides the material with a foraminous quality which is advantageous for fusion or adhesion processes. Various forms of ePTFE have average internodal distances that vary from about one micron up to about 1,000 microns. Typical embodiments of ePTFE fabric appropriate for the manufacture of the herein described partitioning device may have internodal distances of between about 5 microns to about 200 microns, more particularly from about 10 microns to about 100 microns, and still more particularly from about 20 microns to about 50 microns. Aspects of the lamination process are described further below, and illustrated in FIGS. 51-58. Sheets may be formed of either porous or non-porous ePTFE, as well as other suitable biocompatible materials, as described elsewhere herein.

As described further below, the ePTFE fabric is typically stretched during the lamination process, under the conditions of heat and pressure that are applied by the press. Such stretching may not be uniform across the fabric surface, the maximal linear stretch in portions of the fabric may be of a magnitude of 2-fold to 4-fold. The stretching of fabric serves, in general terms, to reduce the thickness and overall collapsed profile of the device.

Figure 51A:
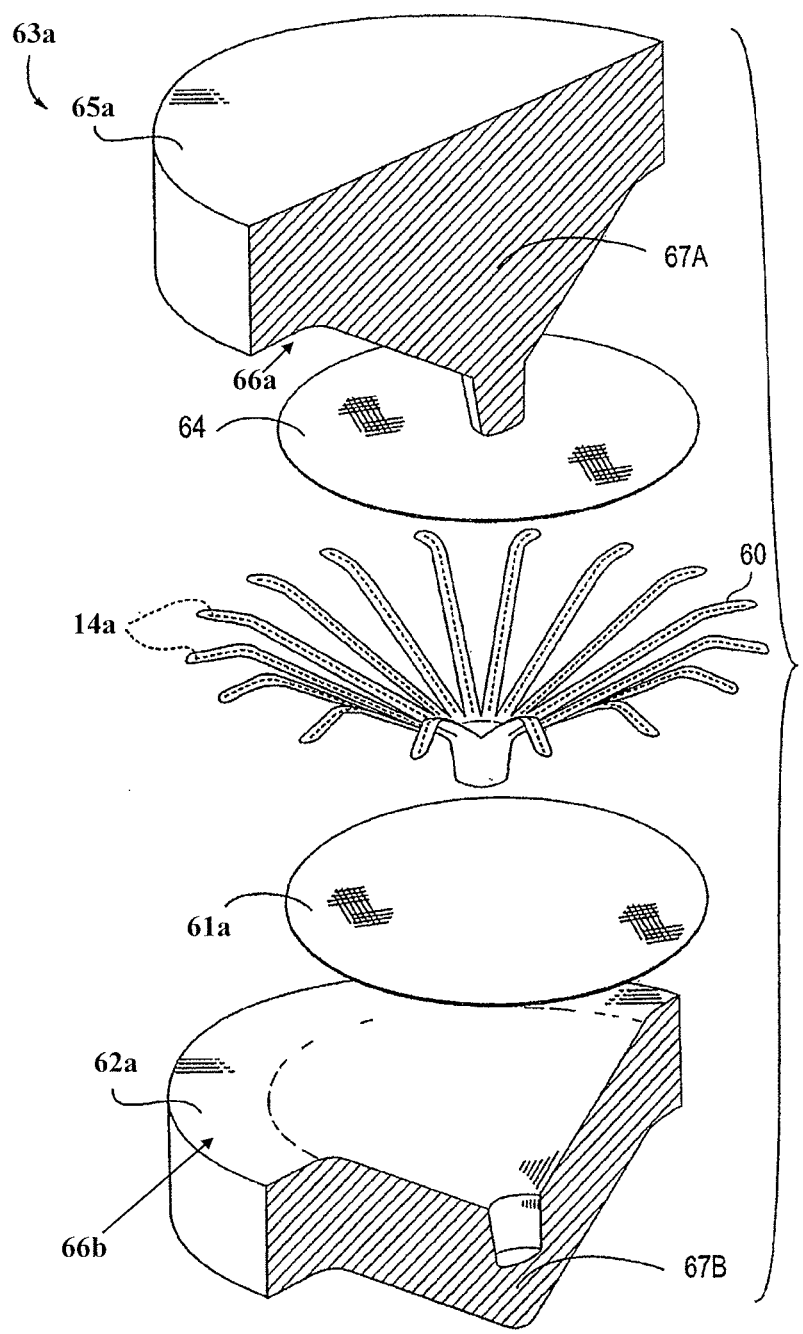
FIGS. 51A-51D include views of a bilaminar assembly for the making of an intracorporeal partitioning device, as well as views of the assembled device.
Figure 51B:
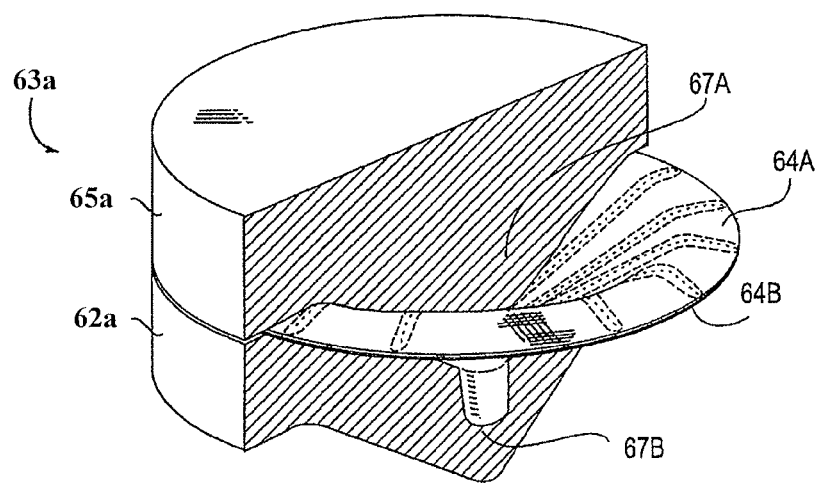
Figure 51C:
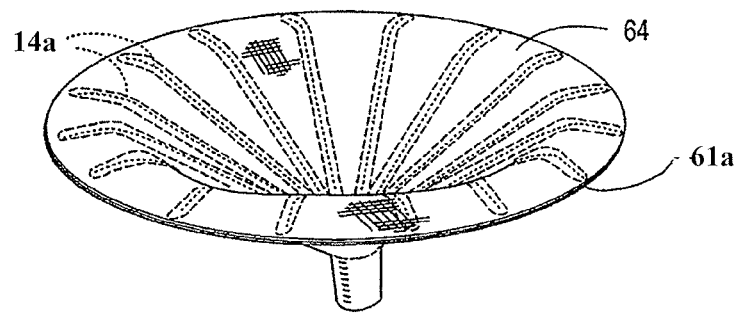
Figure 51D:
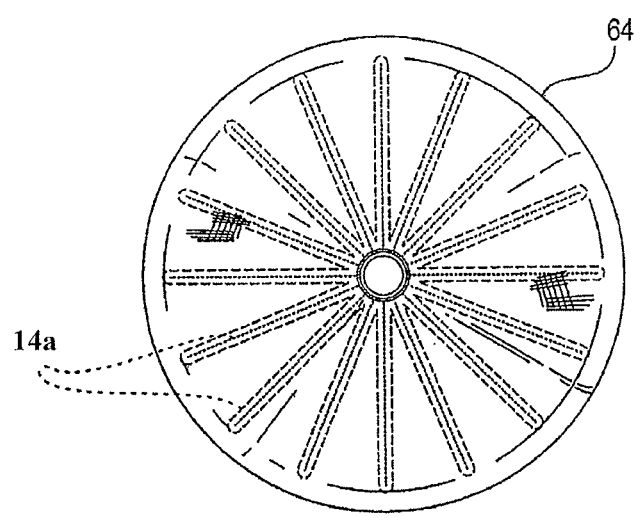

FIGS. 51A-51D include further views of a bilaminar assembly for the making of an intracorporeal partitioning device (as also depicted variously in preceding FIGS. 48-50) and views of the assembled device. FIG. 51A shows a perspective view of an exemplary device; FIG. 51B shows an exploded and partially cutaway view of the components of the device assembled for lamination; FIG. 51C provides of cutaway view of the device within the press in a closed position; and FIG. 51D provides a frontal view of the device after assembly.

In FIG. 51A, the upper or male platen 65*a* of a press 63*a* and the lower or female platen 62*a* are seen above and below, respectively, an awaiting assembly that includes, from top to bottom, a sheet of ePTFE 64, an assembly of polyethylene 60 covered ribs 14*a* that are formed into a cone-shaped configuration, and a bottom sheet of ePTFE 61*a*. Around the periphery of the upper platen 65*a* is a rim portion 66*a*, and around the periphery of the lower platen 62 is a rim portion 66*a*. These two rim portions (66*a* and 66*a*) form complementary planar surfaces which serve to hold edges of the sheets of ePTFE fabric as the central portion is being subjected to being pressed by the complementary surfaces of the central portion or shaping portion 67A of the upper platen 65*a*, and the central portion 67B of the lower platen 62*a*. The closure of the two halves of the platen is depicted in the cutaway view of FIG. 51B. A perspective view of the device as it would emerge post-formation is seen in FIG. 51C; where the polyethylene encased ribs 14*a* may be seen. A frontal plane-flattening view of the device upon removal from the press is shown in FIG. 51D, again showing the polyethylene encased ribs 14*a*, the polyethylene now reformed from its native circular configuration. Details of this structure in a before-pressing form 60 and after-pressing pressing form 60A are shown in FIGS. 52, 53, 54, and 58.

Figure 52A:
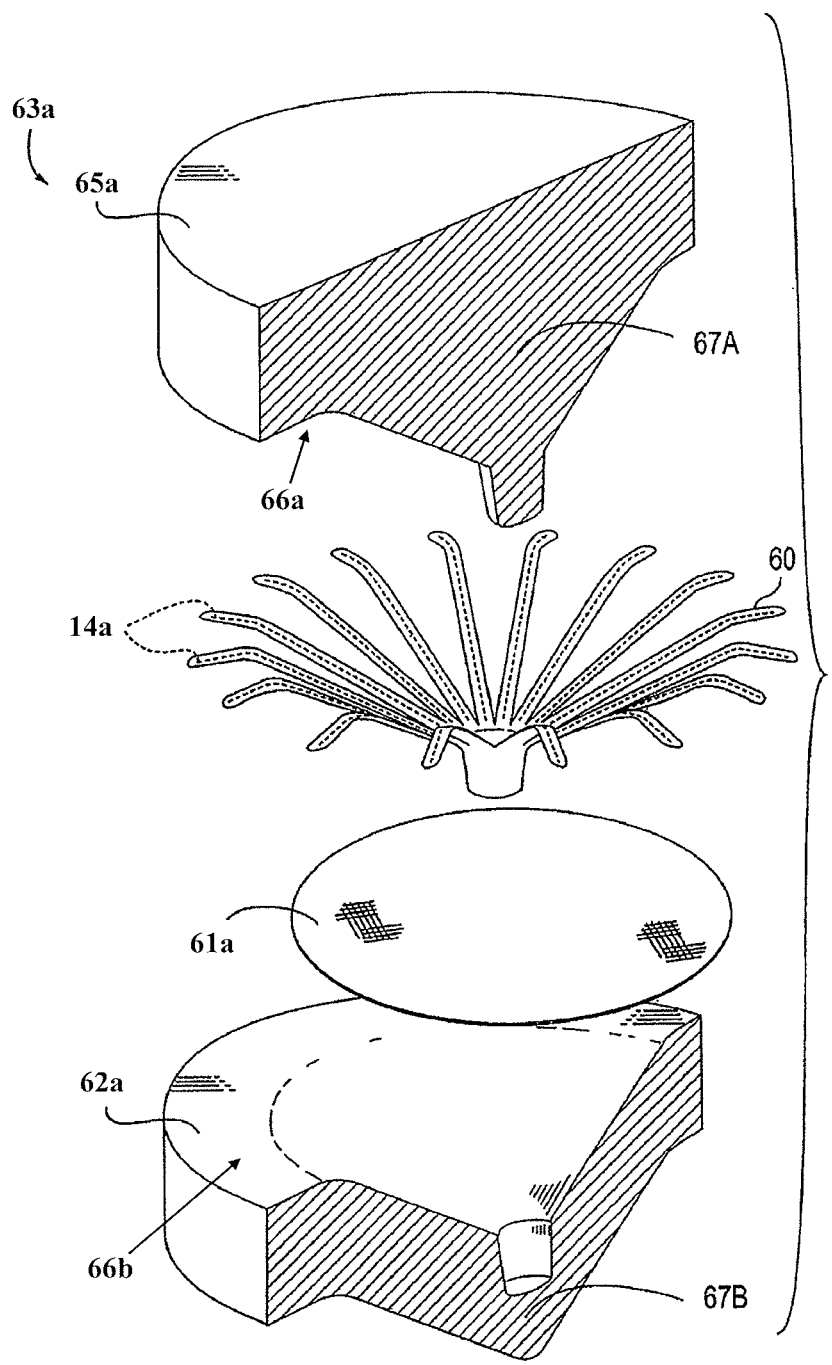
FIGS. 52A-52D include views of a unilaminar assembly for the making of an intracorporeal partitioning device, as well as views of the assembled device.
Figure 52B:
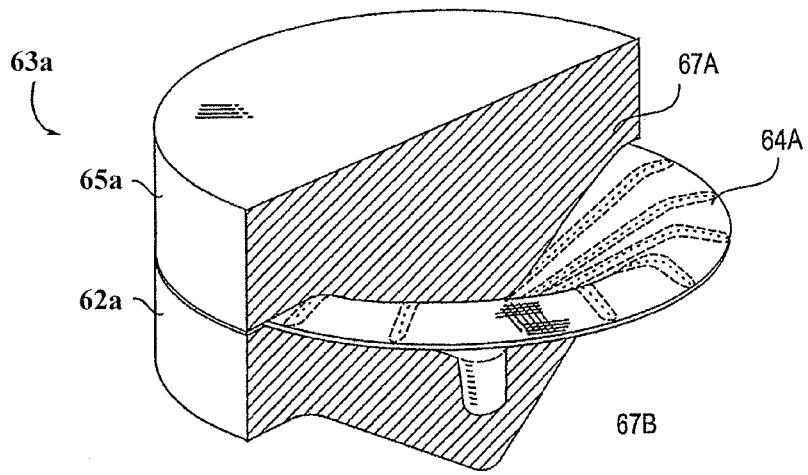
Figure 52C:
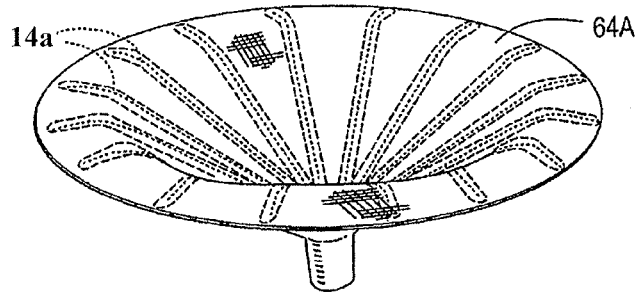
Figure 52D:
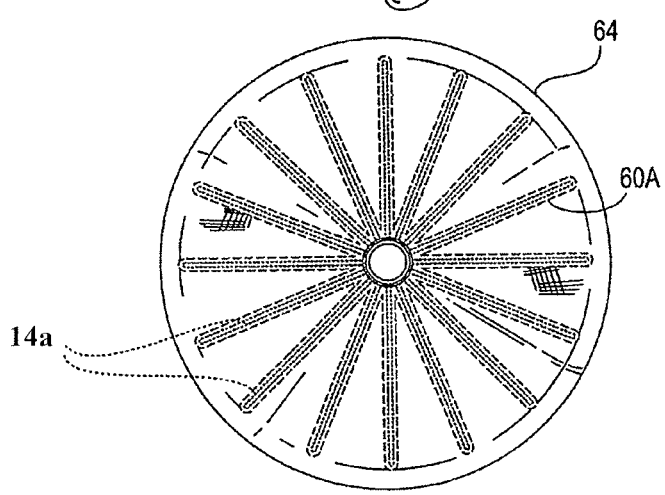

FIGS. 52A-52D include various views of a unilaminar assembly for the making of an intracorporeal partitioning device, as well as views of the assembled device. FIG. 52A shows an exploded and partially cutaway view of the components of the device assembled for lamination; FIG. 52B provides of cutaway view of the device within a press, the press in a closed position; FIG. 52C shows a perspective view of an exemplary device; FIG. 52D provides a frontal view of the device after assembly.

In FIG. 52A, the upper or male platen 65*a* of a press 63*a* and the lower or female platen 62*a* are seen above and below, respectively, an awaiting assembly that includes, from top to bottom, an assembly of polyethylene 60 covered ribs 14*a* that are formed into a cone-shaped configuration, and a bottom sheet of ePTFE 61*a* that will ultimately form a unilaminar device. Around the periphery of the upper platen 65*a* is a rim portion 66*a*, and around the periphery of the lower platen 62 is a rim portion 66*b*. These two rim portions (66*a* and 66*b*) form complementary planar surfaces which serve to hold edges of the sheets of ePTFE fabric as the central portion is being subjected to being pressed by the complementary surfaces of the central portion or shaping portion 67A of the upper platen 65*a*, and the central portion 67B of the lower platen 62*a*. The closure of the two halves of the platen is depicted in the cutaway view of FIG. 52B. A perspective view of the device as it would emerge post-formation is seen in FIG. 52C; where the polyethylene encased ribs 14*a* may be seen. A frontal plane-flattening view of the device upon removal from the press is shown in FIG. 52D, again showing the polyethylene encased ribs 60A, the polyethylene now reformed from its native circular configuration. Details of this structure in a before-pressing form 60 and after-pressing pressing form 60A are shown in FIGS. 53, 54, and 58.

An aspect of ePTFE material that relates to the internodal distances within the fabric is that such distance is preferably sufficient to accommodate the flow of melted polyethylene from the thermoplastic tubes 60 during the heating and pressuring period of embodiments of the forming process. As melted polyethylene intercalates into the ePTFE fabric and then solidifies in a reformed configuration on cooling, intermingled and interlocking zones of material continuity having been created between polyethylene and polytetrafluoroethylene (PTFE). These fusion zones of interlocking zones of material continuity provide a firm bonding matrix that (1) secures the still-polyethylene-encased rib 14a to the adjacent one ePTFE sheet (in a unilaminar embodiment) or two ePTFE sheets (in a bilaminar embodiment, and thereby within the bilaminar structure formed by the two sheets) and (2), in a bilaminar embodiment, that adheres the two ePTFE sheets together to form a bilaminar structure.

Figure 53A:
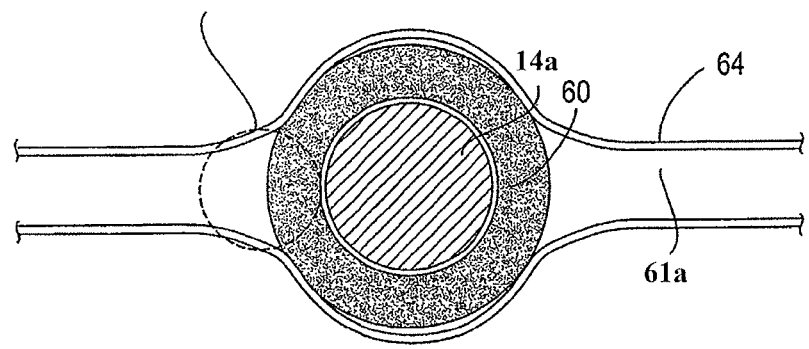
FIGS. 53A and 53B provide cross-sectional views of an assembly from which a bilaminar partitioning device is formed.
Figure 53B:
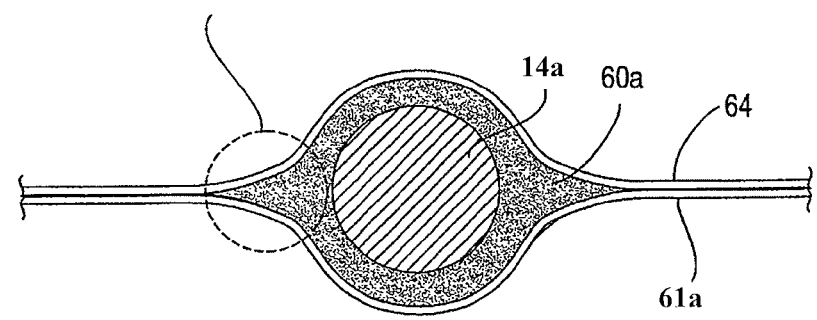
Figure 54A:
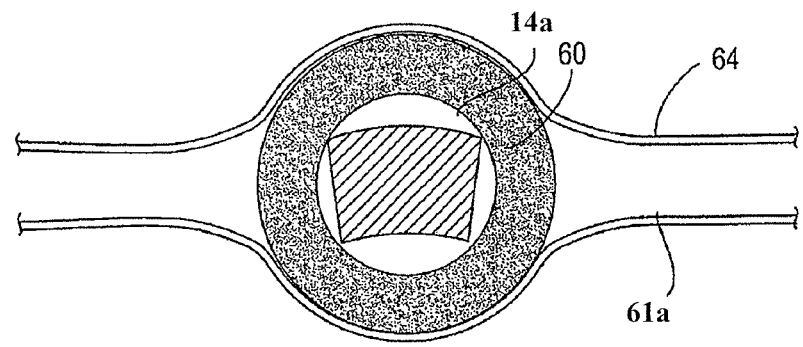
FIGS. 54A and 54B provide cross-sectional views of an assembly from which a bilaminar partitioning device is formed.
Figure 54B:
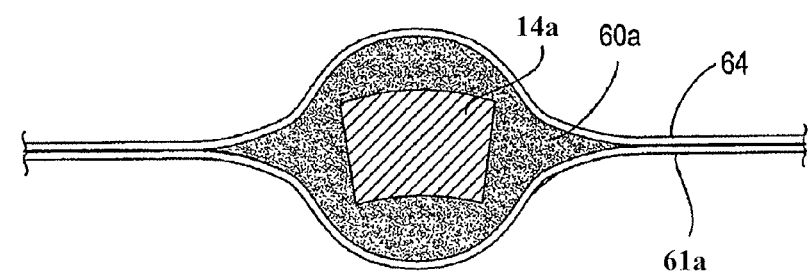

FIGS. 53 and 54 provide views of two embodiments of a metallic rib encased in a polyethylene tube 60, prior to (A) and subsequent to (B) being fused within two ePTFE sheets (61a and 64), to form a bilaminar dPTFE sheet, the two sheets adhering to each other in the locale of the zone of fusion between the polyethylene and the ePTFE materials. FIGS. 53A and 53B depict a rib 14a that is substantially circular in cross section. Similar embodiments (not shown) include those with cross sectional profiles that are somewhat flattened or elliptical. The cross sectional profile of ribs may vary, and various embodiments may provide advantages with regard, for example, to stiffness or to practical aspects of the assembly of the device. Other embodiments of ribs are more rectangular in cross section. FIGS. 54A and 54B depict a rib 14a that is generally rectangular in cross section, though curved or arched as a whole in cross section in this particular embodiment, with a convex upper-facing surface and a concave lower-facing surface.

FIG. 53A provides a cross sectional view of a metallic rib 14a, substantially circular in cross section, encased in a polyethylene tube 60, the tube disposed between the two ePTFE sheets 61a and 64 prior to application of pressure and heat. FIG. 53B provides a view of the same materials after heat and pressure to form a bilaminar device. The thermoplastic material that originally comprised tube 60 disposed over the rib 14, has reformed as polyethylene material 60A, which is fused into the porous matrix of the ePTFE sheets 61 and 64. The polyethylene material represented by 60 in its native form and by 60A in its post-melt and reformed form is substantially conserved in terms of total volume, but it is redistributed as schematically depicted in FIGS. 53A-53B, as well as in FIGS. 54-58. In addition to the schematically depicted polyethylene 60 and 60A, also depicted schematically and not necessarily to scale are the relative sizes of the ribs 14a and the PTFE fabric 64. The first and second ePTFE sheets thereby form a bilaminar ePTFE sheet, and at sites where the bilaminar sheet surrounds the thermoplastic material; the bilaminar ePTFE and the thermoplastic material solidify, thereby securing the sheets 61a and 64 to the ribs 14a and preventing their delamination during use of the partitioning device. The encircled detail within FIG. 53A that is labeled 58A' is a reference to FIG. 58A which provides a more detailed of the ePTFE and polyethelene materials prior to their fusion during the lamination process, as described below. The encircled detail within FIG. 53B that is labeled 58B' is a reference to FIG. 58B which provides a more detailed of the ePTFE and polyethelene materials after their fusion during the lamination process, as described below.

FIGS. 54A and 54B provide a representation of an embodiment of the device wherein the rib 14a is substantially rectangular in cross section, but wherein the process of forming a device is otherwise substantially parallel to the sequence shown in FIGS. 53A and 53B. FIG. 54A provides a cross sectional view of a metallic rib 14a, substantially rectangular in cross section, encased in a polyethylene tube 60, the tube disposed between the two ePTFE sheets 61a and 64 prior to application of pressure and heat to form a bilaminar device. FIG. 54B provides a view of the same materials after heat and pressure. The thermoplastic material that originally comprised tube 60 disposed over the rib 14a has reformed as polyethylene material 60A, which is fused into the porous matrix of the ePTFE sheets 61a and 64. The first and second ePTFE sheets thereby form a bilaminar ePTFE sheet, and at sites where the bilaminar sheet surrounds the thermoplastic material; the bilaminar ePTFE and the thermoplastic material solidify, thereby securing the sheets 61a and 64 to the ribs 14a and preventing their delamination during use of the partitioning device. Sheets may be formed of either porous or non-porous ePTFE, as well as other suitable biocompatible materials, as described further below.

In embodiments where only a single sheet of ePTFE is used, a unilaminar structure is formed, with the ribs 14a adhering to the ePTFE sheet 61a by way of the melted and reformed polyethylene that originally comprised the thermoelastic tube 60 surrounding rib 14a. These unilaminar embodiments are described further below, and depicted in FIGS. 55 and 56. In both cases, i.e., the unilaminar and bilaminar embodiments, the reforming of the polyethylene which originally encases the rib 14a to a configuration that intercalates through the ePTFE weave, it is the reformation of the polyethylene that is substantially responsible for the integration of the ePTFE and the polyethylene-encased ribs(s) into an integrated structure.

Figure 55A:
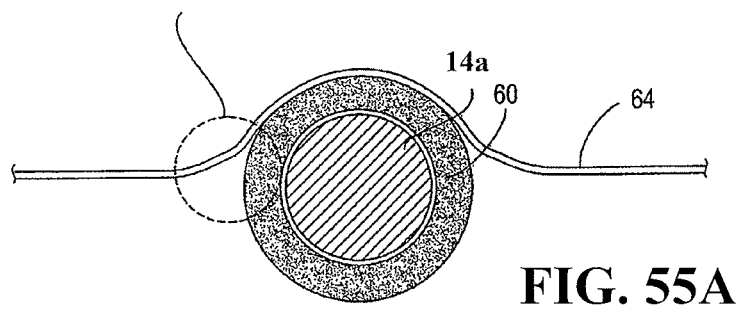
FIGS. 55A and 55B provide cross-sectional views of an assembly from which a unilaminar partitioning device is formed.
Figure 55B:
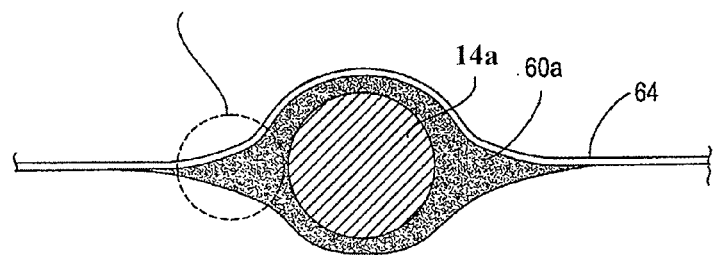

In embodiments where only a single sheet of ePTFE is used, a unilaminar structure is formed, with the ribs 14a adhering to the single ePTFE sheet 61a by way of the melted and reformed polyethylene that originally comprised the thermoelastic tube 60 surrounding rib 14a, the polyethylene material still encasing the rib. Unilaminar embodiments of the invention are depicted in FIGS. 55 and 56. FIG. 55A shows a cross sectional view of a rib 14a, substantially circular in cross section, encased in a polyethylene tube 60, the tube disposed adjacent to ePTFE sheets 64 prior to application of pressure and heat. FIG. 55B provides a view of the same materials after application of heat and pressure. The thermoplastic material that originally comprised tube 60 disposed over the rib 14a has fused into the porous matrix of the ePTFE sheet 64.

The encircled detail within FIG. 55A that is labeled 57A' is a reference to FIG. 57A which provides a more detailed of the ePTFE and polyethelene materials prior to their fusion during the lamination process, as described below. The encircled detail within FIG. 55B that is labeled 57B' is a reference to FIG. 57B, which provides a more detailed view of the ePTFE and polyethelene materials after their fusion during the lamination process, as described below.

Figure 56A:
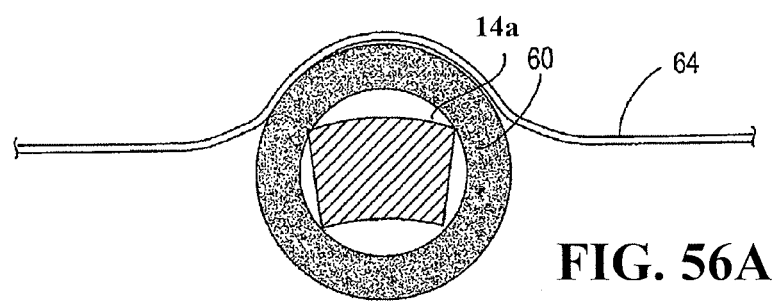
FIGS. 56A and 56B provide cross-sectional views of an assembly from which a unilaminar partitioning device is formed.
Figure 56B:
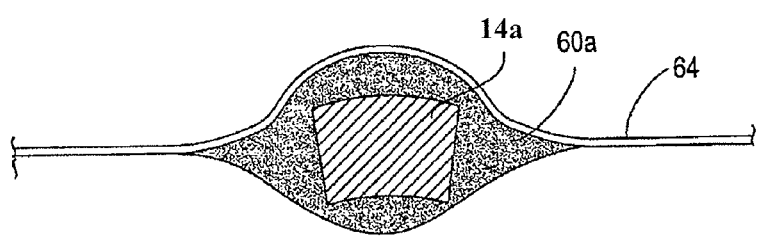

Similarly, FIG. 56A shows a cross sectional view of a rib, generally rectangular in cross section, encased in a polyethylene tube 60, the tube adjacent to ePTFE sheet 64 prior to application of pressure and heat. FIG. 56B provides a view of the same materials after heat and pressure. The thermoplastic material that originally comprised tube 60 disposed over the rib 14a has fused into the porous matrix of the ePTFE sheet 64.

In some embodiments of the method, a cooling step is applied following the application of pressure and heat. A relatively passive cooling method is appropriate for some embodiments, and can be achieved by simply placing the mold on a cold surface (for example, a chilled block of copper) or by submerging it in any suitable cold medium such as chilled water. In other embodiments, more active, permeative, or quick cooling is preferred, and may be accomplished by circulating any suitable coolant (for example, chilled water, liquid nitrogen) through cooling channels built into the lamination mold body to bring the temperature into a range of about 0 degrees F. to about 32 degrees F.

While porous ePTFE material is included in typical embodiments, non-porous ePTFE may be appropriate for some embodiments. The choice of using non-porous or porous ePTFE depends on the intended use or desired features when the partitioning device is placed in the heart. A porous membrane can advantageously function as a filter-like barrier that allows blood through-flow, but blocks transit of particles or emboli. On the other hand, in some medical applications it may be desirable to form a significant seal between two cardiac compartments with the intervention of the partitioning device, in which case a non-porous ePTFE may be preferred.

Further, the membrane 11a may also be formed of other suitable biocompatible polymeric materials such as, by way of example, may include Nylon, PET (polyethylene terephthalate), and polyesters such as Hytrel. The membrane 11a may advantageously be foraminous in nature to facilitate tissue ingrowth after deployment within the patient's heart, and further, to provide an advantageous matrix for bonding with melted polyethylene material, as for example, from a thermoplastic tube 60. The delivery catheter 32 and the guiding catheter 31 may be formed of suitable high strength polymeric material such as, by way of example, polyetheretherketone (PEEK), polycarbonate, PET, and/or Nylon. Braided composite shafts may also be employed.

FIGS. 57 and 58 provide schematic views of the lamination zones of the device, at microscopic scale. Embodiments of the porous or foraminous ePTFE sheets may have internodal distances between woven fabric strands that range between about 5 and about 200 microns, as described above. The internodal areas delineated by the fibers also provide space into which polyethylene material from the thermoplastic tubes 60 intercalates as it melts and reforms during embodiments of the lamination process. As melted polyethylene material intercalates into the unmelted ePTFE material and then solidifies into a reformed configuration on cooling, intermingled and interlocking zones of respective material-material continuity are created between polyethylene and polytetra-fluoro-ethylene (PTFE). The continuity of the PTFE fibers remains substantially unchanged, even though the fibers may be stretched, and the polyethylene forms a continuous solid that includes the PTFE fibers within it. These interlocking zones of material continuity provide a firm bonding matrix that both (1) adheres the two sheets of the bilaminar structure together, and (2) secures the rib 14a to and within the bilaminar structure. The formation of integrated laminar structures that include one or two ePTFE sheets and thermoplastic material entrapping a rib is depicted in FIGS. 57 and 58; these are schematic views, drawn such that the internodal distances appear at a scale that is larger than that of the device as a whole.

Figure 57A:
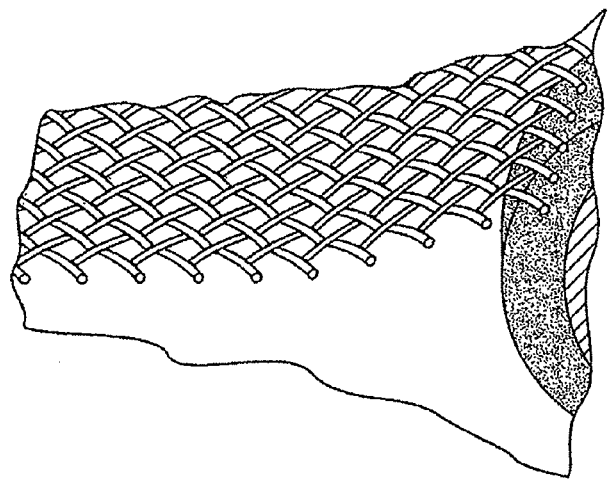
FIGS. 57A and 57B schematically depict the formation of a unilaminar integrated structure from the polyethylene-encased rib and ePTFE material by the melting and solidified reformed polythethylene to create interlocking continuities between the ePTFE and the polyethylene. This structure also depicts a portion of a larger bilaminar structure, such as a portion immediately overlaying a rib.
Figure 57B:
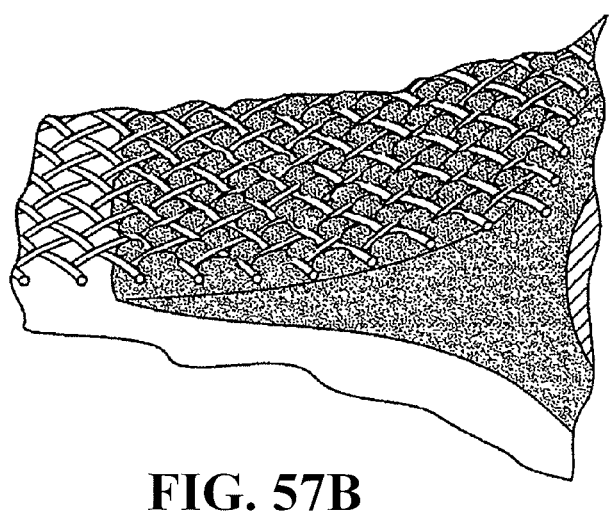

FIGS. 57A and 57B schematically depict the formation of a unilaminar integrated structure from the polyethylene-encased rib and ePTFE material by the melting and solidified reformed polythethylene to create interlocking continuities between the ePTFE and the polyethylene. This structure also depicts a unilaminar or split-laminar portion of a larger bilaminar structure, such as a portion immediately overlaying a rib 14a. FIG. 57A depicts a woven sheet of ePTFE disposed over or adjacent to a portion of the wall of a polyethylene tube encasing a rib before being subjected to pressure and heat within a press. FIG. 57B depicts the unified structure after the application of heat and pressure, and after the polyethylene has melted and reformed within and around the weave of the ePTFE fabric.

Figure 58A:
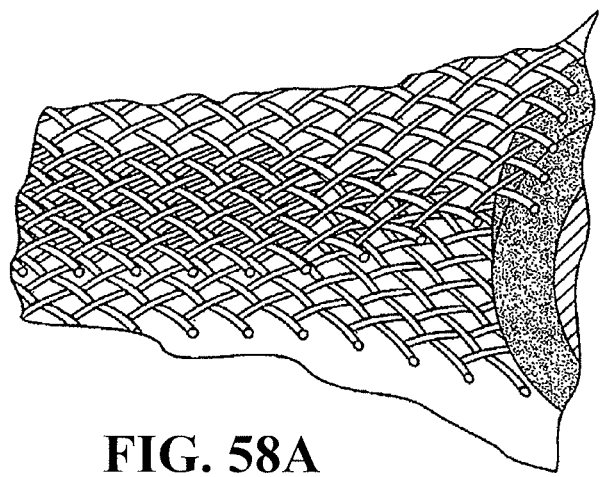
FIGS. 58A and 58B schematically depict the formation of a bilaminar integrated structure from the polyethylene-encased rib and ePTFE material by the melting and solidified reformed polythethylene to create interlocking continuities between the ePTFE and the polyethylene.
Figure 58B:
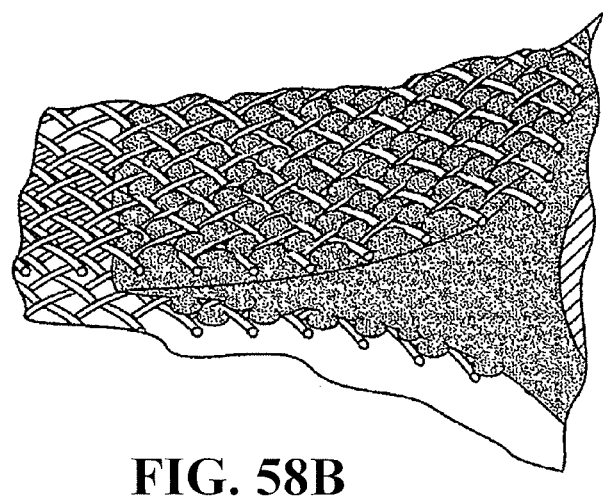

FIGS. 58A and 58B schematically depict the formation of a bilaminar integrated structure from the polyethylene-encased rib and ePTFE material by the melting and solidified reformed polythethylene to create interlocking continuities between the ePTFE and the polyethylene. FIG. 58A depicts two woven sheets of ePTFE disposed, respectively, over and under a portion of the wall of a polyethylene tube encasing a rib before being subjected to pressure and heat within a press. FIG. 58B depicts the unified structure after the application of heat and pressure, and after the polyethylene has melted and reformed within and around the weave of the ePTFE fabric. This bilaminar structure occurs in areas not immediately overlaying a rib 14a, but rather in the area that lies immediately adjacent to a rib 14a, and spreading out peripherally, thereby creating a substantial area of mutual connection between the two ePTFE sheets.

FIG. 59 shows an exploded and partially cutaway view of the components of the assembly for lamination. FIG. 59 illustrates an alternative embodiment of an assembly for the making of an intracorporeal partitioning device, wherein the device is laminated in a partially compressed, i.e. not-free state. This assembly may be configured to assemble either a unilaminar or bilaminar device. The assembly depicted in FIG. 59 is similar to the assemblies described above with references to FIGS. 51 and 52, however the assembly of FIG. 59 is configured to laminate the device in its non-free state.

As described above in reference to FIGS. 51 and 52, the implants are assembled, or laminated, in their free, heat shaped configuration. A resulting device 2300 is shown in FIG. 60A, having a free diameter of X, for example. The devices described herein are generally configured for implantation into a ventricle of a patient's heart. In some embodiments, the patient's ventricle may be smaller in diameter than the free size of the device, or more specifically, smaller than the diameter X, as shown in FIG. 60A. In some specific cases, the diameter of the ventricle may be 20 to 30% smaller than the free diameter X of the device 2300. For example, in a healthy heart, the end-diastolic dimension of the left ventricle may range from 36-56 mm and the end-systolic dimension of the left ventricle may range from 20-40 mm (A left ventricle in heart failure would typically have larger dimensions). Therefore, once implanted, a device laminated in its free state would likely be held in a contracted position (i.e. a loaded configuration with a decreased diameter) and not return to a free state and its free, or unloaded, dimension (e.g. diameter). Therefore, the membrane material will likely bunch between the struts to accommodate the device moving into the contracted state upon implantation. Excess membrane material may lead to, at least, a more expensive device, a larger collapsed configuration (necessitating larger guide and delivery catheters), improper sealing or engagement with the ventricle wall, and/or a combination thereof. Therefore, it may be desirable, in some configurations to laminate the frame of the device in a pre-loaded, or non-free, state, thereby reducing the amount of membrane material utilized to laminate the device.

In FIG. 59, the upper or male platen 2205 of a press 2203 and the lower or female platen 2202 are seen above and below, respectively. As described elsewhere herein, around the periphery of the upper platen 2205 is a rim portion, and around the periphery of the lower platen 2202 is a rim portion. These two rim portions form complementary planar surfaces which serve to hold edges of the sheets of ePTFE fabric as the central portion is being subjected to being pressed by the complementary surfaces of the central portion or shaping portion 2207A of the upper platen 2205, and the central portion 2207B of the lower platen 2202. A perspective view of the device as it would emerge post-formation is seen in FIG. 60A. A comparison of the assembly in FIG. 59 and FIG. 51 or 52 will show that the shaping portions 2207A, 2207B have a steeper angle than the shaping portions 67A and 67B in FIGS. 51 and 52. Furthermore, the height of the assembly (and the resulting device) is taller in the assembly of FIG. 59. The assembly of FIG. 59 thereby holds the device components (particularly the frame) in a pre-loaded configuration with a decreased diameter. Furthermore, as shown by line 2208, the curve of the shaping elements 2207A and 2207B may follow the curve the struts will undergo in their pre-loaded configuration. Alternatively, an assembly with a straight (not-curved 2208) shaping element may be utilized, however, in some instances; a straight shaping element may over constrain the struts in their pre-loaded configuration.

As shown in FIG. 60B, a device resulting from the assembly fixture shown in FIG. 59 has a diameter X' which is smaller than diameter X as shown in FIG. 60A, and a height Y' which is taller than Y as shown in FIG. 60A. In one specific example, an implant with diameter X equal to 85 mm might be compared to an implant with diameter X' equal to 75 mm. In some embodiments, it may be noted that devices assembled in a pre-loaded state, may have increased stability and/or a decreased propensity to inverting (flipping inside out) during delivery, implantation, and/or the life of the device.

Figure 61A:
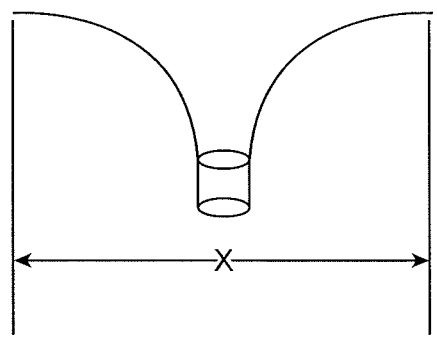
FIGS. 61A-61C illustrate a cross-section of a loaded frame in its free state (FIG. 61A), after lamination (FIG. 61B), and implanted (FIG. 61C).
Figure 61B:
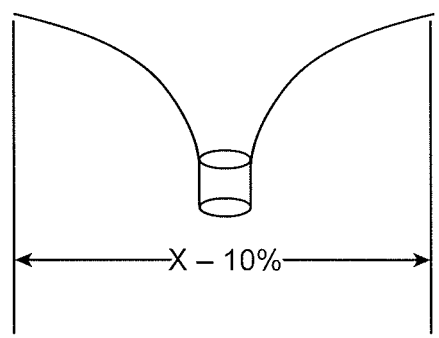
Figure 61C:
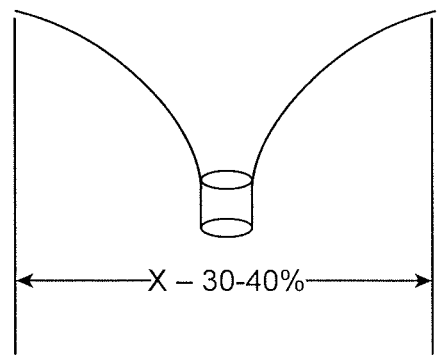

FIGS. 61A-61C illustrate a cross-section of a loaded frame in its free state or unstressed configuration (FIG. 61A), after lamination with an assembly fixture as shown in FIG. 59 (FIG. 61B), and implanted (FIG. 61C). The frame as shown in FIG. 61A may be compared to the device shown in FIGS. 46 and 47, which illustrate the reinforcing frame 13 in an unstressed configuration and include the ribs 14 and the hub 12. The ribs 14 have a length L of about 1 to about 8 cm, preferably, about 1.5 to about 4 cm for most left ventricle deployments. The proximal ends 16 have a flared construction. As shown in FIG. 61A, the frame in its free, pre-assembled state, may have a diameter of X (e.g. 80 mm). As shown in FIG. 61B, the frame in its pre-loaded, assembled state, may have a diameter of X−10% (e.g. 72 mm). For example, the frame may be pre-loaded by 10% in the assembly fixture. As shown in FIG. 61C, the frame in its loaded, implanted state, may have a diameter of X−30-40% (e.g. 56-64 mm). For example, the frame may be pre-loaded an additional 20-30% in the patient's ventricle, specifically during diastole. Although percentages of loading and/or pre-loading and diameter reduction are listed by way of providing exemplary loading configurations, such examples are for purposes of clarity of understanding only, and are not intended to be limiting. It should be understood that the frame may be loaded and/or pre-loaded and reduced in diameter to any suitable size and configuration.

Figure 62A:
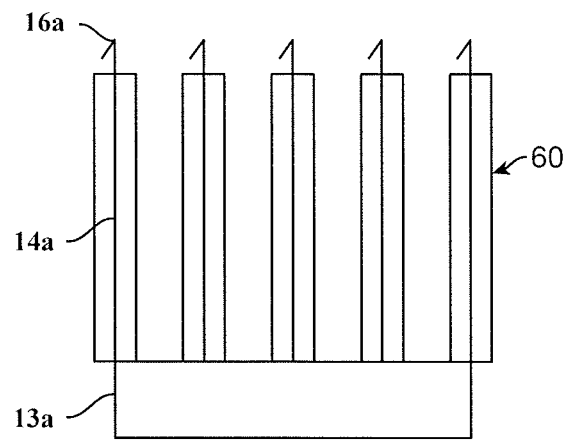
FIGS. 62A-62C illustrate a first, second, and third embodiment showing the frame of the device described herein having sleeves. As shown, the device may include full sleeves disposed along the full length of the struts (FIG. 62A), partial sleeves staggered along the length of the struts (FIG. 62B), or shortened sleeves (FIG. 62C).
Figure 62B:
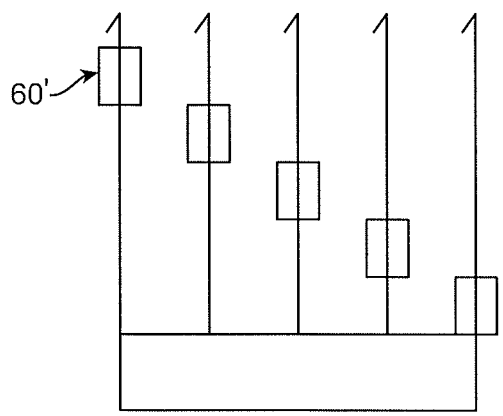
Figure 62C:
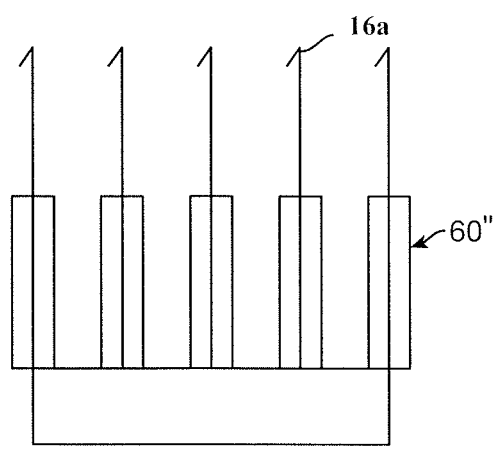

As described above, embodiments of the partitioning device 10a, both unilaminar and bilaminar embodiments, are conveniently formed by placing a thermoplastic tube 60, e.g. polyethylene or high density polyethylene (HDPE), over the ribs 14a of the frame 13a as shown in FIG. 62A until the proximal ends 16a of the ribs 14a extend out the ends of the thermoplastic tubes to form thermoplastic-encased ribs. FIGS. 62A-62C illustrate a first, second, and third embodiment showing the frame of the device described herein having sleeves, or more specifically thermoplastic tubes 60. As shown, the device may include full sleeves 60 disposed along the full length of the struts (FIG. 62A), partial sleeves 60' staggered along the length of the struts (FIG. 62B), or shortened sleeves 60" (FIG. 62C). As shown in FIG. 62B, by reducing the amount of tubing used, and by staggering the positioning of the tubing along the length of the struts 14a, the implants collapsed profile may be reduced. As shown in FIG. 62C, a reduction in profile could also be accomplished by shortening the length of the tubes, keeping them away from the perimeter of the device, or proximal ends 16a of the ribs 14a, where most of the profile size is accumulated. In an alternative embodiment, a frame may be disposed between two sheets, and the sheets may be fused together to form the assembled implant without the need for sleeves, or more specifically thermoplastic tubes. For example, a method of securing a polymeric sheet to rib components of a frame structure may include the steps of providing an assembly, the assembly comprising a frame structure disposed between a first and second polymeric sheet; and heating the assembly under pressure to fuse the first polymeric sheet to the second polymeric sheet around the frame structure to form a fused sheet. In some embodiments, the polymeric sheets of material may be ePTFE.

Unless defined otherwise, all technical terms used herein have the same meanings as commonly understood by one of ordinary skill in the art of interventional cardiology. Specific methods, devices, and materials are described in this application, but any methods and materials similar or equivalent to those described herein can be used in the practice of the present invention. While embodiments of the invention have been described in some detail and by way of exemplary illustrations, such illustration is for purposes of clarity of understanding only, and is not intended to be limiting. Various terms have been used in the description to convey an understanding of the invention; it will be understood that the meaning of these various terms extends to common linguistic or grammatical variations or forms thereof. It will also be understood that when terminology referring to devices or equipment has used trade names, brand names, or common names, that these names are provided as contemporary examples, and the invention is not limited by such literal scope. Terminology that is introduced at a later date that may be reasonably understood as a derivative of a contemporary term or designating of a subset of objects embraced by a contemporary term will be understood as having been described by the now contemporary terminology. Further, any one or more features of any embodiment of the invention can be combined with any one or more other features of any other embodiment of the invention, without departing from the scope of the invention. Still further, it should be understood that the invention is not limited to the embodiments that have been set forth for purposes of exemplification, but is to be defined only by a fair reading of claims that are appended to the patent application, including the full range of equivalency to which each element thereof is entitled.

Terms such a "element", "member", "device", "section", "portion", "step", "means" and words of similar import, when used herein shall not be construed as invoking the provisions of 35 U.S.C. .sctn.112(6) unless the following claims expressly use the terms "means" followed by a particular function without specific structure or "step" followed by a particular function without specific action. All patents and patent applications referred to above are hereby incorporated by reference in their entirety.

What is claimed is:

1. A method of reducing ventricular volume to treat heart disease, the method comprising:
    positioning an umbrella-shaped; expandable partitioning device having a reinforced membrane on a rib structure in a contracted configuration near an apex of a patient's ventricle using an elongate delivery catheter to which the partitioning device is releasably coupled;
    expanding the partitioning device by expanding an expansion member comprising an expandable structure of the delivery catheter proximal to a distal end of the delivery catheter to apply pressure to a proximal end region of the contracted partitioning device; and
    releasing a coupling element distal to the expansion member on the delivery catheter to deploy the partitioning device.

2. The method of claim 1 further comprising securing a periphery of the partitioning device to a wall of the ventricle.

3. The method of claim 1 further comprising sealing a periphery of the partitioning device to a wall of the ventricle.

4. The method of claim 1 further comprising percutaneously guiding the partitioning device on the distal end of the delivery catheter into the patient's ventricle.

5. The method of claim 1 further comprising advancing the partitioning device into the patient's ventricle through an inner lumen of a guide catheter.

6. The method of claim 1, wherein expanding the partitioning device by expanding the expansion member further comprises expanding an inflatable expansion member near the distal end of the delivery catheter.

7. The method of claim 1, wherein expanding the partitioning device by expanding the expansion member comprises expanding a plurality of discrete arms of the delivery catheter, joined at their proximal and distal ends, by bringing the proximal and distal ends closer together.

8. The method of claim 1, wherein releasing a coupling element comprises rotating a torque shaft to withdraw a helical coil screw from a hub of the partitioning device.

9. The method of claim 1 further comprising pulling pull wire to expand the expansion member.

10. The method of claim 1 further comprising rotating a torque shaft of the delivery catheter to release the coupling element from the partitioning device.

11. The method of claim 1, wherein the expandable structure of the delivery catheter is self-expanding and comprises a shape memory material.

12. A method of reducing ventricular volume to treat heart disease, the method comprising:
    positioning an umbrella-shaped, expandable partitioning device having a reinforced membrane in a contracted configuration near the apex of a patient's ventricle using an elongate delivery catheter to which the partitioning device is releasably coupled;
    expanding a mechanical expander comprising an expandable structure of the delivery catheter proximal to a distal end of the delivery catheter to apply pressure to a proximal end region of the contracted partitioning device to expand the partitioning device; and
    releasing a coupling element distal to the mechanical expander on the delivery catheter to deploy the partitioning device.

13. The method of claim 12, wherein the mechanical expander comprises a plurality of discrete arms.

14. The method of claim 12 further comprising securing the partitioning device against a wall of the ventricle to create a seal.

15. The method of claim 12 further comprising percutaneously guiding the partitioning device on the distal end of the delivery catheter into the ventricle.

16. The method of claim 12 further comprising advancing the partitioning device into the ventricle through an inner lumen of a guide catheter.

17. The method of claim 12, wherein releasing a coupling element comprises rotating a torque shaft to withdraw a helical coil screw from a hub of the partitioning device.

18. The method of claim 12 further comprising pulling a pull wire to expand the mechanical expander.

19. The method of claim 12 further comprising rotating a torque shaft of the delivery catheter to release the coupling element from the partitioning device.

20. The method of claim 12, wherein the mechanical expander is self-expanding.

21. A method of reducing ventricular volume to treat heart disease, the method comprising:
    percutaneously guiding an expandable partitioning device having a membrane on a frame and a contracted configuration on an end of an elongate delivery catheter to which the partitioning device is releasably coupled, into a patient's ventricle through an inner lumen of a guide catheter;
    positioning the expandable partitioning device in the contracted configuration near an apex of the patient's ventricle;
    expanding the partitioning device by expanding an expansion member comprising an expandable structure of the delivery catheter proximal to a distal end of the delivery catheter, to apply outward pressure to the contracted partitioning device to expand the partitioning device;
    securing and sealing a periphery of the partitioning device to a wall of the ventricle;
    releasing a coupling element distal to the expansion member on the delivery catheter to deploy the partitioning device; and
    after the step of expanding the partitioning device by expanding an expansion member, collapsing the expansion member and withdrawing the delivery catheter from the patient's ventricle;
    wherein the step of expanding the partitioning device by expanding an expansion member comprises expanding a structure of the delivery catheter comprising a plurality of discrete arms joined at their proximal and distal ends, by bringing the proximal and distal ends closer together.

* * * * *